United States Patent
Pan et al.

(10) Patent No.: US 11,883,463 B2
(45) Date of Patent: Jan. 30, 2024

(54) RESTORATION OF VISUAL RESPONSES BY IN VIVO DELIVERY OF RHODOPSIN NUCLEIC ACIDS

(71) Applicants: Wayne State University, Detroit, MI (US); Salus University, Elkins Park, PA (US)

(72) Inventors: Zhuo-Hua Pan, Troy, MI (US); Alexander M. Dizhoor, Dresher, PA (US)

(73) Assignees: Wayne State University, Detroit, MI (US); Salus University, Elkins Park, PA (US)

( * ) Notice: Subject to any disclaimer, the term of this patent is extended or adjusted under 35 U.S.C. 154(b) by 337 days.

(21) Appl. No.: 16/700,201

(22) Filed: Dec. 2, 2019

(65) Prior Publication Data

US 2021/0100875 A1  Apr. 8, 2021

Related U.S. Application Data

(63) Continuation of application No. 15/676,573, filed on Aug. 14, 2017, now abandoned, which is a continuation of application No. 13/899,198, filed on May 21, 2013, now Pat. No. 9,730,981, which is a continuation of application No. 12/299,574, filed as application No. PCT/US2007/068263 on May 4, 2007, now Pat. No. 8,470,790.

(60) Provisional application No. 60/797,357, filed on May 4, 2006.

(51) Int. Cl.
| | |
|---|---|
| *A61K 48/00* | (2006.01) |
| *A61K 38/17* | (2006.01) |
| *C07K 14/705* | (2006.01) |
| *C12N 15/86* | (2006.01) |
| *A61P 27/02* | (2006.01) |
| *A61K 38/00* | (2006.01) |

(52) U.S. Cl.
CPC .......... *A61K 38/177* (2013.01); *A61K 48/005* (2013.01); *A61P 27/02* (2018.01); *C07K 14/705* (2013.01); *C12N 15/86* (2013.01); *A61K 38/00* (2013.01); *C12N 2750/14143* (2013.01); *C12N 2830/002* (2013.01); *C12N 2830/008* (2013.01)

(58) Field of Classification Search
None
See application file for complete search history.

(56) References Cited

PUBLICATIONS

Bennett et al., 1999—N. Chirmule, A.R. Gupta and Y. Huang et al., Stable transgene expression in rod photoreceptors after recombinant adeno-associated virus-mediated gene transfer to monkey retina, Proc. Natl. Acad. Sci. USA 96 (1999), pp. 9920-9925.
European Search Report and Written Opinion for the European Application No. EP18176101, dated Nov. 13, 2018, 9 pages.
Fitzsimons et al., 2002—H.L. Fitzsimons, R.J. Bland and M.J. During, Promoters and regulatory elements that improve adeno-associated virus transgene expression in the brain, Methods 28 (2002), pp. 227-236.
Flannery et al., 1997—J.G. Flannery, S. Zolotukhin, M.I. Vaquero, M.M. LaVail, N. Muzyczka and W.W. Hauswirth, Efficient photo-receptor-targeted gene expression in vivo by recombinant adeno-associated virus, Proc. Natl. Acad. Sci. USA 94 (1997), pp. 6916-6921.
Flotte, 2004—T.R. Flotte, Gene therapy progress and prospects: recombinant adeno-associated virus (rAAV) vectors, Gene Ther. 11 (2004), pp. 805-810.
Han, Xue, and Edward S Boyden. "Multiple-color optical activation, silencing, and desynchronization of neural activity, with single-spike temporal resolution." PloS one vol. 2,3 e299. Mar. 21, 2007.
Harvey et al., 2002—A.R. Harvey, W. Kamphuis, R. Eggers, N.A. Symons, B. Blits, S. Niclou, G.J. Boer and J. Verhaagen, Intravitreal injection of adeno-associated viral vectors results in the transduction of different types of retinal neurons in neonatal and adult rats: a comparison with lentiviral vectors, Mal. Cell. Neurosci. 21 (2002), pp. 141-157.
Li et al., 2005—X. Li, D.V. Gutierrez, M.G. Hanson, J. Han, M.D. Mark, H. Chiel, P. Hegemann, L.T. Landmesser and S. Herlitze, Fast noninvasive activation and inhibition of neural and network activity by vertebrate rhodopsin and green algae channelrhodopsin, Proc. Natl. Acad. Sci. USA 102 (2005), pp. 17816-17821.

*Primary Examiner* — Michael D Burkhart
(74) *Attorney, Agent, or Firm* — KDW Firm PLLC

(57) ABSTRACT

Nucleic acid vectors encoding light-gated cation-selective membrane channels, in particular channelrhodopsin-2 (Chop2), converted inner retinal neurons to photosensitive cells in photoreceptor-degenerated retina in an animal model. Such treatment restored visual perception and various aspects of vision. A method of restoring light sensitivity to a retina of a subject suffering from vision loss due to photoreceptor degeneration, as in retinitis pigmentosa or macular degeneration, is provided. The method comprises delivering to the subject by intravitreal or subretinal injection, the above nucleic acid vector which comprises an open reading frame encoding a rhodopsin, to which is operatively linked a promoter and transcriptional regulatory sequences, so that the nucleic acid is expressed in inner retinal neurons. These cells, normally light-insensitive, are converted to a light-sensitive state and transmit visual information to the brain, compensating for the loss, and leading to restoration of various visual capabilities.

10 Claims, 10 Drawing Sheets

Specification includes a Sequence Listing.

FIG. 1A
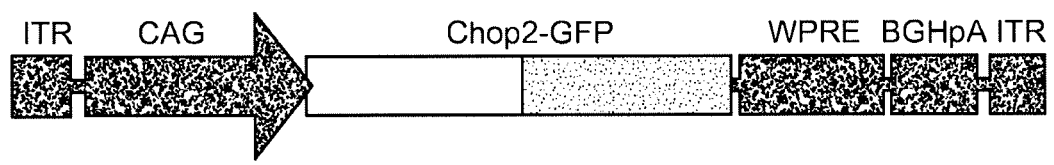
FIG. 1B  FIG. 1C  FIG. 1D
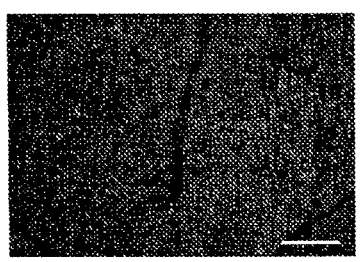 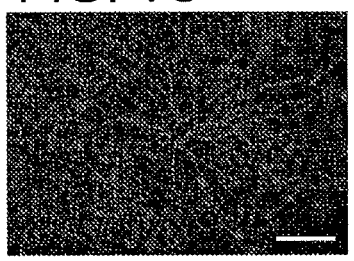 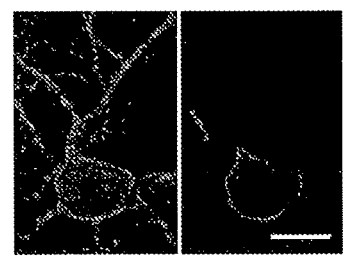
FIG. 1E  FIG. 1F  FIG. 1G
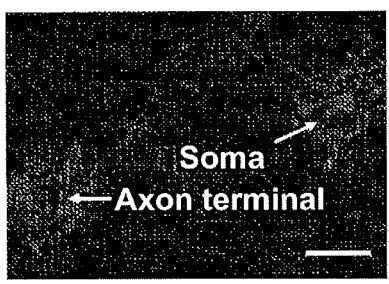 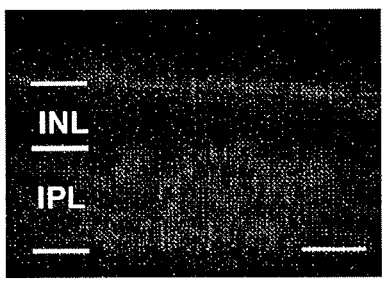 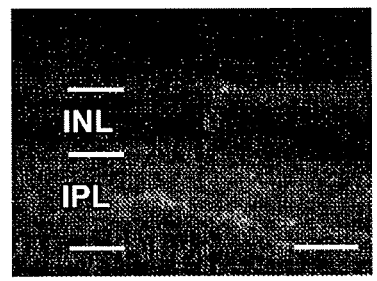
FIG. 1H  FIG. 1I
 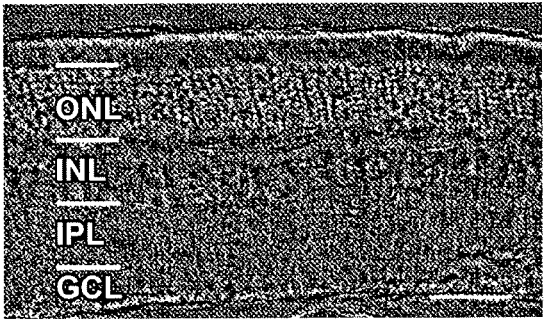

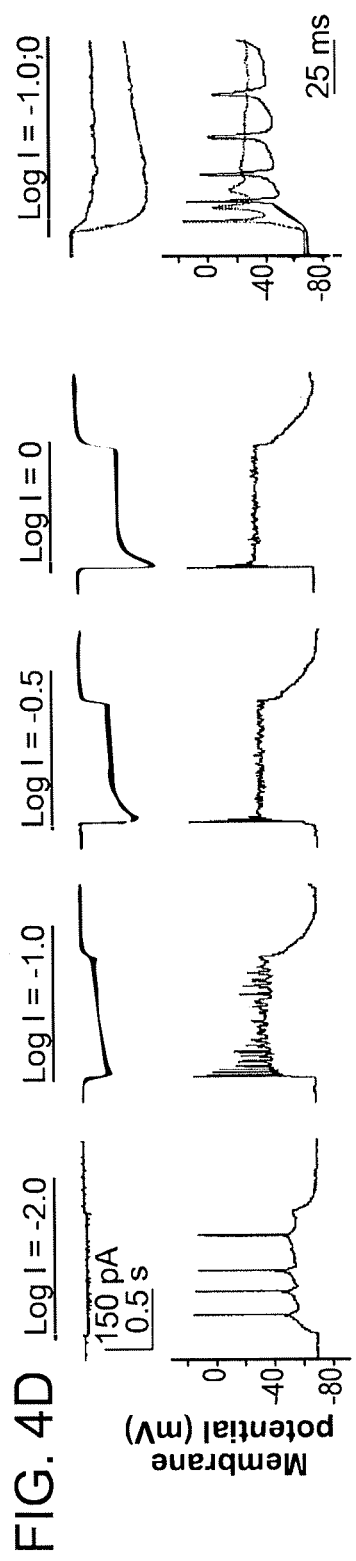
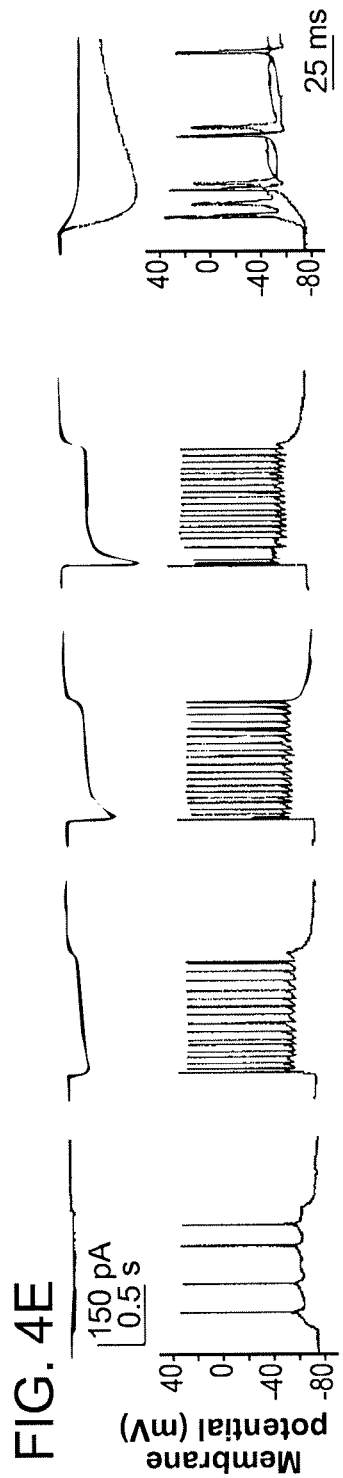
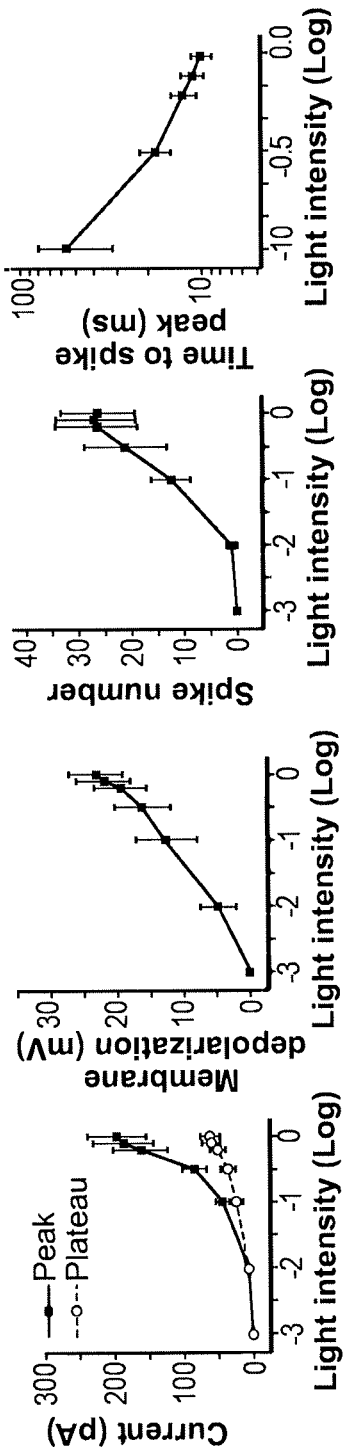

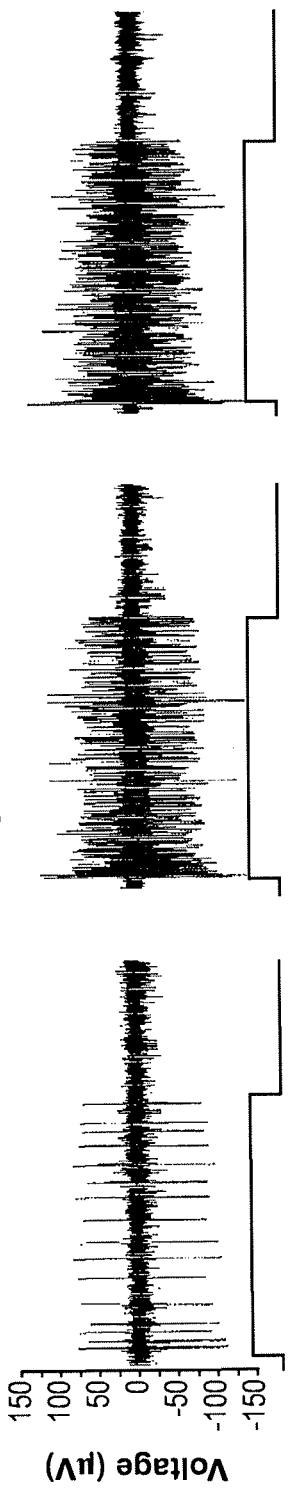
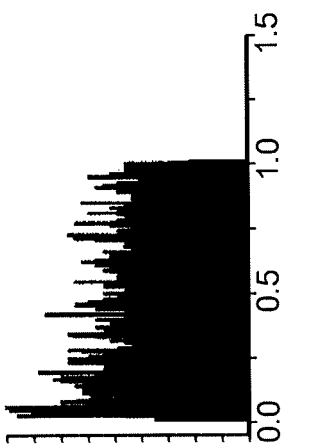
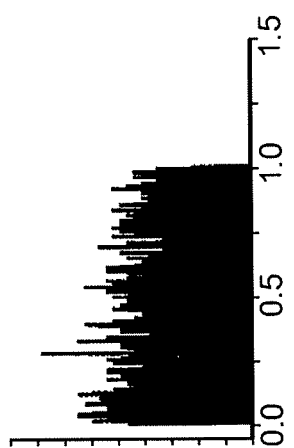
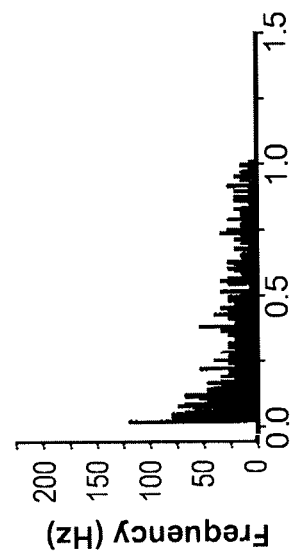

SEQUENCE LISTING

```
<160> NUMBER OF SEQ ID NOS: 9

<210> SEQ ID NO 1
<211> LENGTH: 6987
<212> TYPE: DNA
<213> ORGANISM: Artificial Sequence
<220> FEATURE:
<223> OTHER INFORMATION: Expression vector rAAV2-CAG-Chop2-GFP-WPRE

<400> SEQUENCE: 1
cctgcaggca gctgcgcgct cgctcgctca ctgaggccgc ccgggcaaag cccggcgtc       60 gggcgacctt tggtcgcccg gcctcagtga gcgagcgagc gcgcagagag ggagtggcca     120
actccatcac tagggggttcc tgcggccgca acgcgttacg tatcggatcc agaattcgtg    180
atatctgaat tcgtcgacaa gcttctcgag cctaggctag ctctagacca cacgtgtggg    240
```

```
ggccggccgt aatgagacgc acaaactaat atcacaaact ggaaatgtct atcaatatat    300
agttgctcta gttattaata gtaatcaatt acggggtcat tagttcatag cccatatatg    360
gagttccgcg ttacataact tacggtaaat ggcccgcctg gctgaccgcc caacgacccc    420
cgcccattga cgtcaataat gacgtatgtt cccatagtaa cgccaatagg gactttccat    480
tgacgtcaat gggtggagta tttacggtaa actgcccact tggcagtaca tcaagtgtat    540
catatgccaa gtacgccccc tattgacgtc aatgacggta aatggcccgc ctggcattat    600
gcccagtaca tgaccttatg ggactttcct acttggcagt acatctacgt attagtcatc    660
gctattacca tgcatggtcg aggtgagccc cacgttctgc ttcactctcc ccatctcccc    720
cccctcccca cccccaattt tgtatttatt tattttttaa ttattttgtg cagcgatggg    780
ggcggggggg gggggggggc gcgcgccagg cggggcgggg cggggcgagg ggcggggcgg    840
ggcgaggcgg agaggtgcgg cggcagccaa tcagagcggc gcgctccgaa agtttccttt    900
tatggcgagg cggcggcggc ggcggcccta taaaaagcga agcgcgcggc gggcgggagt    960
cgctgcgcgc tgccttcgcc ccgtgccccg ctccgccgcc gcctcgcgcc gcccgccccg   1020
gctctgactg accgcgttac tcccacaggt gagcgggcgg gacggccctt ctccttcggg   1080
ctgtaattag cgcttggttt aatgacggct tgtttctttt ctgtggctgc gtgaaagcct   1140 tgagggctc cggagggcc cgagctcgcg atccgcagcc atggattatg gaggcgccct   1200
gagtgccgtt gggcgcgagc tgctatttgt aacgaaccca gtagtcgtca atggctctgt   1260
acttgtgcct gaggaccagt gttactgcgc gggctggatt gagtcgcgtg gcacaaacgg   1320
tgcccaaacg gcgtcgaacg tgctgcaatg gcttgctgct ggcttctcca tcctactgct   1380
tatgttttac gcctaccaaa catggaagtc aacctgcggc tgggaggaga tctatgtgtg   1440
cgctatcgag atggtcaagg tgattcttga gttcttcttc gagtttaaga acccgtccat   1500
gctgtatcta gccacaggcc accgcgtcca gtggttgcgt tacgccgagt ggcttctcac   1560
ctgcccggtc attctcattc acctgtcaaa cctgacgggc ttgtccaacg actacagcag   1620
gcgcactatg ggtctgcttg tgtctgatat tggcacaatt gtgtggggcg ccacttccgc   1680 tatgccacc ggatacgtca aggtcatctt cttctgcctg ggtctgtgtt atggtgctaa   1740
cacgttcttt cacgctgcca aggcctacat cgagggttac cataccgtgc cgaagggccg   1800
gtgtcgccag gtggtgactg gcatggcttg gctcttcttc gtatcatggg gtatgttccc   1860
catcctgttc atcctcggcc ccgagggctt cggcgtcctg agcgtgtacg gctccaccgt   1920
cggccacacc atcattgacc tgatgtcgaa gaactgctgg ggtctgctcg gccactacct   1980
gcgcgtgctg atccacgagc atatcctcat ccacggcgac attcgcaaga ccaccaaatt   2040
gaacattggt ggcactgaga ttgaggtcga cgctggtg gaggacgagg ccgaggctgg   2100
cgcggtcaac aagggcaccg gcaaggaatt cggaggcgga ggtggagcta gcaaaggaga   2160
agaactcttc actggagttg tcccaattct tgttgaatta gatggtgatg ttaacggcca   2220
caagttctct gtcagtggag agggtgaagg tgatgcaaca tacggaaaac ttaccctgaa   2280
gttcatctgc actactggca aactgcctgt tccatggcca acactagtca ctactctgtg   2340
ctatggtgtt caatgctttt caagataccc ggatcatatg aaacggcatg acttttcaa   2400 gagtgccatg cccgaaggtt atgtacagga aggaccatc ttcatcaaag atgacggcaa   2460
ctacaagaca cgtgctgaag tcaagtttga aggtgatacc cttgttaata gaatcgagtt   2520
aaaaggtatt gacttcaagg aagatggcaa cattctggga cacaaattgg aatacaacta   2580
taactcacac aatgtataca tcatggcaga caaacaaaag aatggaatca agtgaactt   2640
```

-continued

```
caagacccgc cacaacattg aagatggaag cgttcaacta gcagaccatt atcaacaaaa    2700
tactccaatt ggcgatggcc ctgtccttt accagacaac cattacctgt ccacacaatc     2760 tgcccttttcg aaagatccca acgaaaagag agaccacatg gtccttcttg agtttgtaac   2820
agctgctggg attacacatg gcatggatga actgtacaac atcgattgac taagcttgcc    2880
tcgagaattc acgcgtggta ccgataatca acctctggat tacaaaattt gtgaaagatt   2940
gactggtatt cttaactatg ttgctccttt tacgctatgt ggatacgctg ctttaatgcc    3000
tttgtatcat gctattgctt cccgtatggc tttcattttc tcctccttgt ataaatcctg    3060
gttgctgtct ctttatgagg agttgtggcc cgttgtcagg caacgtggcg tggtgtgcac    3120
tgtgtttgct gacgcaaccc ccactggttg gggcattgcc accacctgtc agctccttc    3180 cgggactttc gctttccccc tccctattgc cacggcggaa ctcatcgccg cctgccttgc    3240
ccgctgctgg acagggctc ggctgttggg cactgacaat tccgtggtgt tgtcggggaa     3300
gctgacgtcc tttccatggc tgctcgcctg tgttgccacc tggattctgc gcgggacgtc    3360
cttctgctac gtcccttcgg ccctcaatcc agcggacctt ccttcccgcg gcctgctgcc   3420
ggctctgcgg cctcttccgc gtcttcgcct tcgccctcag acgagtcgga tctccctttg    3480
ggccgcctcc ccgcctgatc cggccgcggg gatccagaca tgataagata cattgatgag   3540
tttggacaaa ccacaactag aatgcagtga aaaaatgct ttatttgtga aatttgtgat    3600
gctattgctt tatttgtaac cattataagc tgcaataaac aagttaacaa caacaattgc    3660
attcatttta tgtttcaggt tcaggggag gtgtgggagg ttttttcgga tcctctagag     3720
tcgagagatc tacgggtggc atccctgtga cccctcccca gtgcctctcc tggccctgga    3780
agttgccact ccagtgccca ccagccttgt cctaataaaa ttaagttgca tcattttgtc   3840
tgactaggtg tccttctata atattatggg gtggaggggg gtggtatgga gcaaggggca    3900
agttgggaag acaacctgta gggcctgcgg ggtctattgg gaaccaagct ggagtgcagt    3960
ggcacaatct tggctcactg caatctccgc ctcctgggtt caagcgattc tcctgcctca    4020
gcctcccgag ttgttgggat tccaggcatg catgaccagg ctcagctaat ttttgttttt   4080
ttggtagaga cggggtttca ccatattggc caggctggtc tccaactcct aatctcaggt   4140
gatctaccca ccttggcctc ccaaattgct gggattacag gcgtgaacca ctgctcccct    4200
ccctgtcctt ctgattttgt aggtaaccac gtgcggaccg agcggccgca ggaaccccta   4260
gtgatggagt tggccactcc ctctctgcgc gctcgctcgc tcactgaggc cgggcgacca    4320
aaggtcgccc gacgccccggg ctttgccggg gcggcctcag tgagcgagcg agcgcgcagc   4380
tgcctgcagg ggcgcctgat gcggtatttt ctccttacgc atctgtgcgg tatttcacac   4440
cgcatacgtc aaagcaacca tagtacgcgc cctgtagcgg cgcattaagc gcggcgggtg    4500
tggtggttac gcgcagcgtg accgctacac ttgccagcgc cctagcgccc gctcctttcg   4560
ctttcttccc ttcctttctc gccacgttcg ccggctttcc ccgtcaagct ctaaatcggg    4620
ggctcccttt agggttccga tttagtgctt tacggcacct cgaccccaaa aaacttgatt    4680
tgggtgatgg ttcacgtagt gggccatcgc cctgatagac ggtttttcgc cctttgacgt   4740
tggagtccac gttctttaat agtggactct tgttccaaac tggaacaaca ctcaaccta    4800 tctcgggcta ttcttttgat ttataaggga ttttgccgat ttcggcctat tggttaaaaa    4860
atgagctgat ttaacaaaaa tttaacgcga attttaacaa atattaacg tttacaattt    4920 tatggtgcac tctcagtaca atctgctctg atgccgcata gttaagccag ccccgacacc    4980
```

-continued

```
cgccaacacc cgctgacgcg ccctgacggg cttgtctgct cccggcatcc gcttacagac    5040
aagctgtgac cgtctccggg agctgcatgt gtcagaggtt ttcaccgtca tcaccgaaac    5100
gcgcgagacg aaagggcctc gtgatacgcc tatttttata ggttaatgtc atgataataa    5160
tggtttctta gacgtcaggt ggcacttttc ggggaaatgt gcgcggaacc cctatttgtt    5220
tatttttcta atacattca aatatgtatc cgctcatgag acaataaccc tgataaatgc    5280
ttcaataata ttgaaaaagg aagagtatga gtattcaaca tttccgtgtc gcccttattc    5340
ccttttttgc ggcattttgc cttcctgttt ttgctcaccc agaaacgctg gtgaaagtaa    5400
aagatgctga agatcagttg ggtgcacgag tgggttacat cgaactggat ctcaacagcg    5460
gtaagatcct tgagagtttt cgccccgaag aacgttttcc aatgatgagc acttttaaag    5520
ttctgctatg tggcgcggta ttatcccgta ttgacgccgg gcaagagcaa ctcggtcgcc    5580
gcatacacta ttctcagaat gacttggttg agtactcacc agtcacagaa aagcatctta    5640
cggatggcat gacagtaaga gaattatgca gtgctgccat aaccatgagt gataacactg    5700
cggccaactt acttctgaca acgatcggag gaccgaagga gctaaccgct tttttgcaca    5760
acatggggga tcatgtaact cgccttgatc gttgggaacc ggagctgaat gaagccatac    5820
caaacgacga gcgtgacacc acgatgcctg tagcaatggc aacaacgttg cgcaaactat    5880
taactggcga actacttact ctagcttccc ggcaacaatt aatagactgg atggaggcgg    5940
ataaagttgc aggaccactt ctgcgctcgg cccttccggc tggctggttt attgctgata    6000
aatctggagc cggtgagcgt gggtctcgcg gtatcattgc agcactgggg ccagatggta    6060
agccctcccg tatcgtagtt atctacacga cggggagtca ggcaactatg gatgaacgaa    6120
atagacagat cgctgagata ggtgcctcac tgattaagca ttggtaactg tcagaccaag    6180
tttactcata tactttttag attgatttaa aacttcattt ttaatttaaa aggatctagg    6240
tgaagatcct ttttgataat ctcatgacca aaatccctta acgtgagttt cgttccact    6300 gagcgtcaga ccccgtagaa aagatcaaag gatcttcttg agatcctttt tttctgcgcg    6360
taatctgctg cttgcaaaca aaaaaaccac cgctaccagc ggtggtttgt ttgccggatc    6420
aagagctacc aactcttttt ccgaaggtaa ctggcttcag cagagcgcag ataccaaata    6480
ctgtccttct agtgtagccg tagttaggcc accacttcaa gaactctgta gcaccgccta    6540
catacctcgc tctgctaatc ctgttaccag tggctgctgc cagtggcgat aagtcgtgtc    6600
ttaccgggtt ggactcaaga cgatagttac cggataaggc gcagcggtcg ggctgaacgg    6660
ggggttcgtg cacacagccc agcttggagc gaacgaccta ccgaactg agataccta    6720 agcgtgagct atgagaaagc gccacgcttc ccgaagggag aaaggcggac aggtatccgg    6780
taagcggcag ggtcggaaca ggagagcgca cgagggagct tccaggggga acgcctggt    6840 atctttatag tcctgtcggg tttcgccacc tctgacttga gcgtcgattt ttgtgatgct    6900
cgtcaggggg gcggagccta tggaaaaacg ccagcaacgc ggccttttta cggttcctgg    6960
ccttttgctg gccttttgct cacatgt                                       6987
```

<210> SEQ ID NO 2
<211> LENGTH: 945
<212> TYPE: DNA
<213> ORGANISM: Artificial sequence
<220> FEATURE:
<223> OTHER INFORMATION: Chop2 sequence from rAAV2-CAG-Chop2-GFP-WPRE
      vector

<400> SEQUENCE: 2

```
atggattatg gaggcgccct gagtgccgtt gggcgcgagc tgctatttgt aacgaaccca    60
gtagtcgtca atggctctgt acttgtgcct gaggaccagt gttactgcgc gggctggatt   120
gagtcgcgtg cacaaacgg tgcccaaacg cgtcgaacg tgctgcaatg cttgctgct    180
ggcttctcca tcctactgct tatgttttac gcctaccaaa catggaagtc aacctgcggc   240
tgggaggaga tctatgtgtg cgctatcgag atggtcaagg tgattcttga gttcttcttc   300
gagtttaaga acccgtccat gctgtatcta gccacaggcc accgcgtcca gtggttgcgt   360
tacgccgagt ggcttctcac ctgcccggtc attctcattc acctgtcaaa cctgacgggc   420
ttgtccaacg actacagcag cgcactatg ggtctgcttg tgtctgatat tggcacaatt    480
gtgtggggcg ccacttccgc tatggccacc ggatacgtca aggtcatctt cttctgcctg   540
ggtctgtgtt atggtgctaa cacgttcttt cacgctgcca aggcctacat cgagggttac   600
cataccgtgc gaagggccg tgtcgccag gtggtgactg cattgcttg gctcttcttc    660
gtatcatggg gtatgttccc catcctgttc atcctcggcc ccgagggctt cggcgtcctg   720
agcgtgtacg gctccaccgt cggccacacc atcattgacc tgatgtcgaa gaactgctgg   780
ggtctgctcg ccactacct gcgcgtgctg atccacgagc atatcctcat ccacggcgac   840
attcgcaaga ccaccaaatt gaacattggt ggcactgaga ttgaggtcga cgctggtg    900
gaggacgagg ccgaggctgg cgcggtcaac aagggcaccg gcaag              945
```

```
<210> SEQ ID NO 3
<211> LENGTH: 315
<212> TYPE: PRT
<213> ORGANISM: Artificial sequence
<220> FEATURE:
<223> OTHER INFORMATION: Chop2 sequence from rAAV2-CAG-Chop2-GFP-WPRE
      vector

<400> SEQUENCE: 3
```

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190
```

```
Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Asn Lys Gly Thr Gly Lys
305                 310                 315

<210> SEQ ID NO 4
<211> LENGTH: 2241
<212> TYPE: DNA
<213> ORGANISM: Chlamydomonas reinhardtii

<400> SEQUENCE: 4
```

| | | | | | |
|---|---|---|---|---|---|
| gcatctgtcg | ccaagcaagc | attaaacatg | gattatggag | gcgccctgag | tgccgttggg | 60 |
| cgcgagctgc | tatttgtaac | gaacccagta | gtcgtcaatg | gctctgtact | tgtgcctgag | 120 |
| gaccagtgtt | actgcgcggg | ctggattgag | tcgcgtggca | caaacggtgc | ccaaacggcg | 180 |
| tcgaacgtgc | tgcaatggct | tgctgctggc | ttctccatcc | tactgcttat | gttttacgcc | 240 |
| taccaaacat | ggaagtcaac | ctgcggctgg | gaggagatct | atgtgtgcgc | tatcgagatg | 300 |
| gtcaaggtga | ttctcgagtt | cttcttcgag | tttaagaacc | cgtccatgct | gtatctagcc | 360 |
| acaggccacc | gcgtccagtg | gttgcgttac | gccgagtggc | ttctcacctg | cccggtcatt | 420 |
| ctcattcacc | tgtcaaacct | gacgggcttg | tccaacgact | acagcaggcg | caccatgggt | 480 |
| ctgcttgtgt | ctgatattgg | cacaattgtg | tggggcgcca | cttccgccat | ggccaccgga | 540 |
| tacgtcaagg | tcatcttctt | ctgcctgggt | ctgtgttatg | gtgctaacac | gttctttcac | 600 |
| gctgccaagg | cctacatcga | gggttaccac | accgtgccga | agggccggtg | tcgccaggtg | 660 |
| gtgactggca | tggcttggct | cttcttcgta | tcatggggta | tgttccccat | cctgttcatc | 720 |
| ctcggccccg | agggcttcgg | cgtcctgagc | gtgtacggct | ccaccgtcgg | ccacaccatc | 780 |
| attgacctga | tgtcgaagaa | ctgctggggt | ctgctcggcc | actacctgcg | cgtgctgatc | 840 |
| cacgagcata | tcctcatcca | cggcgacatt | cgcaagacca | ccaaattgaa | cattggtggc | 900 |
| actgagattg | aggtcgagac | gctggtggag | gacgaggccg | aggctggcgc | ggtcaacaag | 960 |
| ggcaccggca | gtacgcctc | ccgcgagtcc | ttcctggtca | tgcgcgacaa | gatgaaggag | 1020 |
| aagggcattg | acgtgcgcgc | ctctctggac | aacagcaagg | aggtggagca | ggagcaggcc | 1080 |
| gccagggctg | ccatgatgat | gatgaacggc | aatggcatgg | gtatgggaat | gggaatgaac | 1140 |
| ggcatgaacg | gaatgggcgg | tatgaacggg | atggctggcg | cgccaagcc | cggcctggag | 1200 |
| ctcactccgc | agctacagcc | cggccgcgtc | atcctggcgg | tgccggacat | cagcatggtt | 1260 |
| gacttcttcc | gcgagcagtt | tgctcagcta | tcggtgacgt | acgagctggt | gccggccctg | 1320 |
| ggcgctgaca | cacactggc | gctggttacg | caggcgcaga | acctgggcgg | cgtggacttt | 1380 |
| gtgttgattc | accccgagtt | cctgcgcgac | cgctctagca | ccagcatcct | gagccgcctg | 1440 |

```
cgcggcgcgg gccagcgtgt ggctgcgttc ggctgggcgc agctggggcc catgcgtgac    1500
ctgatcgagt ccgcaaacct ggacggctgg ctggagggcc cctcgttcgg acagggcatc    1560
ctgccggccc acatcgttgc cctggtggcc aagatgcagc agatgcgcaa gatgcagcag    1620
atgcagcaga ttggcatgat gaccggcggc atgaacggca tgggcggcgg tatgggcggc    1680
ggcatgaacg gcatgggcgg cggcaacggc atgaacaaca tgggcaacgg catgggcggc    1740
ggcatgggca acggcatggg cggcaatggc atgaacggaa tgggtggcgg caacggcatg    1800
aacaacatgg gcggcaacgg aatggccggc aacggaatgg gcggcggcat gggcggcaac    1860
ggtatgggtg gctccatgaa cggcatgagc tccggcgtgg tggccaacgt gacgccctcc    1920
gccgccggcg gcatgggcgg catgatgaac ggcggcatgg ctgcgcccca gtcgcccggc    1980
atgaacggcg gccgcctggg taccaacccg ctcttcaacg ccgcgccctc accgctcagc    2040
tcgcagctcg gtgccgaggc aggcatgggc agcatgggag catgggcgg aatgagcgga    2100 atgggaggca tgggtggaat gggggggcatg gcggcgccg cgccgccac gacgcaggct    2160 gcgggcggca acgcggaggc ggagatgctg cagaatctca tgaacgagat caatcgcctg    2220
aagcgcgagc ttggcgagta a                                              2241

<210> SEQ ID NO 5
<211> LENGTH: 2214
<212> TYPE: DNA
<213> ORGANISM: Chlamydomonas reinhardtii

<400> SEQUENCE: 5
atggattatg gaggcgccct gagtgccgtt gggcgcgagc tgctatttgt aacgaaccca      60
gtagtcgtca atggctctgt acttgtgcct gaggaccagt gttactgcgc gggctggatt     120
gagtcgcgtg gcacaaacgg tgcccaaacg gcgtcgaacg tgctgcaatg gcttgctgct     180
ggcttctcca tcctactgct tatgttttac gcctaccaaa catggaagtc aacctgcggc     240
tgggaggaga tctatgtgtg cgctatcgag atggtcaagg tgattctcga gttcttcttc     300
gagtttaaga acccgtccat gctgtatcta gccacaggcc accgcgtcca gtggttgcgt     360
tacgccgagt ggcttctcac ctgcccggtc attctcattc acctgtcaaa cctgacgggc     420
ttgtccaacg actacagcag gcgcaccatg ggtctgcttg tgtctgatat tggcacaatt     480
gtgtggggcg ccacttccgc catggccacc ggatacgtca aggtcatctt cttctgcctg     540
ggtctgtgtt atggtgctaa cacgttcttt cacgctgcca aggcctacat cgagggttac     600
cacaccgtgc cgaagggccg tgtcgccag tggtgactg catggcttg gctcttcttc       660 gtatcatggg gtatgttccc catcctgttc atcctcggcc ccgagggctt cggcgtcctg     720
agcgtgtacg gctccaccgt cggccacacc atcattgacc tgatgtcgaa gaactgctgg     780
ggtctgctcg ccactacct gcgcgtgctg atccacgagc atatcctcat ccacggcgac     840
attcgcaaga ccaccaaatt gaacattggt ggcactgaga ttgaggtcga cgctggtg      900 gaggacgagg ccgaggctgg cgcggtcaac aagggcaccg gcaagtacgc ctcccgcgag     960
tccttcctgg tcatgcgcga caagatgaag gagaagggca ttgacgtgcg cgcctctctg    1020
gacaacagca aggaggtgga gcaggagcag gccgccaggc tgccatgat gatgatgaac    1080 ggcaatggca tgggtatggg aatgggaatg aacggcatga acggaatggg cggtatgaac    1140
gggatggctg gcgcgccaa gcccggcctg gagctcactc cgcagctaca gcccggccgc    1200
gtcatcctgg cggtgccgga catcagcatg gttgacttct ccgcgagca gtttgctcag    1260
```

```
ctatcggtga cgtacgagct ggtgccggcc ctgggcgctg acaacacact ggcgctggtt    1320
acgcaggcgc agaacctggg cggcgtggac tttgtgttga ttcacccga  gttcctgcgc    1380 gaccgctcta gcaccagcat cctgagccgc ctgcgcggcg cgggccagcg tgtggctgcg    1440
ttcggctggg cgcagctggg gcccatgcgt gacctgatcg agtccgcaaa cctggacggc    1500
tggctggagg gccctcgtt  cggacagggc atcctgccgg cccacatcgt tgccctggtg    1560
gccaagatgc agcagatgcg caagatgcag cagatgcagc agattggcat gatgaccggc    1620
ggcatgaacg gcatgggcgg cggtatgggc ggcggcatga acggcatggg cggcggcaac    1680
ggcatgaaca acatgggcaa cggcatgggc ggcggcatgg gcaacggcat gggcggcaat    1740
ggcatgaacg gaatgggtgg cggcaacggc atgaacaaca tgggcggcaa cggaatggcc    1800
ggcaacggaa tgggcggcgg catgggcggc aacggtatgg gtggctccat gaacggcatg    1860
agctccggcg tggtggccaa cgtgacgccc tccgccgccg cgcatgggc  cggcatgatg    1920 aacggcggca tggctgcgcc ccagtcgccc ggcatgaacg gcggccgcct gggtaccaac    1980
ccgctcttca cgccgcgcc  ctcaccgctc agctcgcagc tcggtgccga ggcaggcatg    2040
ggcagcatgg gaggcatggg cggaatgagc ggaatgggag gcatgggtgg aatgggggc    2100 atgggcggcg ccggcgccgc cacgacgcag gctgcgggcg gcaacgcgga ggcggagatg    2160
ctgcagaatc tcatgaacga gatcaatcgc ctgaagcgcg agcttggcga gtaa          2214
```

<210> SEQ ID NO 6
<211> LENGTH: 737
<212> TYPE: PRT
<213> ORGANISM: Chlamydomonas reinhardtii

<400> SEQUENCE: 6

```
Met Asp Tyr Gly Gly Ala Leu Ser Ala Val Gly Arg Glu Leu Leu Phe
1               5                  10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205
```

-continued

```
Arg Gln Val Val Thr Gly Met Ala Trp Leu Phe Phe Val Ser Trp Gly
    210                 215                 220
Met Phe Pro Ile Leu Phe Ile Leu Gly Pro Glu Gly Phe Gly Val Leu
225                 230                 235                 240
Ser Val Tyr Gly Ser Thr Val Gly His Thr Ile Ile Asp Leu Met Ser
                245                 250                 255
Lys Asn Cys Trp Gly Leu Leu Gly His Tyr Leu Arg Val Leu Ile His
                260                 265                 270
Glu His Ile Leu Ile His Gly Asp Ile Arg Lys Thr Thr Lys Leu Asn
                275                 280                 285
Ile Gly Gly Thr Glu Ile Glu Val Glu Thr Leu Val Glu Asp Glu Ala
290                 295                 300
Glu Ala Gly Ala Val Asn Lys Gly Thr Gly Lys Tyr Ala Ser Arg Glu
305                 310                 315                 320
Ser Phe Leu Val Met Arg Asp Lys Met Lys Glu Lys Gly Ile Asp Val
                325                 330                 335
Arg Ala Ser Leu Asp Asn Ser Lys Glu Val Glu Gln Glu Gln Ala Ala
                340                 345                 350
Arg Ala Ala Met Met Met Met Asn Gly Asn Gly Met Gly Met Gly Met
                355                 360                 365
Gly Met Asn Gly Met Asn Gly Met Gly Gly Met Asn Gly Met Ala Gly
370                 375                 380
Gly Ala Lys Pro Gly Leu Glu Leu Thr Pro Gln Leu Gln Pro Gly Arg
385                 390                 395                 400
Val Ile Leu Ala Val Pro Asp Ile Ser Met Val Asp Phe Phe Arg Glu
                405                 410                 415
Gln Phe Ala Gln Leu Ser Val Thr Tyr Glu Leu Val Pro Ala Leu Gly
                420                 425                 430
Ala Asp Asn Thr Leu Ala Leu Val Thr Gln Ala Gln Asn Leu Gly Gly
                435                 440                 445
Val Asp Phe Val Leu Ile His Pro Glu Phe Leu Arg Asp Arg Ser Ser
450                 455                 460
Thr Ser Ile Leu Ser Arg Leu Arg Gly Ala Gly Gln Arg Val Ala Ala
465                 470                 475                 480
Phe Gly Trp Ala Gln Leu Gly Pro Met Arg Asp Leu Ile Glu Ser Ala
                485                 490                 495
Asn Leu Asp Gly Trp Leu Glu Gly Pro Ser Phe Gly Gln Gly Ile Leu
                500                 505                 510
Pro Ala His Ile Val Ala Leu Val Ala Lys Met Gln Gln Met Arg Lys
                515                 520                 525
Met Gln Gln Met Gln Gln Ile Gly Met Met Thr Gly Gly Met Asn Gly
530                 535                 540
Met Gly Gly Gly Met Gly Gly Gly Met Asn Gly Met Gly Gly Gly Asn
545                 550                 555                 560
Gly Met Asn Asn Met Gly Asn Gly Met Gly Gly Met Gly Asn Gly
                565                 570                 575
Met Gly Gly Asn Gly Met Asn Gly Met Gly Gly Asn Gly Met Asn
                580                 585                 590
Asn Met Gly Gly Asn Gly Met Ala Gly Asn Gly Met Gly Gly Gly Met
                595                 600                 605
Gly Gly Asn Gly Met Gly Gly Ser Met Asn Gly Met Ser Ser Gly Val
610                 615                 620
Val Ala Asn Val Thr Pro Ser Ala Ala Gly Gly Met Gly Gly Met Met
```

```
                625                 630                 635                 640
Asn Gly Gly Met Ala Ala Pro Gln Ser Pro Gly Met Asn Gly Arg
                    645                 650                 655

Leu Gly Thr Asn Pro Leu Phe Asn Ala Ala Pro Ser Pro Leu Ser Ser
                660                 665                 670

Gln Leu Gly Ala Glu Ala Gly Met Gly Ser Met Gly Met Gly Gly
                675                 680                 685

Met Ser Gly Met Gly Gly Met Gly Gly Met Gly Met Gly Gly Ala
                690                 695                 700

Gly Ala Ala Thr Thr Gln Ala Ala Gly Gly Asn Ala Glu Ala Glu Met
705                 710                 715                 720

Leu Gln Asn Leu Met Asn Glu Ile Asn Arg Leu Lys Arg Glu Leu Gly
                725                 730                 735

Glu

<210> SEQ ID NO 7
<211> LENGTH: 933
<212> TYPE: DNA
<213> ORGANISM: Artificial Sequence
<220> FEATURE:
<223> OTHER INFORMATION: human codon-optimized Chop2

<400> SEQUENCE: 7
atggactatg gcggcgcttt gtctgccgtc ggacgcgaac ttttgttcgt tactaatcct      60
gtggtggtga acgggtccgt cctggtccct gaggatcaat gttactgtgc cggatggatt     120
gaatctcgcg gcacgaacgg cgctcagacc gcgtcaaatg tcctgcagtg gcttgcagca     180
ggattcagca ttttgctgct gatgttctat gcctaccaaa cctggaaatc tacatgcggc     240
tgggaggaga tctatgtgtg cgccattgaa atggttaagg tgattctcga gttcttttt     300
gagtttaaga tccctctat gctctacctt gccacaggac accgggtgca gtggctgcgc     360
tatgcagagt ggctgctcac ttgtcctgtc atccttatcc acctgagcaa cctcaccggc     420
ctgagcaacg actacagcag gagaaccatg ggactccttg tctcagacat cgggactatc     480
gtgtgggggg ctaccagcgc catggcaacc ggctatgtta agtcatctt cttttgtctt     540
ggattgtgct atggcgcgaa acatttttt cacgccgcca agcatatat cgagggttat     600
catactgtgc aaagggtcg gtgccgccag gtcgtgaccg gcatggcatg gctgttttc     660
gtgagctggg gtatgttccc aattctcttc attttgggc cgaaggtttt tggcgtcctg     720
agcgtctatg gctccaccgt aggtcacacg attattgatc tgatgagtaa aaattgttgg     780
gggttgttgg acactacct gcgcgtcctg atccacgagc acatattgat tcacggagat     840
atccgcaaaa ccaccaaact gaacatcggc ggaacggaga tcgaggtcga gactctcgtc     900
gaagacgaag ccgaggccgg agccgtgcca taa                                 933

<210> SEQ ID NO 8
<211> LENGTH: 310
<212> TYPE: PRT
<213> ORGANISM: Artificial Sequence
<220> FEATURE:
<223> OTHER INFORMATION: human codon-optimized Chop2

<400> SEQUENCE: 8

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
                20                  25                  30
```

Gln Cys Tyr Cys Ala Gly Trp Ile Glu Ser Arg Gly Thr Asn Gly Ala
         35                  40                  45

Gln Thr Ala Ser Asn Val Leu Gln Trp Leu Ala Ala Gly Phe Ser Ile
     50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                 85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
        130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
        210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Glu His Ile Leu Ile His Gly Asp Ile Arg Lys Thr Thr Lys Leu Asn
                260                 265                 270

Ile Gly Gly Thr Glu Ile Glu Val Glu Thr Leu Val Glu Asp Glu Ala
            275                 280                 285

Ile Gly Gly Thr Glu Ile Glu Val Glu Thr Leu Val Glu Asp Glu Ala
        290                 295                 300

Glu Ala Gly Ala Val Pro
305                 310

<210> SEQ ID NO 9
<211> LENGTH: 10123
<212> TYPE: DNA
<213> ORGANISM: Artificial Sequence
<220> FEATURE:
<223> OTHER INFORMATION: mGluR6 promoter region

<400> SEQUENCE: 9
tagaagttag tccactcttc ctcatgggcc ttcgcctctg gtccaaagta ttaccaaagt    60
cacttaaatt aacaagaaca gacacacaca cacccaagct agaactagca gcactagcca   120
gaactcaatt tacattttag agaaaaaggg ggtggaggac agctcctgta gagggaatga   180
tattaacacg ttctgggctc cgtgcccagc atcgttctgc tcctttccaa cagtaaaacc   240
ttagagcaaa ggcacaagtg gaaaaaatgg actgtggaat tcagttaaga tactgtccag   300
caccgaagac tgacagaaac taagtttcac ctccaggatt gaaagcctac aggcgatctg   360
ctcaaggccg acttgactag ctaacctgaa gccggaggct tctttgaccg ctgttcgggc   420

```
agcagaacct ggagtcaggg cccgaggccc tcaccagcag ctgaggcctc tgcgtgcttc      480
cgccaggctc tcagccctgg cccgcaggtt cccggccgtt ccagctctgc cagaaaaccc      540
agaaagctca atgcccagag cgggtaagac taggctcaac tgcgcgtgcg cgcgagccac      600
ctggtttcca ctgtggacta catttcccag aaggcactgt gacactccta cccaccctgt      660
atggtgcaga gtgggacaca ggcgcctaaa gactgagaat caacttttca gttgccacca      720
gctttcaggt ttctgtgcag gcttcattca taattacaat ggtaatacta ctaaagagga      780
aaaagtgagt gtgcattaaa atgttgaaga ataaggctct gactgcttag tttcagatag      840
cgaaaggact gtcctctttc atttttttaat agaaaattat gcttttttcta ggctacaaaa      900
```

```
gttccttgat attactgctg ttgtcatttt gacattgttc ttcgtctggg ctccagctac    2880
tgttctttct acctcccaga caccaacatt gttcttcact caggtttctg cccatgcatc    2940
atctaccttg ctgtgtattc aactggatat ccatatgcaa atggttgaat ttggacccaa    3000
catcatatta cactcaaaaa ttccctcaac atggatcaac gatctaaatg ttagcgctag    3060
aatcacaaaa cactaaaaat aaaacacggg agtgtttagt gatgtcttag ttatggtttc    3120
tattgctgtg ataaaacact gtgattaaaa gcagcagcag tggggtgagg cagggtaggc    3180
aggaaaggtt caatctcagc ttagaactct ctctctctgg tcatgctcca tcagtgaatg    3240
gagtaagagc aggaacttga ggcaggagct gatgcagagg cccagaagga aggaacctgc    3300
ttactggctt gctccttgtg gcttgctcaa cctactttct tgttgactcc aggaccacct    3360
gccaagggct ggcacctccc ctaggggact ggaccctccc acttcaatca ttaatcaaga    3420
aaatgcccca caggggcat tttcaattgt gactctctct tctcagagga ctcttgtttg    3480
ttaacaaaaa actaaccagg gcaggtataa atcttcatga ctttggaatt gcctgtggga    3540
tctcagatgt gctatccaaa cacaaacaat aaaagaaaaa tgcaatttga atcttaacaa    3600
atgttttgaa tcttaaaatg ttatgtatta tgaagaaagt aaaccgataa ctcacagaca    3660
ggaacaaaaa tctttgcaag tcaaaagttt aataagtcca ggctttacac cttaacaaga    3720
agactgagtc tgtggctaca taccgtggca catattacta ctagagcatg ggatgcccct    3780
ggtaacggca acttctgggg accacgtgga tgtccgggga ctgtgcataa cttgtcccac    3840
ccctcactgg atgcggcact ctagagagct ggccccatct ctcacctatg gcggcactct    3900
ggagagtggg ccgggcagca cagtggagct gctcctggct tcgagggtag agatgagcca    3960
gctccaagga tgtgagtgtg ggagagctga ccctgccact tgtctgccat gggtagcaca    4020
ggtgcagatg tgatacacac acacacacac acacacacac acacacacac acacactgcc    4080
ccgcactact cctgaagtca ggagctagtc ccaccectac cagctacagc tctcagaaca    4140
gtcccgggac cttgtctgga gagcacagca gaactaaccc tggtgttgag ggtgcaggaa    4200
acccagcccc aagagtgaaa gctcggaaaa gctggctcca tcattcatct gctgtgaggt    4260
gccatgggtg tgcaggtgat gctctcccca cctcttcact ccctgccacc taaggcagta    4320
gggacagctg gtccccaggg acatcagagt gggagagctg gctctgctcc tcactggctg    4380
tagaactcag aatgggccct gcatcttgtc tgggcagcac aatagggctg gccttgttgg    4440
agggagagag gatggggcag cccagagggt agagtgtagg agaggtggcc ccgacacttg    4500
tctggtgtga ggtggtgtgg atgtaggggc aatgccctcc ctgggcccct cactgcctga    4560
ggcagtcagg agaactgacc ccagggtcat gagagcaggt gagctggccc tgctcccact    4620
ggctgcactt cagagagcag gccctgaatc tcctctgggc agcatagtcg cactagcact    4680
ggtagagggg gcacgggtga actccacccc ccatccccca ccaggttaag agcatgggag    4740
agctggcctt gccacttgtc ttgtgtgagg tgggtgcggg gattatgtcc tcttccccca    4800
cctgcagtgg ctgggagagt tgaccctgga ccatgagagg gagagagagc taatggcccc    4860
tcattggcta tagcacttgg gtgagtgggc ctgcacctca cctgggcaat acagtggagc    4920
tggccctgat ggtgaaagta tgggtgagtt agtccagagg gtatgagagt gtgagaaatg    4980
gcccagcctc tcacaggctg cagcacctgg gagagcgcac cctgaacctt gaatggatag    5040
ctaggtggag cggctctgga ggaatggggtg caaatgaccc atcctgaggg caagagagca    5100
ggagtgctga ccttgcctcc tgccaatgga gggaggtatt gactggccta gctggaagag    5160
```

```
tgctggagag tttactctag tggtgtgggt aagggagagc tggcaagctg accagctcag    5220
ctactaccca gggcaagatc ctgggctctg agccagccca ccccaaaatc gatatcatct    5280
gtgaacagtt gacatgcatg aaaggggcat ccttgctatt ctaaaactgc aggctctcca    5340
tgacacagag caacaacagg ataacccaga ggggtctcaa tgaagatcca atattgatgg    5400
tatcacagaa gctaaagact tcaaaccaga ccgttgactc attataatga acaccttacc    5460
ttcaagtgaa gatgtgtgga cagagggaaa tactgtagga cacactgtga cacactacag    5520
cttgcatggt gagatgtttt ctatgctttg ttttgttgtt gttgttggtg gtggtggtgg    5580
tggtggtggt ggtgtggtgg tggtagtggg gtgtgtgtgt gtgtgtgtgt gtgtgtgtgt    5640
gtgtattatt ttgggggggag gttgcgaggg tgaagaatag atatgaggag atggggagat    5700
gagcagaact ggggtgcatg atgtgaaact cacaaagaat caataaagtt tttaaaaact    5760
cagaaactaa gccgggcggt agtggcgcac gcctttaatc ccagcacttg ggaggcagag    5820
gcaggtggat ttctgagttc aaggccagcc tggtctacaa agtgagttcc aggacagcca    5880
gggatacaca gagaaacctt gtcttaaaaa acaaacaaac aaacaaacaa acaagaaaca    5940
aaaacaaata aaacaaaaaa ccctcagaaa ctagttttaa agcttatcaa agcagactct    6000
actcgctgtt ttactgaatt tcatcaagct aagtacttta ggggagagag aatctcctcc    6060
tcagcctgca gtttctatac tactggactg taaaattccc gagagtaaga tatgaatcct    6120
gggcctgtaa attatattta aactaatata tattcaaaac agtgaattat agggaaaaaa    6180
agaaaactcc gtttatatgg tgcttcattc acccttagtg agctatttcc ctggttgcca    6240
ccaggccacc ctgtggtggc agcactgagt actcctagct gccaagtcag tctttgcaca    6300
gcacattcac atggcgatcg aaccaaagag cgtgtttaat ggtgcagagc tatattgaag    6360
gaagcttgca tagctgggtg tcaacaagtg ctgatggctg attgttttaa tacccccatcc    6420 tgctacattg aaaggtctgc agttgccttg ggcttggcag aggagcctag cggaaagaca    6480
ggctgtcaaa gcagcagtgg gatgagggat gaggtgatag ttagtcctcc ctgtcaactt    6540
actagtttcg aatcacctgg gagacacatt gctgagtgta actgtgaggg gctctctagg    6600
gaggttaaac tgaggggggaa acacccaccc tgaatgtgcg tggcactata actgaatgca    6660
aacgggaaag aaagaaacaa gctggctggg gagcaccaga attcatctct cctttcttcc    6720
tgactgtgga caccatgtga ccagctgcct cacactcttt ccagcaaacc ttgctgtcat    6780
ggaagactgt gttccctcca actgtgagcc agaatagtcc ttctcttgta tcacttgtct    6840
ttgtcaggta ttttgtcata gcaatgagaa acataaccca gtatggagtt acttagttac    6900
acttgctcca tactggtcca cgcaggaccc taaggcctct gtggacattc tcagttgcag    6960
acatcatgct tttcaacacc ttgtgctaga gatggtgaag aatgtctcca actctcctgcc    7020 tacatgttct ctaaaagtga gaaggtggac agcactctta gcactcctag tcagagggca    7080
gaggtttgac ccatacattg aaccctcaaa ggtatagtct taagtctatt tgtgtgcaca    7140
tgcttgcaca cacacacaca cacacacaca cacacacaca cacgtgcacg    7200
ctcccacaca gaagctctgc ttggatagtc tcctgcagtg tcacccactc tggtcaagcc    7260
ccactaagct ggcttccatc acaggaatga actgctctgg gtgtgacaag agaaatcgga    7320
ggatagtggt tatatttctg ctgcttgctc tctccaccag tcatgtccag atctctgctg    7380 ccacccctaat ccaccctgac taatgcactg aagagcccat taatccctgg aggctggggc    7440
tcagcaactg tctccaagat gcctttgctg tccagcatca gagagctcaa tcctgtcctc    7500
tgttgacaat gatgggaaaa tatctttggg ttgaacatct tcacggtgta aatcagttcc    7560
```

```
agagagctag gaaactcaga aatgatgtgg ggagacaact gagggctcct gacccacatg   7620
ggagcttcag ggtgaactaa ccccatcttc cccctccaa gccagtgggt aggctggtgt    7680
ttcacaccac tctgaaatgc aaatctagtt gctgacaaag gccagctgca gagccttagg   7740
gccatagggc agccagtcat ttcctgaggt gtctatttgt ctgtctgcag atggagagat   7800
tctctgcaag gctttggtgt gtttgctgct gctgaaggtc tgttcagcat tgtttccagc   7860
cttaccaagg cttcttgcat ctgtccttca gattcactgt gctggcacac cctggctggc   7920
tcagctccta tcatctgcca cttacggggtt tgcttcagag aaagttgggg tggcttttat   7980
gcagctgcat taaaagaac tactaaactc tgataagatg gctcagctgg taaaagtgcc    8040
tgctgccaag actcacaacc tgtgttcagt cctcaggacc aacatggtga aggtgatag    8100 gttatttctc tgccgctagt gaaatgagcc aagttgggat atgttaaagg caggtttatt   8160
gggaagctgc tcttaggtga gttcacagac ccggaggatt gagggcaggg cagttgccat   8220
ggggggaaga ggggaggtga gggagaatag aaagcgagaa aggggcaca gatgtcccga   8280 cccgcaggac ccagttattc aggggtctg agggagacct tgcctgaaag agaaacgggc   8340
gggaaataag agacagacca agtagatcca tcaaggtctg tttattgaga gtaaggttac   8400
agaatataag cggcaaggag gaaggaagta aagagggaga aacttgcccg tgcctcagcc   8460
cgcaggcagg ggtggttctg cacaactgcc cgggaaggtg ctatctactc ttagctcagg   8520
ggacattctg tgtttttca cagaaagttt gcagatacta ttatctgccc ttgatgttgt    8580
gtcagctgtc atttcaaaag gtcggaagtc tctcctccag gagggagcgg aactttggct   8640
tatgactcag tgtcagtccc caacatctct caaaaggtcc gaagtttctc acgaaggaag   8700
gggagctttg gcttatggct caatgccggt ctccaacaca gagagagaag agaaggaaca   8760
gaaggaagag agaaagagac caaatgtct ggatcacata gggaagaacc tctgggaaaa    8820
aggcagccca gccctgggc tggaaagttc agggtgggag gcagggtatg tcaggtaggg    8880
actgggggat gctgggagat ccctgaagtc aggtctgctt tgatatgcaa actatgcacc   8940
ttgtcccggt cccaaaccaa aagggagaga actaactctg gcgtgagagg gcatgtgccg   9000
catatcacac acacacacac acacacacac acacacacac acacacacac acacacacac   9060
aaaaccatgc acgctcgcac acgatagata atacatacac caatatctga aaagagaaaa   9120
ggttctagtg gtcaggacag agaatgaaaa cggcaggaag gcaagaaagt ttgagaacgt   9180
agggggtggg gtaggagac actacgagtg gaataagcca cgtttggaga acgtctaggc   9240
agatacagaa atgcagaaca cagagagacc gagaccagag cagcgtcaga ccggctgcaa   9300
ggctcttgtt aggggcttta gaaacacctg tgtgctctcc cggaagcctg gtgcagtcag   9360
agaggaagct tgcttcccag acagagatga cacagtttca caacctgtca gaccaccttg   9420
caggagagac tgaaccccag caaccagaac cacttggcta tgcatgtcct tttctgttta   9480
aacctaagtc tctgaagacc gaccagggga gtccctggac ttctttgttc ctcttctcgg   9540
ggtggcggga ctgattgtgt aaatctctta tctccaactt tcactcttat ctgtctcttt   9600
aatcggcata ttgaggatga gtggccaagc ttattggtgt tgctgggtca gacaatttaa   9660
aggcagtcta ggggagaagc agacccaggg agtcagagag gcagagagag aagagagccc   9720
ttcctccact ctcaagctct ggagggggtc tctgccctca ccctcatccc tccccagaat   9780
ccttaaatcc tctagactgt agctctgatt ttacagctgt cacagactcg tcctactagc   9840
cagaggttgg ctcaggtaag caccactggg gaggtagcct agggtgcgct ggggtgggtc   9900
```

```
cagaggaaga gctgcccaga actgtggggg aaggagcggg accgaccatc aacaggggga    9960
cttttcaggg agaatgagag caatcctctg gaggcctggg agaggctgct gagttgctgg   10020
tgcgcgagtc accaactttt cctgcgctct cggtgtccgg ccagaatccc gaagtggcag   10080
ctgagcacgg ggtggcagct tcgtccgcca gcggccggga tcc                     10123
```

RESTORATION OF VISUAL RESPONSES BY IN VIVO DELIVERY OF RHODOPSIN NUCLEIC ACIDS

STATEMENT OF RIGHTS TO INVENTIONS MADE UNDER FEDERALLY SPONSORED RESEARCH

This invention was funded in part by grants from the National Institutes of Health grants (EY12180, EY-04068, EY16087, EY17130 and EY11522) which provides to the United States government certain rights in this invention.

REFERENCE TO A SEQUENCE LISTING SUBMITTED ELECTRONICALLY VIA EFS-WEB

The content of the electronically submitted substitute sequence listing (Name: 052522-504C03US_SequenceListing.txt, Size 43,772 bytes; and Date of Creation: Nov. 27, 2019) is herein incorporated by reference in its entirety.

BACKGROUND OF THE INVENTION

Field of the Invention

The present invention in the field of molecular biology and medicine relates to the use of microbial-type rhodopsins, such as the light-gated cation-selective membrane channel, channelrhodopsin-2 (Chop2) to convert inner retinal neurons to photosensitive cells in photoreceptor-degenerated retina, thereby restoring visual perception and various aspects of vision.

Description of the Background Art

Vision normally begins when rods and cones, also called photoreceptors, convert light signals to electrical signals that are then relayed through second- and third-order retinal neurons and the optic nerve to the lateral geniculate nucleus and, then to the visual cortex where visual images are formed (Baylor, D, 1996, *Proc. Natl. Acad. Sci. USA* 93:560-565; Wässle, H, 2004, *Nat. Rev. Neurosci.* 5:747-57). For a patient who is vision-impaired due to the loss of photoreceptors, visual perception may be induced by providing electrical stimulation at one of these downstream neuronal locations, depending on the nature of the particular impairment.

The severe loss of photoreceptor cells can be caused by congenital retinal degenerative diseases, such as retinitis pigmentosa (RP) (Sung, C H et al., 1991, *Proc. Natl. Acad. Sci. USA* 88 :6481-85; Humphries, P et al., 1992, *Science* 256:804-8; Weleber, R G et al., in: S J Ryan, Ed, Retina, Mosby, St. Louis (1994), pp. 335-466), and can result in complete blindness. Age-related macular degeneration (AMD) is also a result of the degeneration and death of photoreceptor cells, which can cause severe visual impairment within the centrally located best visual area of the visual field.

Both rodents and humans go progressively blind because, as rods and cones are lost, there is little or no signal sent to the brain. Inherited retinal degenerations that cause partial or total blindness affect one in 3000 people worldwide. Patients afflicted with Usher's Syndrome develop progressive deafness in addition to retinal degeneration. There are currently no effective treatments or cures for these conditions.

Basic research on approaches for retinal degeneration has long been classified into two approaches: (1) treatments to preserve remaining photoreceptors in patients with retinal degenerative disease, and (2) methods to replace photoreceptors lost to retinal degeneration. Patients afflicted with retinal disease often group themselves into those seeking ways to slow the loss of their diminishing vision and those who are already legally blind ("no light perception"), having lost their photoreceptors because of an inherited eye disease or trauma.

For the first approach, neuroprotection with neurotrophic factors (LaVail, M M et al., 1992, *Proc. Natl. Acad. Sci. USA* 89:11249-53) and virus-vector-based delivery of wild-type genes for recessive null mutations (Acland, GM et al., 2001, *Nat. Genet.* 28:92-95) have come the furthest—to the point of a Phase I/II clinical trial (Hauswirth, W W, 2005, Retina 25, S60; Jacobson, S, Protocol #0410-677, World Wide Web URL: webconferences.com/nihoba/16_jun_2005.html) gaining approval in the U.S. for adeno-associated viral (AAV)-mediated gene replacement therapy for Leber's Congenital Amaurosis (LCA), a specific form of retinal degeneration. Unfortunately, for patients in advanced stages of retinal degeneration, this approach is not applicable, and the photoreceptor cells must be replaced.

For replacement, one approach involves transplantation (replacement) of normal tissues or cells to the diseased retina. Another involves electrical-stimulation of remaining non-visual neurons via retinal implants in lieu of the lost photoreceptive cells (prosthetic substitution). However, both methods face many fundamental obstacles. For example, for successful transplantation, the implanted tissue or cells must integrate functionally within the host retina. The electrical-stimulation approaches are burdened with mechanistic and technical difficulties as well as problems related to lack of long-term biocompatibility of the implanted bionic devices. In summary, there exist no effective vision-restoring therapies for inherited blinding disease.

The present inventors' strategy as disclosed herein, requires a suitable molecular "light-sensor." Previous studies reported the heterologous expression of *Drosophila* rhodopsin (Zemelman, B V et al., 2002, Neuron 33:15-22) and, more recently, melanopsin, the putative photopigment of the intrinsic photosensitive retinal ganglion cells (Melyan, Z. et al., 2005, *Nature* 433:741-5; Panda, S. et al., 2005, *Science* 307:600-604; Qiu, X. et al., 2005, *Nature* 433:745-9). These photopigments, however, are coupled to membrane channels via a G protein signaling cascade and use cis-isoforms of retinaldehyde as their chromophore. As a result, expression of multiple genes would be required to render photosensitivity. In addition, their light response kinetics is rather slow. Recent studies aimed to improve the temporal resolution described the engineering of a light-sensitive $K^+$ channel (Banghart et al., 2004, Nat. Neurosci. 7:1381-6), though this required introduction of an exogenous "molecular tether" and use of UV light to unblock the channel. This engineered channel was proposed to be potentially useful for restoring light sensitivity in degenerate retinas, but its expression and function in retinal neurons remain unknown.

The present invention makes use of microbial-type rhodopsins similar to bacteriorhodopsin (Oesterhelt, D et al., 1973, *Proc. Natl. Acad. Sci. USA* 70:2853-7), whose conformation change is caused by reversible photoisomerization of their chromophore group, the all-trans isoform of retinaldehyde, and is directly coupled to ion movement through the membrane (Oesterhelt, D., 1998, *Curr. Opin. Struct. Biol.* 8:489-500). Two microbial-type opsins, channelopsin-1 and -2 (Chop1 and Chop2), have recently been cloned from *Chlamydomonas reinhardtii* (Nagel, G. et al., 2002, *Science* 296:2395-8; Sineshchekov, O A et al., 2002, *Proc. Natl. Acad. Sci. USA* 99:8689-94; Nagel, G. et al., 2003, *Proc. Natl. Acad. Sci. USA* 100, 13940-45) and shown to form directly light-gated membrane channels when expressed in *Xenopus laevis* oocytes or HEK293 cells in the presence of all-trans retinal. Chop2, a seven transmembrane domain protein, becomes photo-switchable when bound to the chromophore all-trans retinal. Chop2 is particularly attractive because its functional light-sensitive channel, channelrhodopsin-2 (Chop2 retinalidene abbreviated ChR2) with the attached chromophore is permeable to physiological cations. Unlike animal rhodopsins, which only bind the 11-cis conformation, Chop2 binds all-trans retinal isomers, obviating the need for the all-trans to 11-cis isomerization reaction supplied by the vertebrate visual cycle. However, the long-term compatibility of expressing ChR2 in native neurons in vivo in general and the properties of ChR2-mediated light responses in retinal neurons in particular remained unknown until the present invention.

The present strategy is feasible because histological studies, both in animal models of photoreceptor degeneration (Chang, B. et al., 2002, *Vision Res.* 42:517-25; Olshevskaya, E V et al., 2004, *J. Neurosci.* 24:6078-85) and in postmortem patient eyes with almost complete photoreceptor loss due to RP (Santos, A H et al., 1997, *Arch. Ophthalmol.* 115:511-15; Milam, A H et al., 1998, *Prog. Retin. Eye Res.* 17:175-205), reported the preservation of a significant number of inner retinal neurons.

Retinal gene therapy has been considered a possible therapeutic option for man. For example, U.S. Pat. No. 5,827,702 refers to methods for generating a genetically engineered ocular cell by contacting the cell with an exogenous nucleic acid under conditions in which the exogenous nucleic acid is taken up by the cell for expression. The exogenous nucleic acid is described as a retrovirus, an adenovirus, an adeno-associated virus or a plasmid. See, also, WO 00/15822 (Mar. 23, 2000) and WO 98/48097 (Oct. 29, 1998)

Efforts in such gene therapy have focused mainly on slowing down retinal degeneration in rodent models of primary photoreceptor diseases. Normal genes and mutation-specific ribozymes delivered to photoreceptors have prolonged the lifetime of these cells otherwise doomed for apoptotic cell death (Bennett, J., et al. 1996 *Nat. Med.* 2, 649-54; Bennett, J., et al. 1998, *Gene Therapy* 5, 1156-64; Kumar-Singh, R et al., 1998 *Hum. Mol. Genet.* 7, 1893-900; Lewin, A S et al. 1998, *Nat. Med.* 4, 967-71; Ali, R et al. 2000, *Nat. Genet.* 25, 306-10; Takahashi, M. et al., 1999, *J Virol.* 73, 7812-6; Lau, D., et al., 2000, *Invest. Ophthalmol. Vis. Sci.* 41, 3622-33; and LaVail, M M, el al. 2000, *Proc Natl Acad Sci USA* 97, 11488-93).

Retinal gene transfer of a reporter gene, green fluorescent protein (GFP), using a recombinant adeno-associated virus (rAAV) was demonstrated in normal primates (Bennett, J et al. 1999 *Proc. Natl. Acad. Sci. USA* 96, 9920-25). However, the restoration of vision in a blinding disease of animals, particularly in humans and other mammals, caused by genetic defects in retinal pigment epithelium (RPE) and/or photoreceptor cells has not been achieved. Jean Bennett and colleagues have described the rescue of photoreceptors using gene therapy in a model of rapid degeneration of photoreceptors using mutations of the RP65 gene and replacement therapy with the normal gene to replace or supplant the mutant gene. See, for example, US Patent Publication 2004/0022766 of Acland, Bennett and colleagues. This therapy showed some success in a naturally-occurring dog model of severe disease of retinal degenerations—the RPE65 mutant dog, which is analogous to human LCA.

Advantages of the present approach include the fact that it does not require introducing exogenous cells and tissues or physical devices, thus avoiding many obstacles encountered by existing approaches; the present invention is applicable for the reversal of vision loss or blindness caused by many retinal degenerative diseases. By expressing photosensitive membrane-channels or molecules in surviving retinal neurons of the diseased retina by viral based gene therapy method, the present invention can produce permanent treatment of the vision loss or blindness with high spatial and temporal resolution for the restored vision.

To the extent that any specific disclosure in the aforementioned publications or other publications may be considered to anticipate any generic aspect of the present invention, the disclosure of the present invention should be understood to include a proviso or provisos that exclude of disclaim any such species that were previously disclosed. The aspects of the present invention which are not anticipated by the disclosure of such publications are also unobvious from the disclosure of these publications, due at least in part to the unexpectedly superior results disclosed or alleged herein.

SUMMARY OF THE INVENTION

The present invention is directed to the genetic conversion of surviving light-insensitive inner retinal neurons in a retina in which photoreceptors are degenerating or have already died, into directly photosensitive neuronal cells, thereby imparting light sensitivity to such retinas and restoring one or more aspects of visual responses and functional vision to a subject suffering from such degeneration. By restoring light sensitivity to a retina lacking this capacity, due to disease, the invention provides a mechanism for the most basic light-responses that are required for vision. Said another way, the present invention introduces a "light sensors" into retinal neurons that normally do not have them, to compensate for loss of retinal photoreceptor cells. The present inventors and colleagues investigated the feasibility of using Chop2/ChR2 to restore light sensitivity to the retinas that have undergone rod and cone degeneration. The results presented herein show long-term expression of Chop2/ChR2 in rodent inner retinal neurons in vivo. The results also show that these inner retinal neurons can express a sufficient number of functional ChR2 channels to produce robust membrane depolarization or action potential firing without an exogenous supply of all-trans retinal. Furthermore, the present inventors demonstrated that the expression of ChR2 in a photoreceptor-deficient mouse model not only enables retinal ganglion cells to encode light signals but also restores visually evoked responses in the visual cortex.

The present invention is directed to the restoration of vision loss to individuals that have lost vision or are blind as a result of retinal photoreceptor degeneration. The invention enables retinal neurons in such a diseased retina to respond to light by expressing photosensitive membrane-channels or molecules in these retinal neurons. Preferred the light-sensitive channels or molecules are microbial type light-gate channel rhodopsins, such as ChR2, ChR1, light-driven ion pump, such as bacteriorhodopsins (Lanyi, J K, 2004, *Annu Rev Physiol.* 66:665-88), halorhodopsins (Lanyi, J K, 1990, *Physiol Rev.* 70:319-30), and their derivatives As discovered by the present inventors, retinal neurons that are normally not light sensitive (directly) in the retinas of blind mice, such as retinal ganglion cells (RGCs) and bipolar cells, can respond to light when a green algae protein called channelrhodopsin-2 (ChR2), or a biologically active fragment or a conservative amino acid substitution variant thereof, is inserted into the neuronal cell membranes. The study was conducted with mice that had been genetically bred to lose rods and cones, the light-sensitive cells in the retina, a condition that models RP in humans. In addition to RP, there are many forms of retinal degenerative eye diseases that possibly could be treated by the present approach.

As disclosed herein, visual function can be restored by conveying light-sensitive properties to other surviving cells in the retina after the rods and cones have died. Using a DNA transfer approach, the present inventors introduced the light-absorbing protein ChR2 into the mouse retinal neurons that survived after the rods and cones had died. These cells became light sensitive and sent signals via the optic nerve and higher order visual pathways to the visual cortex where visual perception occurs. Using electrophysiologic means, it was shown that the signals reached the visual cortex in a majority of the ChR2-treated mice. The light sensitivity persisted for at least six months, suggesting that the subject might regain usable vision with additional maneuvers disclosed herein, such as expressing ChR2 in other types of retinal cells or modifying the light sensitivity and/or wavelength selectivity of ChR2, or using similar microbial proteins, to produce diverse light-sensitive channels to improve outcomes for the restoration of normal vision.

As noted by persons of skill in this art, this strategy represents a "paradigm shift in the field" referring to a "new field of re-engineering retinal interneurons as genetically modified 'prosthetic' cells," The present invention "opened the possibility of genetically modifying the surviving retinal interneurons to function as a replacement light-sensing receptor," (Flannery, J and Greenberg, K., 2006, Neuron. 50:1-3; written as a preview to a publication in the same issue of the present inventors and colleagues, Bi J. et al., Neuron 50, 23-33, 2006).

The present inventors capitalized upon advancements in the field by using viral vectors to transfer genes to retinal photoreceptor cells (Flannery J G et al., 1997, Proc. Natl. Acad. Sci. USA 94:6916-21). The conversion of light-insensitive retinal interneurons into photosensitive cells introduces an entirely new direction for treatments of blinding retinal degeneration.

In one embodiment of the present invention, retinal bipolar cells, certain amacrine cells and ganglion cells are targeted for transduction of the Chop2 DNA, to convert them functionally into photosensitive cells that subsume the function of rods and cones. The layering of cells in the retina is such that photoreceptor cells excite bipolar cells which excite ganglion cells to transmit signals to the visual cortex. It is preferred to express the channel opsin of the present invention in bipolar ON-type cells. Intravitreal and/or subretinal injections are used to deliver DNA molecules and virus vectors to reach the cells being targeted.

In one embodiment, the promoter is from a mGluR6 promoter-region of the Grm6 gene (GenBank accession number BC041684), a gene that controls expression of metabotropic glutamate receptor 6 ((Ueda Y et al., 1997, J Neurosc 17:3014-23). The genomic sequence is shown in GenBank accession number—AL627215. A preferred example of this promoter region sequence from the above GenBank record is SEQ ID NO:9 consisting of 11023 nucleotides.

The original Umeda el al., study employed a 10 kb promoter, but the actual length of the promoter and the sequence that comprises control elements of Grm6 can be adjusted by increasing or decreasing the fragment length. It is a matter of routine testing to select and verify the action of the optimally sized fragment from the Grm6 gene that drives transgenic expression of a selected coding sequence, preferably Chop2, in the desired target cells, preferably in bipolar cells which are rich in glutamate receptors, particularly the "on" type bipolar cells, which are the most bipolar cells in the retina (Nakajima, Y., el al., 1993, J Biol Chem 268:11868-73).

The present invention is directed to a method of restoring light sensitivity to a retina, comprising:
(a) delivering to retinal neurons a nucleic acid expression vector that encodes a light-gated channel rhodopsin or a light-driven ion pump rhodopsin expressible in the neurons, which vector comprises an open reading frame encoding the rhodopsin, and operatively linked thereto, a promoter sequence, and optionally, transcriptional regulatory sequences; and
(b) expressing the vector in the neurons, thereby restoring light sensitivity.

The rhodopsin is preferably channelrhodopsin-2 (Chop2) or a biologically active fragment or conservative amino acid substitution variant thereof.

The vector is preferably a rAAV viral vector.

The promoter may be a constitutive promoter such as a hybrid CMV enhancer/chicken β-actin promoter (CAG) (as indicated below as part of SEQ ID NO:1), or a CMV promoter. The promoter may also be (i) an inducible or (ii) a cell type-specific promoter, preferred examples of the latter being the mGluR6 promoter (e.g., part of a promoter sequence SEQ ID NO:9), a Pcp2 (L7) promoter or a neurokinin-3 (NK-3) promoter.

A preferred vector in the above method comprises the CAG promoter, a woodchuck posttranscriptional regulatory element (WPRE), and a bovine or human growth hormone polyadenylation sequence.

In the present method, the retinal neurons are selected from ON- and OFF-type retinal ganglion cells, retinal rod bipolar cells, AII amacrine cells and ON and OFF retinal cone bipolar cells. Preferably, the vector is targeted to and expressed in ON type ganglion cells and/or ON type bipolar cells If the vector comprises the NK-3 promoter, the vector is preferably targeted to OFF cone bipolar cells.

The invention is also directed to method of restoring photosensitivity to retinal neurons of a subject suffering from vision loss or blindness in whom retinal photoreceptor cells are degenerating or have degenerated and died, which method comprises:
(a) delivering to the retina of the subject a nucleic acid vector that encodes a light-gated channel rhodopsin or a light-driven ion pump rhodopsin expressible in the neurons, which vector comprises an open reading frame encoding the rhodopsin, and operatively linked thereto, a promoter sequence, and optionally, transcriptional regulatory sequences;
(b) expressing the vector in the neurons, wherein the expression of the rhodopsin renders the neurons photosensitive, thereby restoring of photosensitivity to the retina.

In this method the rhodopsin is preferably Chop2 or a biologically active fragment or conservative amino acid substitution variant thereof. The vector is preferably a rAAV viral vector. Preferred promoters are as described above for the above-presented embodiment. Preferred target cells for the vector are as described above.

The restoration of photosensitivity using the above method preferably results in restoration of vision in the subject. The vision is preferably measured by one or more of the following methods:
(i) a light detection response by the subject after exposure to a light stimulus
(ii) a light projection response by the subject after exposure to a light stimulus;
(iii) light resolution by the subject of a light versus a dark patterned visual stimulus;
(iv) electrical recording of a response in the visual cortex to a light flash stimulus or a pattern visual stimulus In this foregoing method, the vision loss or blindness may be a result of a degenerative disease, preferably, retinitis pigmentosa or age-related macular degeneration.

In another embodiment, the subject is also provided with a visual prosthesis before, at the same time as, or after delivery of the vector. Preferred visual prostheses comprise retinal implants, cortical implants, lateral geniculate nucleus implants, or optic nerve implants.

When employing the foregoing method, the subject's visual response may be subjected to training using one or more visual stimuli.. The training is preferably achieved by one or more of the following methods:
(a) habituation training characterized by training the subject to recognize (i) varying levels of light and/or pattern stimulation, and/or (ii) environmental stimulation from a common light source or object; and
(b) orientation and mobility training characterized by training the subject to detect visually local objects and move among the objects more effectively than without the training.

BRIEF DESCRIPTION OF DRAWINGS

FIGS. 1A-1I. Expression of Chop2-GFP in Retinal Neurons In vivo. FIG. 1A shows the rAAV-CAG-Chop2-GFP-WPRE expression cassette. CAG: a hybrid CMV enhancer/chicken β-actin promoter. WPRE: woodchuck posttranscriptional regulatory element. BGHpA: a bovine growth hormone polyadenylation sequence. (FIGS. 1B and 1C) Chop2-GFP fluorescence viewed in low (FIG. 1B) and high (FIG. 1C) magnifications from eyes two months after the viral vector injection. (FIG. 1D) Confocal images of a ganglion cell, which show a stacked image (left) and a single optical section image (right). (FIG. 1E) Chop2-GFP fluorescence in a horizontal cell, which shows GFP in soma, axon, and distal axon terminal. (FIGS. 1F and 1G) Chop2-GFP fluorescence in amacrine cells (FIG. 1F) and a retinal bipolar cell (FIG. 1G). FIGS. 1H and 1I show fluorescence image (FIG. 1H) and phase contrast image (FIG. 1I) taken from a retina 12 months after the injection of Chop2-GFP viral vectors. Images in (FIGS. 1B-1E) were taken from flat whole-mounts of rat retinas. Images in (FIGS. 1F-1I) were taken from vertical slice sections of rat retinas. Scale bar: 200 μm in (FIG. 1B); 100 μm in (FIG. 1C); 15 μm in (FIG. 1D); 50 μm in (FIG. 1E), FIG. 1H), and (FIG. 1I); 25 μm in (FIG. 1F) and (FIG. 1G). ONL: outer nuclear layer; INL: inner nuclear layer; IPL: inner plexiform layer; GCL:

(FIG. 2A) Phase contrast image (left) and fluorescence image (right) of a GFP-positive retinal neuron dissociated from the viral vector injected eye. Scale bar: 25 μm. (FIG. 2B) A recording of Chop2-GFP fluorescent retinal cell to light stimuli of wavelengths ranging from 420 to 580 nm. The light intensities were ranging from $1.0$–$1.6\times10^{18}$ photons $cm^{-2}$ $s^{-1}$. (FIG. 2C) A representative recording of the currents elicited by light stimuli at the wavelength of 460 nm with light intensities ranging from $2.2\times10^{15}$ to $1.8\times10^{18}$ photons $cm^{-2}$ $s^{-1}$. (FIG. 2D) Current traces after the onset of the light stimulation from FIG. 2C shown in the expanded time scale. The line shows the fitting of one current trace by an exponential function: $I_{(t)}=a_0+a_1\times(1-\exp[-t/\tau_1])+a_2\times(\exp[-t/\tau_2])$, in which $\tau_1$ and $\tau_2$ represent the activation and inactivation time constant, respectively. (FIG. 2E) Current traces after the termination of the light stimulation from FIG. 2C shown in the expanded time scale. The line shows the fitting of one current trace by a single exponential function: $I_{(t)\ 0}=a_0+a_1\times(\exp[-t/\tau])$, in which $\tau$ represent the deactivation time constant. (FIG. 2F) Light-intensity response curve. The data points were fitted with a single logistic function curve. (FIGS. 2F and H) The relationships of light-intensity and activation time constant (FIG. 2G) and light-intensity and inactivation time constant (FIG. 2H) obtained from the fitting shown in FIG. 2D. All recordings were made at the holding potential of −70 mV. The data points in FIG. 2F-2H are shown as mean±SD (n=7).

(FIG. 3A) A representative recordings from GFP-positive nonspiking neurons. The voltage responses were elicited by four incremental light stimuli at the wavelength of 460 nm with intensities ranging from $2.2\times10^{15}$ to $1.8\times10^{18}$ photons $cm^{-2}$ $s^{-1}$ in current clamp. The dotted line indicates the saturated potential level. (FIG. 3B) A representative recording from GFP-positive nonspiking neurons to repeat light stimulations. The light-evoked currents (top traces) and voltage responses (bottom traces) from a same cells were shown. Left panel shows the superimposition of the first (red) and second (black) traces in an expanded time scale. The dotted line indicates the sustained component of the currents (top) and plateau membrane potential (bottom). (FIG. 3C) A representative recording of GFP-positive spiking neurons to repeated light stimulations. The responses in FIG. 3B and 3C were evoked by light at the wavelength of 460 nm with the intensity of $1.8\times10^{18}$ photons $cm^{-2}$ $s^{-1}$.

FIGS. 4A-4I. Expression and Light-Response Properties of ChR2 in Retinal Neurons of rd1/rd1 Mice. (FIG. 4A) Chop2-GFP fluorescence viewed in flat retinal whole-mount of a 15 month old mouse with the Chop2-GFP viral vector injection at 9 months of age. (FIG. 4B) Chop2-GFP fluorescence viewed in vertical section from the retina of a 6 month old mouse with the injection of Chop2-GFP viral vectors at 3 months of age. (FIG. 4C) Light microscope image of a semithin vertical retinal section from a 5 month old mouse (Chop2-GFP viral vectors injected at postnatal day 1). Scale bar: 50 μm in (FIG. 4A) and 30 μm in (FIGS. 4B and 4C). (FIGS. 4D-4E) show representative recordings of transient spiking (FIG. 4D) and sustained spiking (FIG. 4E) GFP-positive neurons. The responses were elicited by light of four incremental intensities at the wavelength of 460 nm. The light intensity without neutral density (Log I=0) was $3.6\times10^{17}$ photons $cm^{-2}$ $s^{-1}$. The currents were recorded at the holding potential of −70 mV. The superimposed second (solid black) and fourth (dashed or red) current and voltage traces are shown in the right panel in the expanded time scale. (FIGS. 4F-4I) show the relationships of the amplitude of current (FIG. 4F), membrane depolarization (FIG. 4G), the number of spikes (FIG. 4H), and the time to the first spike peak (FIG. 4I) to light intensity. Recordings were made from rd1/rd1 mice at >4 months of age. The data points are the mean±SE (n=6 in FIG. 4F-4H and n=4 in FIG. 4I).

FIG. 5A-5D. Multielectrode Array Recordings of the ChR2-Expressing Retinas of rd1/rd1 Mice. (FIG. 5A) A sample recording of light-evoked spike activities from the retinas of rd1/rd1 mice (ages ≥4 months). The recording was made in the present of CNQX (25 µM) and AP5 (25 µM). Prominent light-evoked spike activity was observed in 49 out of 58 electrodes (electrode 15 was for grounding and electrode 34 was defective). (FIG. 5B) Sample light-evoked spikes recorded from a single electrode to three incremental light intensities. (FIG. 5C) The raster plots of 30 consecutive light-elicited spikes originated from a single neuron. (FIG. 5D) The averaged spike rate histograms. The light intensity without neutral density filters (Log I=0) was $8.5 \times 10^{17}$ photons $cm^{-2} s^{-1}$. The responses shown in FIG. 5A were elicited by a single light pulse without neutral density filters.

(FIG. 6A) GFP labeled terminal arbors of retinal ganglion cells in ventral lateral geniculate nucleus and dorsal lateral geniculate nucleus. (FIG. 6B) GFP-labeled terminal arbors of retinal ganglion cells in superior colliculus. OT: optical track; vLGN: ventral lateral geniculate nucleus; dLGN: dorsal lateral geniculate nucleus; SC: superior colliculus. Scale bar: 200 µm in FIG. 6A), 100 µm in FIG. 6B). (FIG. 6C) VEPs recorded from a wild-type mouse. The responses were observed both to the wavelengths of 460 and 580 nm. (FIG. 6D) VEPs recorded from an rd1/rd1 mouse injected with Chop2-GFP viral vectors. The responses were elicited only by light at the wavelength of 460 nm but not at the wavelength of 580 nm. (FIG. 6E) No detectable VEPs were observed from rd1/rd1 mice injected with viral vectors carrying GFP alone. The light intensities measured at the corneal surface at the wavelengths of 460 and 580 nm were $5.5 \times 10^{16}$ and $5.2 \times 10^{16}$ photons $cm^{-2} s^{-1}$, respectively.

DETAILED DESCRIPTION OF THE INVENTION

Figure 2A:
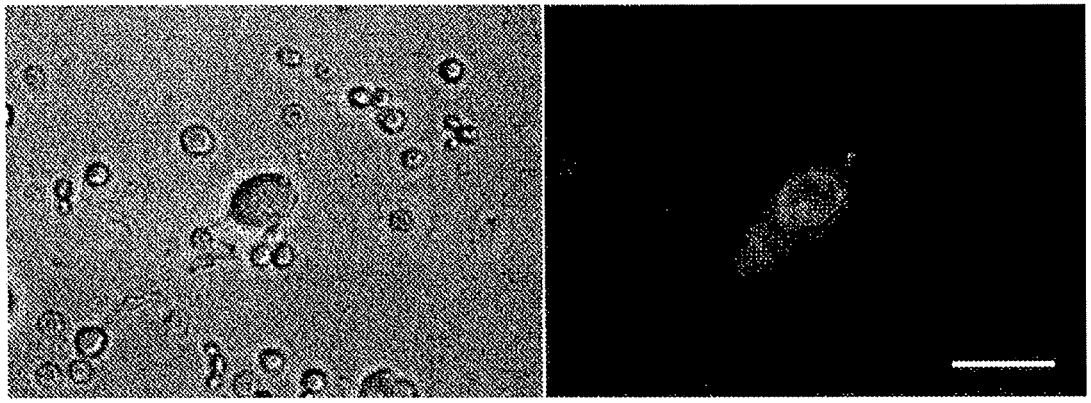
FIGS. 2A-2H. Properties of Light-Evoked Currents of the ChR2-expressing retinal neurons.

The invention provides a method for treating an ocular disorder in a human, other mammalian or other animal subject. In particular, the ocular disorder is one which involves a mutated or absent gene in a retinal pigment epithelial cell or a photoreceptor cell. The method of this invention comprises the step of administering to the subject by intravitreal or subretinal injection of an effective amount of a recombinant virus carrying a nucleic acid sequence encoding an ocular cell-specific normal gene operably linked to, or under the control of, a promoter sequence which directs the expression of the product of the gene in the ocular cells and replaces the lack of expression or incorrect expression of the mutated or absent gene.

Ocular Disorders

The ocular disorders for which the present methods are intended and may be used to improve one or more parameters of vision include, but are not limited to, developmental abnormalities that affect both anterior and posterior segments of the eye. Anterior segment disorders include glaucoma, cataracts, corneal dystrophy, keratoconus. Posterior segment disorders include blinding disorders caused by photoreceptor malfunction and/or death caused by retinal dystrophies and degenerations. Retinal disorders include congenital stationary night blindness, age-related macular degeneration, congenital cone dystrophies, and a large group of retinitis-pigmentosa (RP)-related disorders. These disorders include genetically pre-disposed death of photoreceptor cells, rods and cones in the retina, occurring at various ages. Among those are severe retinopathies, such as subtypes of RP itself that progresses with age and causes blindness in childhood and early adulthood and RP-associated diseases, such as genetic subtypes of LCA, which frequently results in loss of vision during childhood, as early as the first year of life. The latter disorders are generally characterized by severe reduction, and often complete loss of photoreceptor cells, rods and cones. (Trabulsi, E I, ed., *Genetic Diseases of the Eye*, Oxford University Press, NY, 1998).

In particular, this method is useful for the treatment and/or restoration of at least partial vision to subjects that have lost vision due to ocular disorders, such as RPE-associated retinopathies, which are characterized by a long-term preservation of ocular tissue structure despite loss of function and by the association between function loss and the defect or absence of a normal gene in the ocular cells of the subject. A variety of such ocular disorders are known, such as childhood onset blinding diseases, retinitis pigmentosa, macular degeneration, and diabetic retinopathy, as well as ocular blinding diseases known in the art. It is anticipated that these other disorders, as well as blinding disorders of presently unknown causation which later are characterized by the same description as above, may also be successfully treated by this method. Thus, the particular ocular disorder treated by this method may include the above-mentioned disorders and a number of diseases which have yet to be so characterized.

Visual information is processed through the retina through two pathways: an ON pathway which signals the light ON, and an OFF pathway which signals the light OFF (Wässle, supra). It is generally believed that the existence of the ON and OFF pathway is important for the enhancement of contrast sensitivity. The visual signal in the ON pathway is relay from ON-cone bipolar cells to ON ganglion cells. Both ON-cone bipolar cells and ON-ganglion cells are depolarized in response to light. On the other hand, the visual signal in the OFF pathway is carried from OFF-cone bipolar cells to OFF ganglion cells. Both OFF-cone bipolar cells and OFF-ganglion cells arc hypopolarized in response to light. Rod bipolar cells, which are responsible for the ability to see in dim light (scotopic vision), are ON bipolar cells (depolarized in response to light). Rod bipolar cells relay the vision signal through AII amacrine cells (an ON type retinal cells) to ON an OFF cone bipolar cells.

The present Examples show functional consequence of expressing ubiquitously expressing light sensitive channels, namely ChR2, in retinal ganglion cells by CAG promoter, and suggest that this sufficient for restoring useful vision. However, targeting of depolarizing membrane channels, such as ChR2, to the ON-type retinal neurons might result in better useful vision. In addition, expression of light sensors in more distal retinal neurons, such as bipolar cells, would utilize the remaining signal processing functions of the degenerate retina. Furthermore, by expressing a depolarizing light sensor, such as ChR2, in ON type retinal neurons (ON type ganglion cells and/or ON type bipolar cells) and expressing a hypopolarizing light sensor, such as halorhodopsin (a chloride pump) (Han, X et al., 2007, *PLoS ONE*, Mar 21;2:e299; Zhang, F et al., 2007; *Nature* 446: 633-9; present inventors' results) in OFF type retinal neurons (OFF type ganglion cells and/or OFF type bipolar cells) could create ON and OFF pathways in photoreceptor degenerated retinas.

An alternative approach to restore ON and OFF pathways in the retina is achieved by, expressing a depolarizing light sensor, such as ChR2, to rod bipolar cells or AII amacrine. This is because the depolarization of rod bipolar cells or AII amacrine cells can lead to the ON and OFF responses at the levels of cone bipolar cells and the downstream retinal ganglion cells and, thus, the ON and OFF pathways that are inherent in the retina could be maintained (Wässle, 2004).

According to the present invention, the followings approaches are used to restore the light sensitivity of inner retinal neurons:

(1) Ubiquitously expressing light sensitive channels, such as ChR2, are employed to produced membrane depolarization in all types of ganglion cells (both ON and OFF ganglion cells), or all types of bipolar cells (rod bipolar cells, and ON and OFF cone bipolar cells). The AAV vector with CAG promoter has already partially achieved this approach in rodent retinas, as exemplified herein.

(2) A depolarizing light sensor, such as ChR2, is targeted to ON type retinal neurons such as ON type ganglion cells or ON type bipolar cells. A study from Dr. J. G. Flannery's group has identified the fragments of a human gap junctional protein (connexin-36) promoter to target GFP in ON-type retinal ganglion cells by using AAV-2 virus vector (Greenberg K P et al., 2007, *In vivo Transgene Expression in ON-Type Retinal Ganglion Cells: Applications to Retinal Disease. ARVO abstract*, 2007). A readily packable shorter version of mGluR6 promoter of (<2.5 kb) would allow targeting of ChR2 to ON type bipolar cells (both rod bipolar cells and ON type cone bipolar cells).

(3) Cell specific promoters are used to target the specific types of retinal neurons. A promoter that could target rod bipolar cells is Pcp2 (L7) promoter (Tomomura, M et al., 2001, *Eur J Neurosci.* 14:57-63). The length of the active promoter is preferably less that 2.5 Kb so it can be packaged into the AAV viral cassette. (4) A depolarizing light sensor, such as ChR2, is targeted to ON type ganglion cells or ON type cone bipolar cells and a hypopolarizing light sensor, such as halorhodopsin, to OFF type ganglion cells or OFF type cone bipolar cells to create ON and OFF pathways. As described above, an adequately short (packable) version of mGluR6 promoter (<2.5 kb) would allow targeting of ChR2 to ON type bipolar cells. The Neurokinin-3 (NK-3) promoter would be used to target halorhodopsin to OFF cone bipolar cells (Haverkamp, S et al., 2002, *J Comparative Neurology*, 455:463-76.

Vectors

According to the various embodiments of the present invention, a variety of known nucleic acid vectors may be used in these methods, e.g., recombinant viruses, such as recombinant adeno-associated virus (rAAV), recombinant adenoviruses, recombinant retroviruses, recombinant poxviruses, and other known viruses in the art, as well as plasmids, cosmids and phages, etc. Many publications well-known in the art discuss the use of a variety of such vectors for delivery of genes. See, e.g., Ausubel et al., *Current Protocols in Molecular Biology*, John Wiley & Sons, New York, latest edition; Kay, M A. et al., 2001, *Nat. Med.*, 7:33-40; and Walther W et al., 2000, *Drugs* 60:249-71).

Methods for assembly of the recombinant vectors are well-known. See, for example, WO 00/15822 and other references cited therein, all of which are incorporated by reference.

There are advantages and disadvantages to the various viral vector systems. The limits of how much DNA can be packaged is one determinant in choosing which system to employ. rAAV tend to be limited to about 4.5 kb of DNA, whereas lentivirus (e.g., retrovirus) system can accommodate 4-5 kb.

AAV Vectors

Adeno-associated viruses are small, single-stranded DNA viruses which require a helper virus for efficient replication (Berns, K I, *Parvoviridae: the viruses and their replication*, p. 1007-1041 (vol. 2), in Fields, B N et al., *Fundamental Virology*, 3rd Ed., (Lippincott-Raven Publishers, Philadelphia (1995)). The 4.7 kb genome of AAV has two inverted terminal repeats (ITR) and two open reading frames (ORFs) which encode the Rep proteins and Cap proteins, respectively. The Rep reading frame encodes four proteins of molecular weights 78, 68, 52 and 40 kDa. These proteins primarily function in regulating AAV replication and rescue and integration of the AAV into the host cell chromosomes. The Cap reading frame encodes three structural proteins of molecular weights 85 (VP 1), 72 (VP2) and 61 (VP3) kDa which form the virion capsid (Berns, supra). VP3 comprises >80% of total AAV virion proteins.

Flanking the rep and cap ORFs at the 5' and 3' ends are 145 bp ITRs, the first 125 bp's of which can form Y- or T-shaped duplex structures. The two ITRs are the only cis elements essential for AAV replication, rescue, packaging and integration of the genome. Two conformations of AAV ITRs called "flip" and "flop" exist (Snyder, R O et al., 1993, *J Virol.*, 67:6096-6104; Berns, K I, 1990 *Microbiol Rev*, 54:316-29). The entire rep and cap domains can be excised and replaced with a transgene such as a reporter or therapeutic transgene (Carter, B J, in *Handbook of Parvoviruses*, P. Tijsser, ed., CRC Press, pp. 155-168 (1990)).

AAVs have been found in many animal species, including primates, canine, fowl and human (Murphy, FA et al., *The Classification and Nomenclature of Viruses: Sixth Rept of the Int'l Comme on Taxonomy of Viruses, Arch Virol*, Springer-Verlag, 1995). Six primate serotypes are known (AAV1, AAV2, AAV3, AAV4, AAV5 and AAV6).

The AAV ITR sequences and other AAV sequences employed in generating the minigenes, vectors, and capsids, and other constructs used in the present invention may be obtained from a variety of sources. For example, the sequences may be provided by any of the above 6 AAV serotypes or other AAV serotypes or other densoviruses, including both presently known human AAV and yet to yet-to-be-identified serotypes. Similarly, AAVs known to infect other animal species may be the source of ITRs used in the present molecules and constructs. Capsids from a variety of serotypes of AAV may be combined in various mixtures with the other vector components (e.g., WO01/83692 (Nov. 8, 2001) incorporated by reference). Many of these viral strains or serotypes are available from the American Type Culture Collection (ATCC), Manassas, Va., or are available from a variety of other sources (academic or commercial).

It may be desirable to synthesize sequences used in preparing the vectors and viruses of the invention using known techniques, based on published AAV sequences, e.g., available from a variety of databases. The source of the sequences utilized to prepare the present constructs is not considered to be limiting. Similarly, the selection of the AAV serotype and species (of origin) is within the skill of the art and is not considered limiting The Minigene As used herein, the AAV sequences are typically in the form of a rAAV construct (e.g., a minigene or cassette) which is packaged into a rAAV virion. At minimum, the rAAV minigene is formed by AAV ITRs and a heterologous nucleic acid molecule for delivery to a host cell. Most suitably, the minigene comprises ITRs located 5' and 3' to the heterologous sequence. However, minigene comprising 5' ITR and 3' ITR sequences arranged in tandem, e.g., 5' to 3' or a head-to-tail, or in another configuration may also be desirable. Other embodiments include a minigene with multiple copies of the ITRs, or one in which 5' ITRs (or conversely, 3' ITRs) are located both 5' and 3' to the heterologous sequence. The ITRs sequences may be located immediately upstream and/or downstream of the heterologous sequence; intervening sequences may be present. The ITRs may be from AAV5, or from any other AAV serotype. A minigene may include 5' ITRs from one serotype and 3' ITRs from another.

The AAV sequences used are preferably the 145 bp cis-acting 5' and 3' ITR sequences (e.g., Carter, B J, supra). Preferably, the entire ITR sequence is used, although minor modifications are permissible. Methods for modifying these ITR sequences are well-known (e.g., Sambrook, J. et al., *Molecular Cloning: A Laboratory Manual*, 3$^{rd}$ Edition, Cold Spring Harbor Press, Cold Spring Harbor, NY, 2001; Brent, R et al., eds., *Current Protocols in Molecular Biology*, John Wiley & Sons, Inc., 2003; Ausubel, FM et al., eds., *Short Protocols in Molecular Biology*, 5$^{th}$ edition, Current Protocols, 2002; Carter et al., supra; and Fisher, K et al., 1996 *J Virol.* 70:520-32). It is conventional to engineer the rAAV virus using known methods (e.g., Bennett, J et al. 1999, supra). An example of such a molecule employed in the present invention is a "cis-acting" plasmid containing the heterologous sequence, preferably the Chop2 sequence, flanked by the 5' and 3' AAV ITR sequences.

The heterologous sequence encodes a protein or polypeptide which is desired to be delivered to and expressed in a cell. The present invention is directed to Chop2 sequences under the control of a selected promoter and other conventional vector regulatory components.

The Transgene being Targeted and Expressed

In a most preferred embodiment, the heterologous sequence is a nucleic acid molecule that functions as a transgene. The term "transgene" as used herein refers to a nucleic acid sequence heterologous to the AAV sequence, and encoding a desired product, preferably Chop2 and the regulatory sequences which direct or modulate transcription and/or translation of this nucleic acid in a host cell, enabling expression in such cells of the encoded product. Preferred polypeptide products are those that can be delivered to the eye, particularly to retinal neurons.

The transgene is delivered and expressed in order to treat or otherwise improve the vision status of a subject with an ocular disorder that may result from any of a number of causes, including mutations in a normal photoreceptor-specific gene. The targeted ocular cells may be photoreceptor cells (if not totally degenerated) or, more preferably, other retinal neurons, namely, bipolar cells and retinal ganglion cells.

Using an mGluR6 promoter operatively linked to a Chop2 opsin coding sequence and a reporter gene, e.g., GFP or another fluorescent protein, an insert of about 4.5 kb is preferred—1 kb for the opsin, 0.7 kb for the reporter, 10 kb-for the mGluR6 promoter region and about 0.4 kb for conventional transcriptional regulatory factors.

Use of different opsin genes allows selection of desired wavelengths as the absorption maxima of different channel proteins differ. In one embodiment, the reported gene is moved to the red part of the visual spectrum.

Similarly, based on the studies reported herein, the brightness of the light needed to stimulate evoked potential in transduced mouse retinas, indicates that a channel opsin with increased light sensitivity may be more desirable. This can be achieved by selection of a suitable naturally occurring opsin, for example other microbial-type rhodopsins, or by modifying the light sensitivity of Chop2 as well as its other properties, such as ion selectivity and spectral sensitivity, to produce diversified light-sensitive channels to better fit the need for vision restoration.

Different transgenes may be used to encode separate subunits of a protein being delivered, or to encode different polypeptides the co-expression of which is desired. If a single transgene includes DNA encoding each of several subunits, the DNA encoding each subunit may be separated by an internal ribozyme entry site (IRES), which is preferred for short subunit-encoding DNA sequences (e.g., total DNA, including IRES is <5 kB). Other methods which do not employ an IRES may be used for co-expression, e.g., the use of a second internal promoter, an alternative splice signal, a co- or post-translational proteolytic cleavage strategy, etc., all of which are known in the art.

The coding sequence or non-coding sequence of the nucleic acids useful herein preferably are codon-optimized for the species in which they are to be expressed. Such codon-optimization is routine in the art.

While a preferred transgene encodes a full length polypeptide, preferably Chop2 (SEQ ID NO:6, the present invention is also directed to vectors that encode a biologically active fragment or a conservative amino acid substitution variant of Chop2 (or of any other polypeptide of the invention to be expressed in retinal neurons). Non-limiting examples of useful fragments are the polypeptide with the sequence SEQ ID NO:3 and SEQ ID NO:8. The fragment or variant is expressed by the targets cells being transformed and is able to endow such cells with light sensitivity that is functionally equivalent to that of the full length or substantially full length polypeptide having a native, rather than variant, amino acid sequence. A biologically active fragment or variant is a "functional equivalent"—a term that is well understood in the art and is further defined in detail herein. The requisite biological activity of the fragment or variant, using any method disclosed herein or known in the art to establish activity of a channel opsin, has the following activity relative to the wild-type native polypeptide: about 50%, about 55%, about 60%, about 65%, about 70%, about 75%, about 80%, about 85%, about 90%, about 95%, about 99%, and any range derivable therein, such as, for example, from about 70% to about 80%, and more preferably from about 81% to about 90%; or even more preferably, from about 91% to about 99%.

It should be appreciated that any variations in the coding sequences of the present nucleic acids and vectors that, as a result of the degeneracy of the genetic code, express a polypeptide of the same sequence, are included within the scope of this invention.

The amino acid sequence identity of the variants of the present invention are determined using standard methods, typically based on certain mathematical algorithms. In a preferred embodiment, the percent identity between two amino acid sequences is determined using the Needleman and Wunsch (*J. Mol. Biol.* 48:444-453 (1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of Meyers and Miller (CABIOS, 4:11-17 (1989)) which has been incorporated into the ALIGN program (version 2.0), using a PAM120 weight residue table, a gap length penalty of 12 and a gap penalty of 4. The nucleotide and amino acid sequences of the present invention can further be used as a "query sequence" to perform a search against public databases, for example, to identify other family members or related sequences. Such searches can be performed using the NBLAST and XBLAST programs (Altschul et al. (1990) *J. Mol. Biol.* 215:403-10). BLAST nucleotide searches can be performed with the NBLAST program, score=100, wordlength=12 to obtain nucleotide sequences homologous to, e.g., DAN encoding Chop2 of *C. reinhardtii*. BLAST protein searches can be performed with the XBLAST program, score=50, wordlength=3 to obtain amino acid sequences homologous to the appropriate reference protein such as Chop2. To obtain gapped alignments for comparison purposes, Gapped BLAST can be utilized (Altschul et al. (1997) *Nucleic Acids Res.* 25:3389-3402). When utilizing BLAST and Gapped BLAST programs, the default parameters of the respective programs (e.g.,, XBLAST and NBLAST) can be used. See World Wide Web URL ncbi.nlm.nih.gov.

The preferred amino acid sequence variant has the following degrees of sequence identity with the native, full length channel opsin polypeptide, preferably Chop2 from *C. reinhardtii* (SEQ ID NO:6) or with a fragment thereof (e.g., SEQ ID NO:3 or 8): about 50%, about 55%, about 60%, about 65%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%, and any range derivable therein, such as, for example, from about 70% to about 80%, and more preferably from about 81% to about 90%; or even more preferably, from about 91% to about 99% identity. A preferred biologically active fragment comprises or consists of SEQ ID NO:3, which corresponds to residues 1-315 of SEQ ID NO:6, or comprises or consists of SEQ ID NO:8.

Any of a number of known recombinant methods are used to produce a DNA molecule encoding the fragment or variant. For production of a variant, it is routine to introduce mutations into the coding sequence to generate desired amino acid sequence variants of the invention. Site-directed mutagenesis is a well-known technique for which protocols and reagents are commercially available (e.g., Zoller, M J et al., 1982, *Nucl Acids Res* 10:6487-6500; Adelman, J P et al., 1983, DNA 2:183-93). These mutations include simple deletions or insertions, systematic deletions, insertions or substitutions of clusters of bases or substitutions of single bases.

In terms of functional equivalents, it is well understood by those skilled in the art that, inherent in the definition of a "biologically functional equivalent" protein, polypeptide, gene or nucleic acid, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted.

In particular, the shorter the length of the polypeptide, the fewer amino acids changes should be made. Longer fragments may have an intermediate number of changes. The full length polypeptide protein will have the most tolerance for a larger number of changes. It is also well understood that where certain residues are shown to be particularly important to the biological or structural properties of a polypeptide residues in a binding regions or an active site, such residues may not generally be exchanged. In this manner, functional equivalents are defined herein as those poly peptides which maintain a substantial amount of their native biological activity.

For a detailed description of protein chemistry and structure, see Schulz, G E et al., *Principles of Protein Structure*, Springer-Verlag, New York, 1978, and Creighton, T. E., *Proteins: Structure and Molecular Properties*, W.H. Freeman & Co., San Francisco, 1983, which are hereby incorporated by reference. The types of substitutions that may be made in the protein molecule may be based on analysis of the frequencies of amino acid changes between a homologous protein of different species, such as those presented in Table 1-2 of Schulz et al. (supra) and FIG. 3-9 of Creighton (supra). Based on such an analysis, conservative substitutions are defined herein as exchanges within one of the following five groups:

| 1 | Small aliphatic, nonpolar or slightly polar residues | Ala, Ser, Thr (Pro, Gly); |
| 2 | Polar, negatively charged residues and their amides | Asp, Asn, Glu, Gln; |
| 3 | Polar, positively charged residues | His, Arg, Lys; |
| 4 | Large aliphatic, nonpolar residues | Met, Leu, Ile, Val (Cys) |
| 5 | Large aromatic residues | Phe, Tyr, Trp. |

The three amino acid residues in parentheses above have special roles in protein architecture. Gly is the only residue lacking a side chain and thus imparts flexibility to the chain. Pro, because of its unusual geometry, tightly constrains the chain. Cys can participate in disulfide bond formation, which is important in protein folding.

The hydropathy index of amino acids may also be considered in selecting variants. Each amino acid has been assigned a hydropathy index on the basis of their hydrophobicity and charge characteristics, these are: Ile (+4.5); Val (+4.2); Leu (+3.8); Phe (+2.8); Cys (+2.5); Met (+1.9); Ala (+1.8); Glycine (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). The importance of the hydropathy index in conferring interactive biological function on a proteinaceous molecule is generally understood in the art (Kyte and Doolittle, 1982, *J. Mol. Biol.*

157:105-32). It is known that certain amino acids may be substituted for other amino acids having a similar hydropathy index or score and still retain a similar biological activity. In making changes based upon the hydropathy index, the substitution of amino acids whose hydropathy indices are within ±2 is preferred, those which are within ±1 are particularly preferred, and those within ±0.5 are even more particularly preferred. It is also understood in the art that the substitution of like amino acids can be made effectively on the basis of hydrophilicity, particularly where the biological functional equivalent polypeptide thereby created is intended for use in certain of the present embodiments. U.S. Pat. No. 4,554,101, discloses that the greatest local average hydrophilicity of a proteinaceous molecule, as governed by the hydrophilicity of its adjacent amino acids, correlates with a biological property of the molecule. See U.S. Pat. No. 4,554,101 for a hydrophilicity values. In making changes based upon similar hydrophilicity values, the substitution of amino acids whose hydrophilicity values are within ±2 is preferred, those which are within ±1 are particularly preferred, and those within ±0.5 are even more particularly preferred.

Regulatory Sequences

The minigene or transgene of the present invention includes appropriate sequences operably linked to the coding sequence or ORF to promote its expression in a targeted host cell. "Operably linked" sequences include both expression control sequences such as. promoters that are contiguous with the coding sequences and expression control sequences that act in trans or distally to control the expression of the polypeptide product.

Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance nucleic acid or protein stability; and when desired, sequences that enhance protein processing and/or secretion. Many varied expression control sequences, including native and non-native, constitutive, inducible and/or tissue-specific, arc known in the art and may be utilized herein. depending upon the type of expression desired.

Expression control sequences for eukaryotic cells typically include a promoter, an enhancer, such as one derived from an immunoglobulin gene, SV40, CMV, etc., and a polyadenylation sequence which may include splice donor and acceptor sites. The polyadenylation sequence generally is inserted 3' to the coding sequence and 5' to the 3' ITR sequence. PolyA from bovine growth hormone is a suitable sequence.

The regulatory sequences useful herein may also contain an intron, such as one located between the promoter/enhancer sequence and the coding sequence. One useful intron sequence is derived from SV40, and is referred to as the SV40 T intron sequence. Another includes the woodchuck hepatitis virus post-transcriptional element. (See, for example, Wang L and Verma, I, 1999, *Proc Nat'l Acad Sci USA*, 96:3906-10).

An IRES sequence, or other suitable system as discussed above, may be used to produce more than one polypeptide from a single transcript. n exemplary IRES is the poliovirus IRES which supports transgene expression in photoreceptors, RPE and ganglion cells. Preferably, the IRES is located 3' to the coding sequence in the rAAV vector.

The promoter may be selected from a number of constitutive or inducible promoters that can d rive expression of the selected transgene in an ocular setting, preferably in retinal neurons. A preferred promoter is "cell-specific", meaning that it is selected to direct expression of the selected transgene in a particular ocular cell type, such as photoreceptor cells.

Examples of useful constitutive promoters include the exemplified ??? CMV immediate early enhancer/chicken β-actin (CβA) promoter-exon 1-intron 1 element, the RSV LTR promoter/enhancer, the SV40 promoter, the CMV promoter, the dihydrofolate reductase (DHFR) promoter, and the phosphoglycerol kinase (PGK) promoter.

Additional useful promoters are disclosed in W.W. Hauswirth et al., 1998, W098/48027 and A. M. Timmers et al., 2000, W000/15822. Promoters that were found to drive RPE cell-specific gene expression in vivo include (1) a 528-bp promoter region (bases 1-528 of a murine 1 1-cis retinol dehydrogenase (RDH) gene (Driessen, C A et al., 1995, *Invest. Ophthalmol. Vis. Sci.* 36:1988-96; Simon, A. et al., 1995, *J. Biol. Chem* 270:1107-12, 1995; Simon, A. et al., 1996, *Genomics* 36:424-3) Genbank Accession Number X97752); (2) a 2274-bp promoter region) from a human cellular retinaldehyde-binding protein (CRALBP) gene (Intres, R et al., 1994, *J. Biol. Chem.* 269:25411-18; Kennedy, B N et al., 1998, *J. Biol. Chem.* 273:5591-8, 1998), Genbank Accession Number L34219); and (3) a 1485-bp promoter region from human RPE65 (Nicoletti, A et al., 1998, *Invest. Ophthalmol. Vis. Sci.* 39:637-44, Genbank Accession Number U20510). These three promoters (labeled with the following SEQ ID numbers in W000/15822" 2.3 and 3) promoted RPE-cell specific expression of GFP. It is envisioned that minor sequence variations in the various promoters and promoter regions discussed herein—whether additions, deletions or mutations, whether naturally occurring or introduced in vitro, will not affect their ability to drive expression in the cellular targets of the present invention. Furthermore, the use of other promoters, even if not yet discovered, that are characterized by abundant and/or specific expression in retinal cells, particularly in bipolar or ganglion cells, is specifically included within the scope of this invention.

An inducible promoter is used to control the amount and timing of production of the transgene product in an ocular cell. Such promoters can be useful if the gene product has some undesired, e.g., toxic, effects in the cell if it accumulates excessively. Inducible promoters include those known in the art, such as the Zn-inducible sheep metallothionine (MT) promoter, the dexamethasone (Dex)-inducible mouse mammary tumor virus (MMTV) promoter; the T7 promoter; the ecdysone insect promoter; the tetracycline-repressible system; the tetracycline-inducible system; the RU486-inducible system; and the rapamycin-inducible system. Any inducible promoter the action of which is tightly regulated and is specific for the particular target ocular cell type, may be used. Other useful types of inducible promoters are ones regulated by a specific physiological state, e.g., temperature, acute phase, a cell's replicating or differentiation state.

Selection of the various vector and regulatory elements for use herein are conventional, well-described, and readily available. See, e.g., Sambrook et al., supra; and Ausubel et al., supra. It will be readily appreciated that not all vectors and expression control sequences will function equally well to express the present transgene, preferably Chop2. Clearly, the skilled artisan may apply routine selection among the known expression control sequences without departing from the scope of this invention and based upon general knowledge as well as the guidance provided herein. One skilled in the art can select one or more expression control sequences, operably link them to the coding sequence being expressed to make a minigene, insert the minigene or vector into an AAV vector, and cause packaging of the vector into infectious particles or virions following one of the known packaging methods for rAAV.

Production of the rAAV

The rAAV used in the present invention may be constructed and produced using the materials and methods described herein and those well-known in the art. The methods that are preferred for producing any construct of this invention are conventional and include genetic engineering, recombinant engineering, and synthetic techniques, such as those set forth in reference cited above.

Briefly, to package an rAAV construct into an rAAV virion, a sequences necessary to express AAV rep and AAV cap or functional fragments thereof as well as helper genes essential for AAV production must be present in the host cells. See, for example U.S. Patent Pub. 2007/0015238, which describes production of pseudotyped rAAV virion vectors encoding AAV Rep and Cap proteins of different serotypes and AdV transcription products that provide helper functions For example, AAV rep and cap sequences may be introduced into the host cell in any known manner including, without limitation, transfection, electroporation, liposome delivery, membrane fusion, biolistic deliver of DNA-coated pellets, viral infection and protoplast fusion. Devices specifically adapted for delivering DNA to specific regions within and around the eye for the purpose of gene therapy have been described recently (for example, U.S. Patent Pub. 2005/0277868, incorporated by reference) are used within the scope of this invention.. Such devices utilize electroporation and electromigration, providing, e.g., two electrodes on a flexible support that can be placed behind the retina. A third electrode is part of a hollow support, which can also be used to inject the molecule to the desired area. The electrodes can be positioned around the eye, including behind the retina or within the vitreous.

These sequences may exist stably in the cell as an episome or be stably integrated into the cell's genome. They may also be expressed more transiently in the host cell. As an example, a useful nucleic acid molecule comprises, from 5' to 3', a promoter, an optional spacer between the promoter and the start site of the rep sequence, an AAV rep sequence, and an AAV cap sequence.

The rep and cap sequences, along with their expression control sequences, are preferably provided in a single vector, though they may be provided separately in individual vectors. The promoter may be any suitable constitutive, inducible or native promoter. The delivery molecule that provides the Rep and Cap proteins may be in any form., preferably a plasmid which may contain other non-viral sequences, such as those to be employed as markers. This molecule typically excludes the AAV ITRs and packaging sequences. To avoid the occurrence of homologous recombination, other viral sequences, particularly adenoviral sequences, are avoided. This plasmid is preferably one that is stably expressed.

Conventional genetic engineering or recombinant DNA techniques described in the cited references are used. The rAAV may be produced using a triple transfection method with either the calcium phosphate (Clontech) or Effectene™ reagent (Qiagen) according to manufacturer's instructions. See, also, Herzog et al., 1999, Nat. Med. 5:56-63.

The rAAV virions are produced by culturing host cells comprising a rAAV as described herein which includes a rAAV construct to be packaged into a rAAV virion, an AAV rep sequence and an AAV cap sequence, all under control of regulatory sequences directing expression.

Suitable viral helper genes, such as adenovirus E2A, E4Orf6 and VA, may be added to the culture preferably on separate plasmids. Thereafter, the rAAV virion which directs expression of the transgene is isolated in the absence of contaminating helper virus or wildtype AAV.

It is conventional to assess whether a particular expression control sequence is suitable for a given transgene, and choose the one most appropriate for expressing the transgene. For example, a target cell may be infected in vitro, and the number of copies of the transgene in the cell monitored by Southern blots or quantitative PCR. The level of RNA expression may be monitored by Northern blots quantitative RT-PCR. The level of protein expression may be monitored by Western blot, immunohistochemistry, immunoassay including enzyme immunoassay (EIA) such as enzyme-linked immunosorbent assays (ELISA), radioimmunoassays (RIA) or by other methods. Specific embodiments are described in the Examples below.

Pharmaceutical Compositions and Methods of the Invention

The rAAV that comprises the Chop2 transgene and cell-specific promoter for use in the target ocular cell as described above should be assessed for contamination using conventional methods and formulated into a sterile or aseptic pharmaceutical composition for administration by, for example, subretinal injection.

Such formulations comprise a pharmaceutically and/or physiologically acceptable vehicle, diluent, carrier or excipient, such as buffered saline or other buffers, e.g., HEPES, to maintain physiologic pH. For a discussion of such components and their formulation, see, generally, Gennaro, A E., *Remington: The Science and Practice of Pharmacy*, Lippincott Williams & Wilkins Publishers; 2003 or latest edition). See also, WO00/15822. If the preparation is to be stored for long periods, it may be frozen, for example, in the presence of glycerol.

The pharmaceutical composition described above is administered to a subject having a visual or blinding disease by any appropriate route, preferably by intravitreal or subretinal injection, depending on the retinal layer being targeted.

Disclosures from Bennett and colleagues (cited herein) concern targeting of retinal pigment epithelium—the most distal layer from the vitreal space. According to the present invention, the DNA construct is targeted to either retinal ganglion cells or bipolar cells. The ganglion cells are reasonably well-accessible to intravitreal injection as disclosed herein. Intravitreal and/or subretinal injection can provide the necessary access to the bipolar cells, especially in circumstances in which the photoreceptor cell layer is absent due to degeneration—which is the case in certain forms of degeneration that the present invention is intended to overcome.

To test for the vector's ability to express the transgene, specifically in mammalian retinal neurons, by AAV-mediated delivery, a combination of a preferred promoter sequence linked to a reporter gene such as LacZ or GFP linked to a SV40 poly A sequence can be inserted into a plasmid and packaged into rAAV virus particles, concentrated, tested for contaminating adenovirus and titered for rAAV using an infectious center assay. The right eyes of a number of test subjects, preferably inbred mice, are injected sub-retinally with about 1μl of the rAAV preparation (e.g., greater than about $10^{10}$ infectious units ml). Two weeks later, the right (test) and left (control) eyes of half the animals are removed, fixed and stained with an appropriate substrate or antibody or other substance to reveal the presence of the reporter gene. A majority of the test retinas in injected eyes will exhibited a focal stained region, e.g., blue for LacZ/Xgal, or green for GFP consistent with a subretinal bleb of the injected virus creating a localized retinal detachment. All control eyes are negative for the reporter gene product. Reporter gene expression examined in mice sacrificed at later periods is detected for at least 10 weeks post-injection, which suggests persistent expression of the reporter transgene.

An effective amount of rAAV virions carrying a nucleic acid sequence encoding the Chop2 DNA under the control of the promoter of choice, preferably a constitutive CMV promoter or a cell-specific promoter such as mGluR6, is preferably in the range of between about $10^{10}$ to about $10^{13}$ rAAV infectious units in a volume of between about 150 and about 800 µl per injection. The rAAV infectious units can be measured according to McLaughlin, S K et al., 1988, *J Virol* 62:1963. More preferably, the effective amount is between about $10^{10}$ and about $10^{12}$ rAAV infectious units and the injection volume is preferably between about 250 and about 500 µl. Other dosages and volumes, preferably within these ranges but possibly outside them, may be selected by the treating professional, taking into account the physical state of the subject (preferably a human), who is being treated, including, age, weight, general health, and the nature and severity of the particular ocular disorder.

It may also be desirable to administer additional doses ("boosters") of the present nucleic acid or rAAV compositions. For example, depending upon the duration of the transgene expression within the ocular target cell, a second treatment may be administered after 6 months or yearly, and may be similarly repeated. Neutralizing antibodies to AAV are not expected to be generated in view of the routes and doses used, thereby permitting repeat treatment rounds.

The need for such additional doses can be monitored by the treating professional using, for example, well-known electrophysiological and other retinal and visual function tests and visual behavior tests. The treating professional will be able to select the appropriate tests applying routine skill in the art. It may be desirable to inject larger volumes of the composition in either single or multiple doses to further improve the relevant outcome parameters.

Restoration or Improvement of Light Sensitivity and Vision

Both in vitro and in vivo studies to assess the various parameters of the present invention may be used, including recognized animal models of blinding human ocular disorders. Large animal models of human retinopathy, e.g., childhood blindness, are useful. The examples provided herein allow one of skill in the art to readily anticipate that this method may be similarly used in treating a range of retinal diseases.

While earlier studies by others have demonstrated that retinal degeneration can be retarded by gene therapy techniques, the present invention demonstrates a definite physiological recovery of function, which is expected to generate or improve various parameters of vision, including behavioral parameters.

Behavioral measures can be obtained using known animal models and tests, for example performance in a water maze, wherein a subject in whom vision has been preserved or restored to varying extents will swim toward light (Hayes, J M et al., 1993, *Behav Genet* 23:395-403).

In models in which blindness is induced during adult life or congenital blindness develops slowly enough that the individual experiences vision before losing it, training of the subject in various tests may be done. In this way, when these tests are re-administered after visual loss to test the efficacy of the present compositions and methods for their vision-restorative effects, animals do not have to learn the tasks de novo while in a blind state. Other behavioral tests do not require learning and rely on the instinctiveness of certain behaviors. An example is the optokinetic nystagmus test (Balkema G W et al., 1984, *Invest Ophthalmol Vis Sci.* 25:795-800; Mitchiner J C et al., 1976, *Vision Res.* 16:1169-71).

As is exemplified herein, the transfection of retinal neurons with DNA encoding Chop2 provides residual retinal neurons, principally bipolar cells and ganglion cells, with photosensitive membrane channels. Thus, it was possible to measure, with a strong light stimulus, the transmission of a visual stimulus to the animal's visual cortex, the area of the brain responsible for processing visual signals; this therefore constitutes a form of vision, as intended herein. Such vision may differ from forms of normal human vision and may be referred to as a sensation of light, also termed "light detection" or "light perception."

Thus, the term "vision" as used herein is defined as the ability of an organism to usefully detect light as a stimulus for differentiation or action. Vision is intended to encompass the following:

1. Light detection or perception—the ability to discern whether or not light is present
2. Light projection—the ability to discern the direction from which a light stimulus is coming;
3. Resolution—the ability to detect differing brightness levels (i.e., contrast) in a grating or letter target; and
4. Recognition—the ability to recognize the shape of a visual target by reference to the differing contrast levels within the target.

Thus, "vision" includes the ability to simply detect the presence of light. This opens the possibility to train an affected subject who has been treated according to this invention to detect light, enabling the individual to respond remotely to his environment however crude that interaction might be. In one example, a signal array is produced to which a low vision person can respond to that would enhance the person's ability to communicate by electronic means remotely or to perform everyday tasks. In addition such a person's mobility would be dramatically enhanced if trained to use such a renewed sense of light resulting from "light detection." The complete absence of light perception leaves a person with no means (aside from hearing and smell) to discern anything about objects remote to himself.

The methods of the present invention that result in light perception, even without full normal vision, also improve or permit normally regulated circadian rhythms which control many physiological processes including sleep-wake cycles and associated hormones. Although some blind individuals with residual retinal ganglion cells (RGCs) can mediate their rhythms using RGC melanopsin, it is rare for them to do so. Thus, most blind persons have free-running circadian rhythms. Even when such individuals do utilize the melanopsin pathway, the effect is very weak effect. The methods of the present invention are thus expected to improve health status of blind individuals by enabling absent light entrainment or improving weakened (melanopsin-mediated) light entrainment of their circadian rhythms. This leads to better health and well-being of these subjects.

In addition to circadian rhythms, the present invention provides a basis to improve deficits in other light-induced physiological phenomena. Photoreceptor degeneration may result in varying degrees of negative masking, or suppression, of locomotor activity during the intervals in the circadian cycle in which the individual should be sleeping. Another result is suppression of pineal melatonin. Both of these contribute to the entrainment process. Thus, improvement in these responses or activities in a subject in whom photoreceptors are degenerating or have degenerated contributes, independently of vision per se, to appropriate sleep/wake cycles that correspond with the subject's environment in the real world.

Yet another benefit of the present invention is normalization of pupillary light reflexes because regulation of pupil size helps modulate the effectiveness of light stimuli in a natural feed back loop. Thus, the present invention promotes re-establishment of this natural feedback loop, making vision more effective in subject treated as described herein.

In certain embodiments, the present methods include the measurement of vision before, and preferably after, administering a vector comprising, for example, DNA encoding Chop2. Vision is measured using any of a number of methods well-known in the art or ones not yet established. Most preferred herein are the following visual responses:

(1) A light detection response by the subject after exposure to a light stimulus—in which evidence is sought for a reliable response of an indication or movement in the general direction of the light by the subject individual when the light it is turned on is .

(2) a light projection response by the subject after exposure to a light stimulus in which evidence is sought for a reliable response of indication or movement in the specific direction of the light by the individual when the light is turned on.

(3) light resolution by the subject of a light vs. dark patterned visual stimulus, which measures the subject's capability of resolving light vs dark patterned visual stimuli as evidenced by:

(a) the presence of demonstrable reliable optokinetically produced nystagmoid eye movements and/or related head or body movements that demonstrate tracking of the target (see above) and/or (b). the presence of a reliable ability to discriminate a pattern visual stimulus and to indicate such discrimination by verbal or non-verbal means, including, for example pointing, or pressing a bar or a button; or (4) electrical recording of a visual cortex response to a light flash stimulus or a pattern visual stimulus, which is an endpoint of electrical transmission from a restored retina to the visual cortex. Measurement may be by electrical recording on the scalp surface at the region of the visual cortex, on the cortical surface, and/or recording within cells of the visual cortex.

It is known in the art that it is often difficult to make children who have only light perception appreciate that they have this vision. Training is required to get such children to react to their visual sensations. Such a situation is mimicked in the animal studies exemplified below. Promoting or enhancing light perception, which the compositions and methods of the present invention will accomplish, is valuable because patients with light perception not only are trainable to see light, but they can usually be trained to detect the visual direction of the light, thus enabling them to be trained in mobility in their environment. In addition, even basic light perception can be used by visually impaired individuals, including those whose vision is improved using the present compositions and methods, along with specially engineered electronic and mechanical devices to enable these individuals to accomplish specific daily tasks. Beyond this and depending on their condition, they may even be able to be trained in resolution tasks such as character recognition and even reading if their impairment permits. Thus it is expected that the present invention enhances the vision of impaired subjects to such a level that by applying additional training methods, these individuals will achieve the above objectives.

Low sensitivity vision may emulate the condition of a person with a night blinding disorder, an example of which is Retinitis Pigmentosa (RP), who has difficulty adapting to light levels in his environment and who might use light amplification devices such as supplemental lighting and/or night vision devices.

Thus, the visual recovery that has been described in the animal studies described below would, in human terms, place the person on the low end of vision function. Nevertheless, placement at such a level would be a significant benefit because these individuals could be trained in mobility and potentially in low order resolution tasks which would provide them with a greatly improved level of visual independence compared to total blindness.

The mice studied in the present Examples were rendered completely devoid of photoreceptors; this is quite rare, even in the worst human diseases. The most similar human state is RP. In most cases of RP, central vision is retained till the very end. In contrast, in the studied mouse model, the mouse becomes completely blind shortly after birth.

Common disorders encountered in low vision are described by J. Tasca and E. A. Deglin in Chap. 6 of *Essentials of Low Vision Practice*, R. L. Brilliant, ed., Butterworth Heinemann Publ., 1999, which is incorporated by reference in its entirety. There is reference to similar degenerative conditions, but these references showform vision that is measurable as visual acuity. Ganglion cell layers are not retained in all forms of RP, so the present approach will not work for such a disorder.

When applying the present methods to humans with severe cases of RP, it is expected that central vision would be maintained for a time at some low level while the peripheral retina degenerated first. It is this degenerating retina that is the target for re-activation using the present invention. In essence, these individuals would be able to retain mobility vision as they approached blindness gradually.

Subjects with macular degeneration, characterized by photoreceptor loss within the central "sweet spot" of vision (Macula Lutea), are expected to benefit by treatment in accordance with the present invention, in which case the resolution capability of the recovered vision would be expected to be higher due to the much higher neuronal density within the human macula.

While it is expected that bright illumination of daylight and artificial lighting that may be used by a visually impaired individual will suffice for many visual activities that are performed with vision that has recovered as a result of the present treatments. It is also possible that light amplification devices may be used, as needed, to further enhance the affected person's visual sensitivity. The human vision system can operate over a 10 log unit range of luminance. On the other hand, microbial type rhodopsins, such as ChR2, operate over up to a 3 log unit range of luminance. In addition, the light conditions the patient encounters could fall outside of the operating range of the light sensor. To compensate for the various light conditions, a light pre-amplification or attenuation device could be used to expand the operation range of the light conditions. Such device would contain a camera, imaging processing system, and microdisplays, which can ne assembled from currently available technologies, such as night vision goggles and/or 3D adventure and entertainment system. (See, for example the following URL on the Worldwide web—emagin.com/.)

The present invention may be used in combination with other forms of vision therapy known in the art. Chief among these is the use of visual prostheses, which include retinal implants, cortical implants, lateral geniculate nucleus implants, or optic nerve implants. Thus, in addition to genetic modification of surviving retinal neurons using the present methods, the subject being treated may be provided with a visual prosthesis before, at the same time as, or after the molecular method is employed.

The effectiveness of visual prosthetics can be improved with training of the individual, thus enhancing the potential impact of the Chop2 transformation of patient cells as contemplated herein. An example of an approach to training is found in US 2004/0236389 (Fink et al.), incorporated by reference. The training method may include providing a non-visual reference stimulus to a patient having a visual prosthesis based on a reference image. The non-visual reference stimulus is intended to provide the patient with an expectation of the visual image that the prosthesis will induce. Examples of non-visual reference stimuli are a pinboard, Braille text, or a verbal communication. The visual prosthesis stimulates the patient's nerve cells, including those cells whose responsiveness has been improved by expressing Chop2 as disclosed herein, with a series of stimulus patterns attempting to induce a visual perception that matches the patient's expected perception derived from the non-visual reference stimulus. The patient provides feedback to indicate which of the series of stimulus patterns induces a perception that most closely resembles the expected perception. The patient feedback is used as a "fitness function" (also referred to as a cost function or an energy function). Subsequent stimuli provided to the patient through the visual prosthesis are based, at least in part, on the previous feedback of the patient as to which stimulus pattern(s) induce the perception that best matches the expected perception. The subsequent stimulus patterns may also be based, at least in part, on a fitness function optimization algorithm, such as a simulated annealing algorithm or a genetic algorithm.

Thus, in certain embodiments of this invention, the method of improving or restoring vision in a subject further comprises training of that subject, as discussed above. Preferred examples of training methods are:

(a) habituation training characterized by training the subject to recognize (i) varying levels of light and/or pattern stimulation, and/or (ii) environmental stimulation from a common light source or object as would be understood by one skilled in the art; and (b) orientation and mobility training characterized by training the subject to detect visually local objects and move among said objects more effectively than without the training.

In fact, any visual stimulation techniques that are typically used in the field of low vision rehabilitation are applicable here.

The remodeling of inner retinal neurons triggered by photoreceptor degeneration has raised a concerns about retinal-based rescue strategies after the death of photoreceptors (Strettoi and Pignatelli 2000, *Proc Natl Acad Sci USA*. 97:11020-5; Jones, BW et al., 2003, *J Comp Neurol* 464:1-16; Jones, BW and Marc, RE, 2005, *Exp Eye Res*. 81:123-37; Jones, BW et al., 2005, *Clin Exp Optom*. 88:282-91). Retinal remodeling is believed to result from deafferentation, the loss of afferent inputs from photoreceptors—in other words, the loss of light induced activities So after death of rods and coned, there is no light evoked input to retinal bipolar cells and ganglion cells, and through them to higher visual centers. In response to the loss of such input, the retina and higher visual network are triggered to undergo remodeling, in a way seeking other forms of inputs. Said otherwise, the retina needs to be used to sense light in order to maintain its normal network, and with the loss of light sensing, the network will deteriorate via a remodeling process. This process is not an immediate consequence of photoreceptor death; rather it is a slow process, providing a reasonably long window for intervention.

Thus, an additional utility of restoring light sensitivity to inner retinal neurons in accordance with the present invention is the prevention or delay in the remodeling processes in the retina, and, possibly, in the higher centers. Such retinal remodeling may have undesired consequences such as corruption of inner retinal network, primarily the connection between bipolar and retinal ganglion cells. By introducing the light-evoked activities in bipolar cells or ganglion cells, the present methods would prevent or diminish the remodeling due to the lack of input; the present methods introduce this missing input (either starting from bipolar cells or ganglion cells), and thereby stabilize the retinal and higher visual center network. Thus, independently of its direct effects on vision, the present invention would benefit other therapeutic approaches such as photoreceptor transplantation or device implants,.

Having now generally described the invention, the same will be more readily understood through reference to the following examples which are provided by way of illustration, and are not intended to be limiting of the present invention, unless specified.

SYNOPSIS OF EXAMPLES (references cited in the following sections may appear in a list at the end)

Methods

A Chop2-GFP chimera was made by linking a nucleic acid encoding green fluorescent protein (GFP) (part of SEQ ID NO:1 as shown below) to a nucleic acid (SEQ ID NO:2) encoding an active fragment (SEQ ID NO:3) of channelopsin-2 (Chop2) such that an expressed protein has the GFP linked to the C-terminus of the Chop2 region. Both these sequences constitute the "transgene" as discussed above. The Chop2-GFP DNA was transfected into HEK293 cells under control of a CMV promoter.

Figure 7:
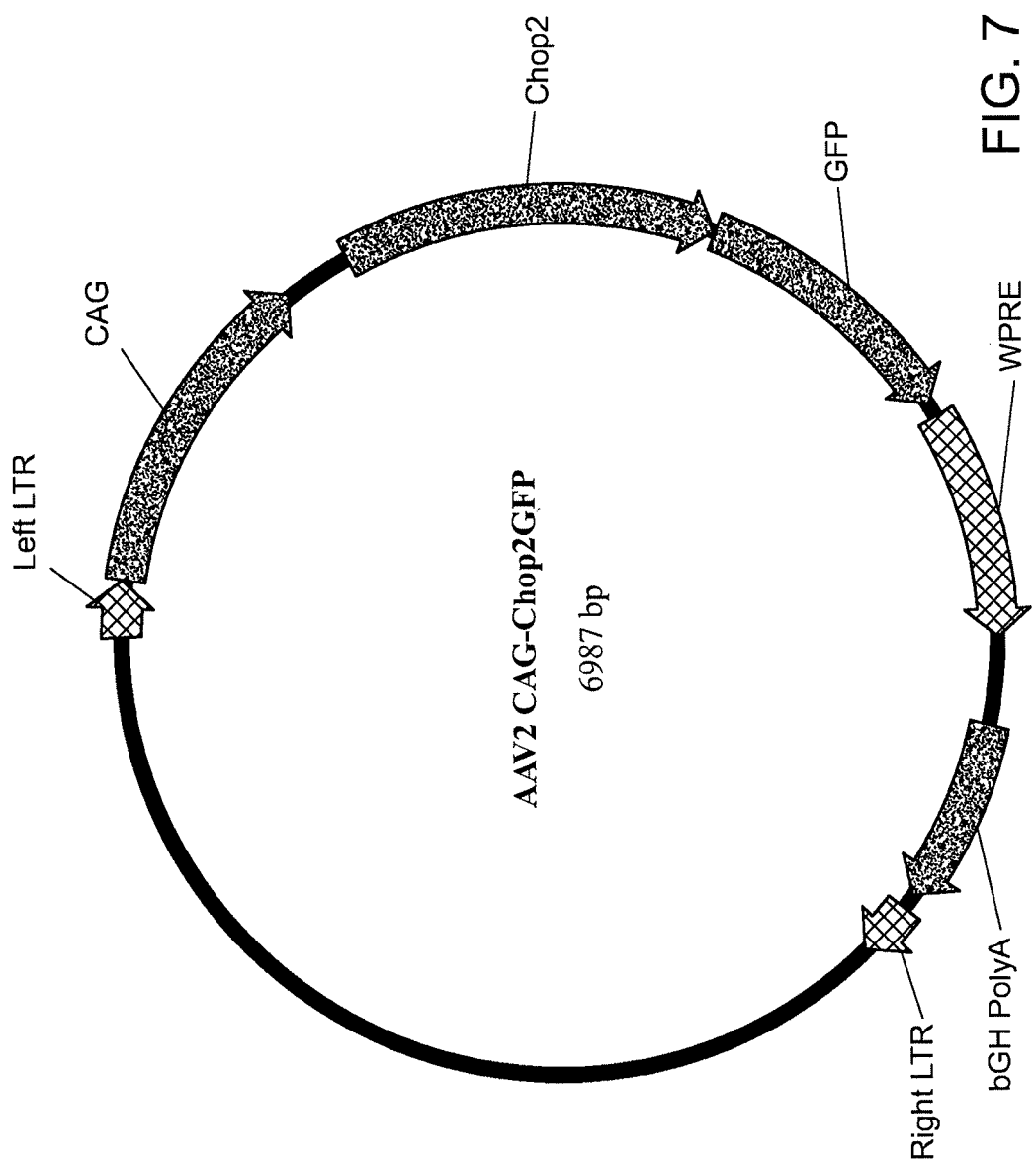
FIG. 7 shows a map of the viral expression construct rAAV2-CAG-Chop2-GFP-WPRE (SEQ ID NO:1), which comprises a Chop2-GFP fragment, an operatively linked a hybrid CMV enhancer/chicken β-actin promoter (CAG), a woodchuck posttranscriptional regulatory element (WPRE), and a bovine growth hormone (BGH) polyadenylation sequence.

A viral construct (SEQ ID NO:1) was made by subcloning the Chop2-GFP into an AAV-2 viral cassette containing a CAG promoter. A map of this construct is shown in FIG. 7. The viral vectors were injected into the eye of newborn rats. The expression of Chop2-GFP was examined by GFP fluorescence in retinal whole-mounts or slice sections. The function of the Chop2-GFP was assessed by whole-cell patch clamp recordings.

Results

Bright GFP fluorescence was detected within 18-24 hrs in HEK cells after the transfection. The fluorescence was localized predominantly to the plasma membrane. The preserve of the function of the Chop2-GFP chimera was confirmed by patch-clamp recordings. Substantial light-gated currents were also observed in the Chop2-GFP-expressing HEK cells without adding the exogenous all-trans retinal, indicating that a significant number of functional Chop2-GFP channels were formed in HEK cells using only endogenous precursor for the chromophore group. Three to four weeks after the injection, GFP fluorescence was observed in the retinal neurons of the injected eyes. Bright GFP-fluorescence was observed in many ganglion cells and horizontal cells, some amacrine cells, and, occasionally, bipolar cells for at least 10 weeks following injection. The Chop2-

GFP-expressing retinal neurons exhibited robust membrane depolarization in response to light stimulation and did not require an exogenous source of all-trans retinal.

Thus, the inventors demonstrated that the selected AAV vector construct efficiently targeted retinal ganglion cells and effectively delivered the Chop2-GFP cDNA and expressed protein at high levels after intravitreal injection in both normal and diseased retinas. When endogenous retinal was bound to the Chop2, it could be photoswitched, and neural activity could be evoked in retinas and at cortical levels. This was shown by several techniques—initially by in vitro patch-clamp recordings of individual dissociated RGCs, followed by multielectrode array recordings of whole-mount retina preparations representative of a large population of RGCs. Finally, in vivo cortical recordings from live blind mice demonstrated that critical connections were functionally maintained to higher visual centers.

Conclusion

The progressive in vitro and in vivo results show that ectopic expression of Chop2 is a therapeutic strategy for restoring light sensitivity to a "blind" retina. Functional expression of a directly light-gated membrane channel, Chop2, was demonstrated in rat retinal neurons in vivo. Thus, expression of light-gated membrane channels in second- or third-order retinal neurons is a useful strategy for restoration of light perception after photoreceptor degeneration.

Example 1

Materials and Methods

DNA and Viral Vector Constructions

The DNA fragment encoding the N-terminal fragment (Met'-Lys$^{315}$) of Chop2 (Nagel et al., 2003) was cloned into pBluescript vector (Stratagene) containing the last exon of a mouse protamine 1 gene containing polyadenylation signal (mP1) and GFP cDNA inserted in frame at the 3' end of the Chop2 coding fragment to produce a Chop2-GFP fusion protein. The function of Chop2-GFP chimera was verified in transfected HEK293 cells.

The viral expression construct rAAV2-CAG-Chop2-GFP-WPRE was made by subcloning the Chop2-GFP fragment into an adeno-associated (serotype-2) viral expression cassette. The viral cassette comprised a hybrid CMV enhancer/chicken β-actin promoter (CAG), a woodchuck posttranscriptional regulatory element (WPRE), and a bovine growth hormone (BGH) polyadenylation sequence. Viral vectors were packaged and affinity purified (GeneDetect).

The vector map is shown in FIG. 7.

The nucleic acid sequence of this vector (SEQ ID NO:1) is shown below in annotated form (with the annotations as described):

ITR's (at both ends) (UPPER CASE underscore)
CAG promoter sequence (*Lower case, bold, italic*)
Kozak sequence (lowercasedoubleunderscore)
Chop2 coding sequence (lowercase doubleunderscore)
Green fluorescent protein coding sequence (lower case, bold underscored)
WPRE (regulatory element): (UPPER CASE)
The BGH Poly A sequence is not marked.
The remaining sequence (all lower case), including between Chop2 and GFP, is vector sequence

```
←--------ITR----------
CCTGCAGGCA GCTGCGCGCT CGCTCGCTCA CTGAGGCCGC CCGGGCAAAG CCCGGGCGTC      60

GGGCGACCTT TGGTCGCCCG GCCTCAGTGA GCGAGCGAGC GCGCAGAGAG GGAGTGGCCA     120

-----ITR----------→                    ←--------CAG Promoter----------
ACTCCATCAC TAGGGGTTCC Tgcggccgca acgcgttacg tatcggatcc agaattcgtg     180
atatctgaat tcgtcgacaa gcttctcgag cctaggctag ctctagacca cacgtgtggg     240
ggccggccgt aatgagacgc acaaactaat atcacaaact ggaaatgtct atcaatatat     300
agttgctcta gttattaata gtaatcaatt acggggtcat tagttcatag cccatatatg     360
gagttccgcg ttacataact tacggtaaat ggcccgcctg gctgaccgcc caacgacccc     420
cgcccattga cgtcaataat gacgtatgtt cccatagtaa cgccaatagg gactttccat     480
tgacgtcaat gggtggagta tttacggtaa actgcccact tggcagtaca tcaagtgtat     540
catatgccaa gtacgccccc tattgactgtc aatgacggta aatggcccgc ctggcattat     600
gcccagtaca tgaccttatg ggactttcct acttggcagt acatctacgt attagtcatc     660
gctattacca tgcatggtcg aggtgagccc cacgttctgc ttcactctcc ccatctcccc     720 ccccteccca ccccaattt tgtatttatt tatttttaa ttattttgtg cagcgatggg     780
ggcggggggg gggggggggc gcgcgccagg cgggggcgggg cggggcgagg ggcggggcgg     840
ggcgaggcgg agaggtgcgg cggcagccaa tcagagcggc gcgctccgaa agtttcttt     900 tatggcgagg cggcggcggc ggcggcccta taaaaagcga agcgcgcggc gggcgggagt     960

--------------------CAG Promoter-------------------→
cgctgcgcgc tgccttcgcc ccgtgccccg ctccgccgcc gcctcgcgcc gcccgccccg    1020
```

-continued

```
gctctgactg accgcgttac tcccacaggt gagcgggcgg gacggccctt ctccttcggg    1080
ctgtaattag cgcttggttt aatgacggct tgtttctttt ctgtggctgc gtgaaagcct    1140
                                            <Kozak>←---------Chop2----
tgagggctc cgggagggcc cgagctcgcg atccgcagcc atggattatg gaggcgccc     1200 gagtgccgtt gggcgcgagc tgctatttgt aacgaaccca gtagtcgtca atggctctgt    1260
acttgtgcct gaggaccagt gttactgcgc gggctggatt gagtcgcgtg gcacaaacgg    1320
tgcccaaacg cgtcgaacg tgctgcaatg gcttgctgct ggcttctcca tcctactgct     1380
tatgttttac gcctaccaaa catggaagtc aacctgcggc tgggaggaga tctatgtgtg    1440
cgctatcgag atggtcaagg tgattcttga gttcttcttc gagtttaaga cccgtccat    1500 gctgtatcta gccacaggcc accgcgtcca gtggttgcgt tacgccgagt ggcttctcac    1560
ctgcccggtc attctcattc acctgtcaaa cctgacgggc ttgtccaacg actacagcag    1620
gcgcactatg gtctgcttg tgtctgatat tggcacaatt gtgtggggcg ccacttccgc     1680
tatggccacc ggatacgtca aggtcatctt cttctgcctg ggtctgtgtt atggtgctaa    1740
cacgttcttt cacgctgcca aggcctacat cgagggttac cataccgtgc cgaagggccg    1800
gtgtcgccag gtggtgactg gcatggcttg gctcttcttc gtatcatggg gtatgttccc    1860
catcctgttc atcctcggcc ccgagggctt cggcgtcctg agcgtgtacg ctccaccgt    1920 cggccacacc atcattgacc tgatgtcgaa gaactgctgg ggtctgctcg gccactacct    1980
gcgcgtgctg atccacgagc atatcctcat ccacggcgac attcgcaaga ccaccaaatt    2040
gaacattggt ggcactgaga ttgaggtcga cgctggtg gaggacgagg ccgaggctgg     2100
---------Chop2----------->                   ←-----GFP----
cgcggtcaac aagggcaccg gcaaggaatt cggaggcgga ggtggagcta gcaaaggaga    2160
agaactcttc actggagttg tcccaattct tgttgaatta gatggtgatg ttaacggcca    2220
caagttctct gtcagtggag agggtgaagg tgatgcaaca tacggaaaac ttacccctgaa    2280 gttcatctgc actactggca aactgcctgt tccatggcca acactagtca ctactctgtg    2340
ctatggtgtt caatgctttt caagatacc ggatcatatg aaacggcatg acttttcaa     2400 gagtgccatg cccgaaggtt atgtacagga aggaccatc ttcatcaaag atgacggcaa    2460
ctacaagaca cgtgctgaag tcaagtttga aggtgatacc cttgttaata aatcgagtt    2520 aaaaggtatt gacttcaagg aagatggcaa cattctggga cacaaattgg aatacaacta    2590
taactcacac aatgtataca tcatggcaga caaacaaaag aatggaatca agtgaacttt    2640
caagacccgc cacaacattg aagatggaag cgttcaacta gcagaccatt atcaacaaaa    2700
tactccaatt ggcgatggcc ctgtcctttt accagacaac cattacctgt ccacacaatc    2760
tgccctttcg aaagatccca acgaaaagag agaccacatg gtccttcttg agtttgtaac    2820
             ----------------GFP------------------→
agctgctggg attacacatg gcatggatga actgtacaac atcgattgac taagcttgcc    2880
                           ←-------------------WPRE-----------------
tcgagaattc acgcgtggta cCGATAATCA ACCTCTGGAT TACAAAATTT GTGAAAGATT    2940

GACTGGTATT CTTAACTATG TTGCTCCTTT TACGCTATGT GGATACGCTG CTTTAATGCC    3000

TTTGTATCAT GCTATTGCTT CCCGTATGGC TTTCATTTTC TCCTCCTTGT ATAAATCCTG    3060

GTTGCTGTCT CTTTATGAGG AGTTGTGGCC CGTTGTCAGG CAACGTGGCG TGGTGTGCAC    3120

TGTGTTTGCT GACGCAACCC CCACTGGTTG GGCATTGCC ACCACCTGTC AGCTCCTTTC     3180

CGGGACTTTC GCTTTCCCCC TCCCTATTGC CACGGCGGAA CTCATCGCCG CCTGCCTTGC    3240

CCGCTGCTGA CAGGGGCTC GGCTGTTGGG CACTGACAAT TCCGTGGTGT TGTCGGGAA     3300

GCTGACGTCC TTTCCATGGC TGCTCGCCTG TGTTGCCACC TGGATTCTGC GCGGGACGTC    3360
```

```
CTTCTGCTAC GTCCCTTCGG CCCTCAATCC AGCGGACCTT CCTTCCCGCG GCCTGCTGCC    3420

GGCTCTGCGG CCTCTTCCGC GTCTTCGCCT TCGCCCTCAG ACGAGTCGGA TCTCCCTTTG    3480

--------WPRE-------→
GGCCGCCTCC CCGCCTGATC cggccgcggg gatccagaca tgataagata cattgatgag    3540
tttggacaaa ccacaactag aatgcagtga aaaaaatgct ttatttgtga aatttgtgat    3600
gctattgctt tatttgtaac cattataagc tgcaataaac aagttaacaa caacaattgc    3660
attcatttta tgtttcaggt tcagggggag gtgtgggagg ttttttcgga tcctctagag    3720

←-----------------------bGH PolyA--------------------
tcgagagatc tacgggtggc atccctgtga cccctcccca gtgcctctcc tggccctgga    3780
agttgccact ccagtgccca ccagccttgt cctaataaaa ttaagttgca tcattttgtc    3840
tgactaggtg tccttctata atattatggg gtgaggggg gtggtatgga gcaaggggca    3900
agttgggaag acaacctgta gggcctgcgg ggtctattgg gaaccaagct ggagtgcagt    3960
ggcacaatct tggctcactg caatctccgc ctcctgggtt caagcgattc tcctgcctca    4020
gcctcccgag ttgttgggat tccaggcatg catgaccagg ctcagctaat ttttgttttt    4080
ttggtagaga cggggtttca ccatattggc caggctggtc tccaactcct aatctcaggt    4140
gatctaccca ccttggcctc ccaaattgct gggattacag gcgtgaacca ctgctccctt    4200

-bGH PolyA→                                              ←---ITR---
ccctgtcctt ctgattttgt aggtaaccac gtgcggaccg agcggccgcA GGAACCCCTA    4260

GTGATGGAGT TGGCCACTCC CTCTCTGCGC GCTCGCTCGC TCACTGAGGC CGGGCGACCA    4320

AAGGTCGCCC GACGCCCGGG CTTTGCCCGG GCGGCCTCAG TGAGCGAGCG AGCGCGCAGC    4380

---ITR---→
TGCCTGCAGG ggcgcctgat gcggtatttt ctccttacgc atctgtgcgg tatttcacac    4440
cgcatacgtc aaagcaacca tagtacgcgc cctgtagcgg cgcattaagc gcggcgggtg    4500
tggtggttac gcgcagcgtg accgctacac ttgccagcgc cctagcgccc gctcctttcg    4560
ctttcttccc ttcctttctc gccacgttcg ccggctttcc ccgtcaagct ctaaatcggg    4620
ggctcccttt agggttccga tttagtgctt tacggcacct cgaccccaaa aaacttgatt    4680
tgggtgatgg ttcacgtagt gggccatcgc cctgatagac ggttttttcg ccttttgacgt    4740 tggagtccac gttctttaat agtggactct tgttccaaac tggaacaaca ctcaacccta    4800
tctcgggcta ttcttttgat ttataaggga ttttgccgat ttcggcctat tggttaaaaa    4860
atgagctgat ttaacaaaaa tttaacgcga attttaacaa aatattaacg tttacaattt    4920
tatggtgcac tctcagtaca atctgctctg atgccgcata gttaagccag ccccgacacc    4980
cgccaacacc cgctgacgcg ccctgacggg cttgtctgct cccggcatcc gcttacagac    5040
aagctgtgac cgtctccggg agctgcatgt gtcagaggtt ttcaccgtca tcaccgaaac    5100
gcgcgagacg aaagggcctc gtgatacgcc tatttttata ggttaatgtc atgataataa    5160
tggtttctta cacgtcaggt ggcacttttc ggggaaatgt gcgcggaacc cctatttgtt    5220
tatttttcta aatacattca aatatgtatc cgctcatgag acaataaccc tgataaatgc    5280
ttcaataata ttgaaaaagg aagagtatga gtattcaaca tttccgtgtc gcccttattc    5340
ccttttttgc ggcattttgc cttcctgttt ttgctcaccc agaaacgctg gtgaaagtaa    5400
aagatgctga agatcagttg ggtgcacgag tgggttacat cgaactggat ctcaacagcg    5460
gtaagatcct tgagagtttt cgccccgaag aacgttttcc aatgatgagc acttttaaag    5520
ttctgctatg tggcgcggta ttatcccgta ttgacgccgg gcaagagcaa ctcggtcgcc    5580
gcatacacta ttctcagaat gacttggttg agtactcacc agtcacagaa aagcatctta    5640
```

```
cggatggcat gacagtaaga gaattatgca gtgctgccat aaccatgagt gataacactg    5700
cggccaactt acttctgaca acgatcggag gaccgaagga gctaaccgct tttttgcaca    5760
acatggggga tcatgtaact cgccttgatc gttgggaacc ggagctgaat gaagccatac    5820
caaacgacga gcgtgacacc acgatgcctg tagcaatggc aacaacgttg cgcaaactat    5880
taactggcga actacttact ctagcttccc ggcaacaatt aatagactgg atggaggcgg    5940
ataaagttgc aggaccactt ctgcgctcgg cccttccggc tggctggttt attgctgata    6000
aatctggagc cggtgagcgt gggtctcgcg gtatcattgc agcactgggg ccagatggta    6060
agccctcccg tatcgtagtt atctacacga cggggagtca ggcaactatg gatgaacgaa    6120
atagacagat cgctgagata ggtgcctcac tgattaagca ttggtaactg tcagaccaag    6180
tttactcata tactttag attgatttaa aacttcattt ttaatttaaa aggatctagg    6240
tgaagatcct ttttgataat ctcatgacca aaatccctta acgtgagttt tcgttccact    6300
gagcgtcaga ccccgtagaa aagatcaaag gatcttcttg agatcctttt tttctgcgcg    6360
taatctgctg cttgcaaaca aaaaaaccac cgctaccagc ggtggtttgt ttgccggatc    6420
aagagctacc aactcttttt ccgaaggtaa ctggcttcag cagagcgcag ataccaaata    6480
ctgtccttct agtgtagccg tagttaggcc accacttcaa gaactctgta gcaccgccta    6540
catacctcgc tctgctaatc ctgttaccag tggctgctgc cagtggcgat aagtcgtgtc    6600
ttaccgggtt ggactcaaga cgatagttac cggataaggc gcagcggtcg ggctgaacgg    6660
ggggttcgtg cacacagccc agcttggagc gaacgaccta caccgaactg agatacctac    6720
agcgtgagct atgagaaagc gccacgcttc ccgaagggag aaaggcggac aggtatccgg    6780
taagcggcag ggtcggaaca ggagagcgca cgagggagct tccaggggga aacgcctggt    6840
atctttatag tcctgtcggg tttcgccacc tctgacttga gcgtcgattt ttgtgatgct    6900
cgtcaggggg gcggagccta tggaaaaacg ccagcaacgc ggcctttta cggttcctgg    6960 cctttgctg gccttttgct cacatgt                                         6987
```

The Chop2 coding sequence from the above vector is shown below as SEQ ID NO:2. Numbering indicates both nucleotide number and codon number. The encoded polypeptide (SEQ ID NO:3) is also shown. Again, this is the N-terminal 315 residues of Chop2 polypeptide (SEQ ID NO:6).

```
atg gat tat gga ggc gcc ctg agt gcc gtt ggg cgc gag ctg cta ttt    48
 M   D   Y   G   G   A   L   S   A   V   G   R   E   L   L   F    16 gta acg aac cca gta gtc gtc aat ggc tct gta ctt gtg cct gag gac    96
 V   T   N   P   V   V   V   N   G   S   V   L   V   P   E   D    32 cag tgt tac tgc gcg ggc tgg att gag tcg cgt ggc aca aac ggt gcc   144
 Q   C   Y   C   A   G   W   I   E   S   R   G   T   N   G   A    48 caa acg gcg tcg aac gtg ctg caa tgg ctt gct gct ggc ttc tcc atc   192
 Q   T   A   S   N   V   L   Q   W   L   A   A   G   F   S   I    64 cta ctg ctt atg ttt tac gcc tac caa aca tgg aag tca acc tgc ggc   240
 L   L   L   M   F   Y   A   Y   Q   T   W   K   S   T   C   G    80 tgg gag gag atc tat gtg tgc gct atc gag atg gtc aag gtg att ctt   288
 W   E   E   I   Y   V   C   A   I   E   M   V   K   V   I   L    96 gag ttc ttc ttc gag ttt aag aac ccg tcc atg ctg tat cta gcc aca   336
 E   F   F   F   E   F   K   N   P   S   M   L   Y   L   A   T   112 ggc cac cgc gtc cag tgg ttg cgt tac gcc gag tgg ctt ctc acc tgc   384
 G   H   R   V   Q   W   L   R   Y   A   E   W   L   L   T   C   128 ccg gtc att ctc att cac ctg tca aac ctg acg ggc ttg tcc aac gac   432
 P   V   I   L   I   H   L   S   N   L   T   G   L   S   N   D   144
```

```
tac agc agg cgc act atg ggt ctg ctt gtg tct gat att ggc aca att   480
 Y   S   R   R   T   M   G   L   L   V   S   D   I   G   T   I    160 gtg tgg ggc gcc act tcc gct atg gcc acc gga tac gtc aag gtc atc   528
 V   W   G   A   T   S   A   M   A   T   G   Y   V   K   V   I    176 ttc ttc tgc ctg ggt ctg tgt tat ggt gct aac acg ttc ttt cac gct   576
 F   F   C   L   G   L   C   Y   G   A   N   T   F   F   H   A    192 gcc aag gcc tac atc gag ggt tac cat acc gtg ccg aag ggc cgg tgt   624
 A   K   A   Y   I   E   G   Y   H   T   V   P   K   G   R   C    208 cgc cag gtg gtg act ggc atg gct tgg ctc ttc ttc gta tca tgg ggt   672
 R   Q   V   V   T   G   M   A   W   L   F   F   V   S   W   G    224 atg ttc ccc atc ctg ttc atc ctc ggc ccc gag ggc ttc ggc gtc ctg   720
 M   F   P   I   L   F   I   L   G   P   E   G   F   G   V   L    240 agc gtg tac ggc tcc acc gtc ggc cac acc atc att gac ctg atg tcg   768
 S   V   Y   G   S   T   V   G   H   T   I   I   D   L   M   S    256 aag aac tgc tgg ggt ctg ctc ggc cac tac ctg cgc gtg ctg atc cac   816
 K   N   C   W   G   L   L   G   H   Y   L   R   V   L   I   H    272 gag cat atc ctc atc cac ggc gac att cgc aag acc acc aaa ttg aac   864
 E   H   I   L   I   H   G   D   I   R   K   T   T   K   L   N    288 att ggt ggc act gag att gag gtc gag acg ctg gtg gag gac gag gcc   912
 I   G   G   T   E   I   E   V   E   T   L   V   E   D   E   A    304 gag gct ggc gcg gtc aac aag ggc acc ggc aag                       945
 E   A   G   A   V   N   K   G   T   G   K                        315
```

A native nucleic acid sequence that encodes the full length Chop2 protein of *C. reinhardtii* (GenBank Accession #AF461397) has the following nucleotide sequence (SEQ ID NO:4). Note that the coding sequence begins at the ATG codon beginning at nt 28.

```
   1  gcatctgtcg ccaagcaagc attaaacATG gattatggag gcgccctgag tgccgttggg
  61  cgcgagctgc tatttgtaac gaacccagta gtcgtcaatg gctctgtact tgtgcctgag
 121  gaccagtgtt actgcgcggg ctggattgag tcgcgtggca caaacggtgc ccaaacggcg
 181  tcgaacgtgc tgcaatggct tgctgctggc ttctccatcc tactgcttat gttttacgcc
 241  taccaaacat ggaagtcaac ctgcggctgg gaggagatct atgtgtgcgc tatcgagatg
 301  gtcaaggtga ttctcgagtt cttcttcgag tttaagaacc cgtccatgct gtatctagcc
 361  acaggccacc gcgtccagtg gttgcgttac gccgagtggc ttctcacctg cccggtcatt
 421  ctcattcacc tgtcaaacct gacgggcttg ccaacgact acagcaggcg caccatgggt
 481  ctgcttgtgt ctgatattgg cacaattgtg tggggcgcca cttccgccat ggccaccgga
 541  tacgtcaagg tcatcttctt ctgcctgggt ctgtgttatg gtgctaacac gttctttcac
 601  gctgccaagg cctacatcga gggttaccac accgtgccga agggccggtg tcgccaggtg
 661  gtgactggca tggcttggct cttcttcgta tcatggggta tgttccccat cctgttcatc
 721  ctcggccccg agggcttcgg cgtcctgagc gtgtacggct ccaccgtcgg ccacaccatc
 781  attgacctga tgtcgaagaa ctgctggggt ctgctcggcc actacctgcg cgtgctgatc
 841  cacgagcata tcctcatcca cggcgacatt cgcaagacca ccaaattgaa cattggtggc
 901  actgagattg aggtcgagac gctggtggag gacgaggccg aggctggcgc ggtcaacaag
 961  ggcaccggca agtacgcctc ccgcgagtcc ttcctggtca tgcgcgacaa gatgaaggag
1021  aagggcattg acgtgcgcgc ctctctggac aacagcaagg aggtggagca ggagcaggcc
1081  gccagggctg ccatgatgat gatgaacggc aatggcatgg gtatgggaat gggaatgaac
```

-continued

```
1141  ggcatgaacg gaatgggcgg tatgaacggg atggctggcg gcgccaagcc cggcctggag
1201  ctcactccgc agctacagcc cggccgcgtc atcctggcgg tgccggacat cagcatggtt
1261  gacttcttcc gcgagcagtt tgctcagcta tcggtgacgt acgagctggt gccggccctg
1321  ggcgctgaca acacactggc gctggttacg caggcgcaga acctgggcgg cgtggacttt
1381  gtgttgattc accccgagtt cctgcgcgac cgctctagca ccagcatcct gagccgcctg
1441  cgcggcgcgg ccagcgtgt ggctgcgttc ggctgggcgc agctggggcc catgcgtgac
1501  ctgatcgagt ccgcaaacct ggacggctgg ctggagggcc cctcgttcgg acagggcatc
1561  ctgccggccc acatcgttgc cctggtggcc aagatgcagc agatgcgcaa gatgcagcag
1621  atgcagcaga ttggcatgat gaccggcggc atgaacggca tgggcggcgg tatgggcggc
1681  ggcatgaacg gcatgggcgg cggcaacggc atgaacaaca tgggcaacgg catgggcggc
1741  ggcatgggca acggcatggg cggcaatggc atgaacgaa tgggtggcgg caacggcatg
1801  aacaacatgg gcggcaacgg aatggccggc aacggaatgg gggcggcat gggcggcaac
1861  ggtatgggtg gctccatgaa cggcatgagc tccggcgtgg tggccaacgt gacgccctcc
1921  gccgccggcg gcatgggcgg catgatgaac ggcggcatgg ctgcgcccca gtcgcccggc
1981  atgaacgcg gccgcctggg taccaacccg ctcttcaacg ccgcgccctc accgctcagc
2041  tcgcagctcg gtgccgaggc aggcatgggc agcatgggag gcatgggcgg aatgagcgga
2101  atgggaggca tgggtggaat gggggcatg ggcggcgccg cgccgccac gacgcaggct
2161  gcgggcggca acgcggaggc ggagatgctg cagaatctca tgaacgagat caatcgcctg
2221  aagcgcgagc ttggcgagta a
```

The coding portion of SEQ ID NO:4 is shown below as SEQ ID NO:5, organized as 737 triplet codons (plus a stop codon) that encode a 737 amino acid polypeptide. The ATG start codon and the TAA stop codon are highlighted.

```
ATG gat tat gga ggc gcc ctg agt gcc gtt ggg cgc gag ctg cta ttt
gta acg aac cca gta gtc gtc aat ggc tct gta ctt gtg cct gag gac
cag tgt tac tgc gcg ggc tgg att gag tcg cgt ggc aca aac ggt gcc
caa acg gcg tcg aac gtg ctg caa tgg ctt gct gct ggc ttc tcc atc
cta ctg ctt atg ttt tac gcc tac caa aca tgg aag tca acc tgc ggc
tgg gag gag atc tat gtg tgc gct atc gag atg gtc aag gtg att ctc
gag ttc ttc ttc gag ttt aag aac ccg tcc atg ctg tat cta gcc aca
ggc cac cgc gtc cag tgg ttg cgt tac gcc gag tgg ctt ctc acc tgc
ccg gtc att ctc att cac ctg tca aac ctg acg ggc ttg tcc aac gac
tac agc agg cgc acc atg ggt ctg ctt gtg tct gat att ggc aca att
gtg tgg ggc gcc act tcc gcc atg gcc acc gga tac gtc aag gtc atc
ttc ttc tgc ctg ggt ctg tgt tat ggt gct aac acg ttc ttt cac gct
gcc aag gcc tac atc gag ggt tac cac acc gtg ccg aag ggc cgg tgt
cgc cag gtg gtg act ggc atg gct tgg ctc ttc ttc gta tca tgg ggt
atg ttc ccc atc ctg ttc atc ctc ggc ccc gag ggc ttc ggc gtc ctg
agc gtg tac ggc tcc acc gtc ggc cac acc atc att gac ctg atg tcg
aag aac tgc tgg ggt ctg ctc ggc cac tac ctg cgc gtg ctg atc cac
gag cat atc ctc atc cac ggc gac att cgc aag acc acc aaa ttg aac
att ggt ggc act gag att gag gtc gag acg ctg gtg gag gac gag gcc
```

-continued

```
gag gct ggc gcg gtc aac aag ggc acc ggc aag tac gcc tcc cgc gag
tcc ttc ctg gtc atg cgc gac aag atg aag gag aag ggc att gac gtg
cgc gcc tct ctg gac aac agc aag gag gtg gag cag gag cag gcc gcc
agg gct gcc atg atg atg atg aac ggc aat ggc atg ggt atg gga atg
gga atg aac ggc atg aac gga atg ggc ggt atg aac ggg atg gct ggc
ggc gcc aag ccc ggc ctg gag ctc act ccg cag cta cag ccc ggc cgc
gtc atc ctg gcg gtg ccg gac atc agc atg gtt gac ttc ttc cgc gag
cag ttt gct cag cta tcg gtg acg tac gag ctg gtg ccg gcc ctg ggc
gct gac aac aca ctg gcg ctg gtt acg cag gcg cag aac ctg ggc ggc
gtg gac ttt gtg ttg att cac ccc gag ttc ctg cgc gac cgc tct agc
acc agc atc ctg agc cgc ctg cgc ggc gcg ggc cag cgt gtg gct gcg
ttc ggc tgg gcg cag ctg ggc ccc atg cgt gac ctg atc gag tcc gca
aac ctg gac ggc tgg ctg gag ggc ccc tcg ttc gga cag ggc atc ctg
ccg gcc cac atc gtt gcc ctg gtg gcc aag atg cag cag atg cgc aag
atg cag cag atg cag cag att ggc atg atg acc ggc ggc atg aac ggc
atg ggc ggc ggt atg ggc ggc ggc atg aac ggc atg ggc ggc ggc aac
ggc atg aac aac atg ggc aac ggc atg ggc ggc ggc atg ggc aac ggc
atg ggc ggc aat ggc atg aac gga atg ggt ggc ggc aac ggc atg aac
aac atg ggc ggc aac gga atg gcc ggc aac gga atg ggc ggc ggc atg
ggc ggc aac ggt atg ggt ggc tcc atg aac ggc atg agc tcc ggc gtg
gtg gcc aac gtg acg ccc tcc gcc gcc ggc ggc atg ggc ggc atg atg
aac ggc ggc atg gct gcg ccc cag tcg ccc ggc atg aac ggc ggc cgc
ctg ggt acc aac ccg ctc ttc aac gcc gcg ccc tca ccg ctc agc tcg
cag ctc ggt gcc gag gca ggc atg ggc agc atg gga ggc atg ggc gga
atg agc gga atg gga ggc atg ggt gga atg ggg ggc atg ggc ggc gcc
ggc gcc gcc acg acg cag gct gcg ggc ggc aac gcg gag gcg gag atg
ctg cag aat ctc atg aac gag atc aat cgc ctg aag cgc gag ctt ggc
gag taa                                                2214 nt's
```

The full length Chop2 protein of *C. reinhardtii* (GenBank Accession #AF461397) encoded by SEQ ID NO's 3 and 4, has the following amino acid sequence, SEQ ID NO:6:

```
MDYGGALSAVGRELLFVTNPVVVNGSVLVPEDQCYCAGWIESRGTNGAQT      50
ASNVLQWLAAGFSILLLMFYAYQTWKSTCGWEEIYVCAIEMVKVILEFFF      100
EFKNPSMLYLATGHRVQWLRYAEWLLTCPVILIHLSNLTGLSNDYSRRTM      150
GLLVSDIGTIVWGATSAMATGYVKVIFFCLGLCYGANTFFHAAKAYIEGY      200
HTVPKGRCRQVVTGMAWLFFVSWGMFPILFILGPEGFGVLSVYGSTVGHT      250
IIDLMSKNCWGLLGHYLRVLIHEHILIHGDIRKTTKLNIGGTEIEVETLV      300
EDEAEAGAVNKGTGKYASRESFLVMRDKMKEKGIDVRASLDNSKEVEQEQ      350
AARAAMMMMNGNGMGMGMNGMNGMGGMNGMAGGAKPGLELTPQLQPGR       400
VILAVPDISMVDFFREQFAQLSVTYELVPALGADNTLALVTQAQNLGGVD     450
```

```
FVLIHPEFLRDRSSTSILSRLRGAGQRVAAFGWAQLGPMRDLIESANLDG      500

WLEGPSFGQGILPAHIVALVAKMQQMRKMQQMQQIGMMTGGMNGMGGGMG      550

GGMNGMGGGNGMNNMGNGMGGGMGNGMGGNGMNGMGGGNGMNNMGGNGMA      600

GNGMGGGMGGNGMGGSMNGMSSGVVANVTPSAAGGMGGMMNGGMAAPQSP      650

GMNGGRLGTNPLFNAAPSPLSSQLGAEAGMGSMGGMGGMSGMGGMGGMGG      700

MGGAGAATTQAAGGNAEAEMLQNLMNEINRLKRELGE                   737
```

Another useful Chop2 sequence useful for the present invention is a nucleic acid of 933 nt's (including the stop codon) encoding a 310 aa polypeptide (a biologically active fragment of the full length native Chop2) is a synthetic construct derived from *Chlamydomonas reinhardtii*" (See EF474017 and Zhang et al., 2007, Nature in press). This sequence is codon-optimized for human expression. The nt sequence shown below is SEQ ID NO:7, and the encoded a.a. sequence shown is SEQ ID NO:8. The polypeptide with the a.a. sequence SEQ ID NO:8 is a fragment of SEQ ID NO:6 truncated at the C-terminus and with Pro replacing Asn at 310.

```
atg gac tat ggc ggc gct ttg tct gcc gtc gga cgc gaa ctt ttg ttc    48
 M   D   Y   G   G   A   L   S   A   V   G   R   E   L   L   F     16 gtt act aat cct gtg gtg gtg aac ggg tcc gtc ctg gtc cct gag gat    96
 V   T   N   P   V   V   V   N   G   S   V   L   V   P   E   D     32 caa tgt tac tgt gcc gga tgg att gaa tct cgc ggc acg aac ggc gct   144
 Q   C   Y   C   A   G   W   I   E   S   R   G   T   N   G   A     48 cag acc gcg tca aat gtc ctg cag tgg ctt gca gca gga ttc agc att   192
 Q   T   A   S   N   V   L   Q   W   L   A   A   G   F   S   I     64 ttg ctg ctg atg ttc tat gcc tac caa acc tgg aaa tct aca tgc ggc   240
 L   L   L   M   F   Y   A   Y   Q   T   W   K   S   T   C   G     80 tgg gag gag atc tat gtg tgc gcc att gaa atg gtt aag gtg att ctc   288
 W   E   E   I   Y   V   C   A   I   E   M   V   K   V   I   L     96 gag ttc ttt ttt gag ttt aag aat ccc tct atg ctc tac ctt gcc aca   336
 E   F   F   F   E   F   K   N   P   S   M   L   Y   L   A   T    112 gga cac cgg gtg cag tgg ctg cgc tat gca gag tgg ctg ctc act tgt   384
 G   H   R   V   Q   W   L   R   Y   A   E   W   L   L   T   C    128 cct gtc atc ctt atc cac ctg agc aac ctc acc ggc ctg agc aac gac   432
 P   V   I   L   I   H   L   S   N   L   T   G   L   S   N   D    144 tac agc agg aga acc atg gga ctc ctt gtc tca gac atc ggg act atc   480
 Y   S   R   R   T   M   G   L   L   V   S   D   I   G   T   I    160 gtg tgg ggg gct acc agc gcc atg gca acc ggc tat gtt aaa gtc atc   528
 V   W   G   A   T   S   A   M   A   T   G   Y   V   K   V   I    176 ttc ttt tgt ctt gga ttg tgc tat ggc gcg aac aca ttt ttt cac gcc   576
 F   F   C   L   G   L   C   Y   G   A   N   T   F   F   H   A    192 gcc aaa gca tat atc gag ggt tat cat act gtg cca aag ggt cgg tgc   624
 A   K   A   Y   I   E   G   Y   H   T   V   P   K   G   R   C    208 cgc cag gtc gtg acc ggc atg gca tgg ctg ttt ttc gtg agc tgg ggt   672
 R   Q   V   V   T   G   M   A   W   L   F   F   V   S   W   G    224 atg ttc cca att ctc ttc att ttg ggg ccc gaa ggt ttt ggc gtc ctg   720
 M   F   P   I   L   F   I   L   G   P   E   G   F   G   V   L    240 agc gtc tat ggc tcc acc gta ggt cac acg att att gat ctg atg agt   768
 S   V   Y   G   S   T   V   G   H   T   I   I   D   L   M   S    256 aaa aat tgt tgg ggg ttg ttg gga cac tac ctg cgc gtc ctg atc cac   816
 E   H   I   L   I   H   G   D   I   R   K   T   T   K   L   N    272 gag cac ata ttg att cac gga gat atc cgc aaa acc acc aaa ctg aac   864
 I   G   T   E   I   E   V   E   T   L   V   E   D   E   A         288
```

```
atc ggc gga acg gag atc gag gtc gag act ctc gtc gaa gac gaa gcc      912
 I   G   G   T   E   I   E   V   E   T   L   V   E   D   E   A      304 gag gcc gga gcc gtg cca taa                                          933
 E   A   G   A   V   P   stop                                        310
```

AAV Vector Injection

All of the animal experiments were at the institutional level and were in accord with the NIH Guide for the Care and Use of Laboratory Animals.

Newborn (P1) rat pups (Sprague-Dawley and Long-Evans) and mouse pups (C57BL/6J and C3H/HeJ or rd1/rd1) were anesthetized by chilling on ice. Adult mice (rd1/rd1) were anesthetized by IP injection of ketamine (100 mg/kg) and xylazinc (10 mg/kg). Under a dissecting microscope, an incision was made by scissors through the eyelid to expose the sclera. A small perforation was made in the sclera region posterior to the lens with a needle and viral vector suspension of 0.8-1.5 µl at the concentration of approximately $10^{11}$ genomic particles/ml was injected into intravitreal space through the hole with a Hamilton syringe with a 32-gauge blunt-ended needle. For each animal, usually only one eye was injected with viral vectors carrying Chop2-GFP and the other eye was uninjected or injected with control viral vectors carrying GFP alone. After the injection, animals were kept on a 12/12 hr light/dark cycle. The light illumination of the room housing the animals measured at the wavelength of 500 nm was $6.0\times10^{14}$ photons cm$^{-2}$ s$^{-1}$.

Histology

Animals were sacrificed at various time points after the vector injection. The expression of Chop2-GFP fluorescence was examined in flat whole-mount retinas, vertical retinal, and coronal brain sections. The dissected retinas and brains were fixed with 4% paraformaldehyde in PBS for 0.5-2 hr at room temperature and 24 hr at 4° C., respectively. The fixed retinas (embedded in 3% agarose) and brains were cut by using a vibratome. The retinal and brain sections or the retinal whole mounts were mounted on slides and covered with Vectashield medium (Vector Laboratories). GFP fluorescence was visualized under a fluorescence microscope equipped with exciter, dichroic, and emission filters of 465-495 nm, 505 nm, and 515-555 nm, respectively, and most images were obtained with a digital camera (Axiocam, Zeiss). Some images were obtained with a confocal microscope (TCS SP2, Leica). For light microscopy of semithin vertical retinal section, eyes were enucleated, rinsed in PBS, and fixed in 1% osmium tetroxide, 2.5% glutaraldehyde, and 0.2 M Sorenson's phosphate buffer (pH 7.4) at 4° C. for 3 hr. The eyes were then dehydrated in graded ethanols and embedded in plastic and cut into 1 µm sections and stained with a methylene blue/azure mixture.

Patch-Clamp Recordings

Dissociated retinal cells and retinal slice were prepared as previously described (Pan, 2000 and Cui et al., 2003). Recordings with patch electrodes in the whole-cell configuration were made by an EPC-9 amplifier and PULSE software (Heka Electronik, Lambrecht, Germany). Recordings were made in Hanks' solution containing (in mM): NaCl, 138; NaHCO$_3$, 1; Na$_2$HPO$_4$, 0.3; KCl, 5; KH$_2$PO$_4$, 0.3; CaCl$_2$, 1.25; MgSO$_4$, 0.5; MgCl$_2$, 0.5; HEPES-NaOH, 5; glucose, 22.2; with phenol red, 0.001% v/v; adjusted to pH 7.2 with 0.3 N NaOH.

The electrode solution contained (in mM): K-gluconate, 133; KCl, 7; MgCl$_2$, 4; EGTA, 0.1; HEPES, 10; Na-GTP, 0.5; and Na-ATP, 2; pH adjusted with KOH to 7.4. The resistance of the electrode was 13 to 15 Ma The recordings were performed at room temperature (~22° C.).

Multielectrode Array Recordings

The multielectrode array recordings were based on the procedures reported by Tian and Copenhagen (2003). Briefly, the retina was dissected and placed photoreceptor side down on a nitrocellulose filter paper strip (Millipore Corp., Bedford, Mass.). The mounted retina was placed in the MEA-60 multielectrode array recording chamber of 30 µm diameter electrodes spaced 200 µm apart (Multi Channel System MCS GmbH, Reutlingen, Germany), with the ganglion cell layer facing the recording electrodes. The retina was continuously perfused in oxygenated extracellular solution at 34° C. during all experiments. The extracellular solution contained (in mM): NaCl, 124; KCl, 2.5; CaCl$_2$, 2; MgCl$_2$, 2; NaH$_2$PO$_4$, 1.25; NaHCO$_3$, 26; and glucose, 22 (pH 7.35 with 95% O$_2$ and 5% CO$_2$). Recordings were usually started 60 min after the retina was positioned in the recording chamber. The interval between onsets of each light stimulus was 10-15 s. The signals were filtered between 200 Hz (low cut off) and 20 kHz (high cut off). The responses from individual neurons were analyzed using Offline Sorter software (Plexon, Inc., Dallas, Tex.).

Visual-Evoked Potential Recordings

Visual-evoked potential recordings were carried out in wild-type mice of the C57BL/6 and 129/Sv strains aged 4-6 months and in the rd1/rd1 mice aged 6-11 months. Recordings were performed 2-6 months after viral vector injection.

After general anesthesia (i.p. injection of ketamine (100 mg/kg) and acepromazine (0.8 mg/kg), animals were mounted in a stereotaxic apparatus. Body temperature was either unregulated or maintained at 34° C. with a heating pad and a rectal probe. Pupils were dilated with 1% atropine and 2.5% accu-phenylephrine. A small portion of the skull (~1.5×1.5 mm) centered about 2.5 mm from the midline and 1 mm rostral to the lambdoid suture was drilled and removed. Recordings were made from visual cortex (area V1) by a glass micropipette (resistance ~0.5 M after filling with 4 M NaCl) advanced 0.4 mm beneath the surface of the cortex at the contralateral side of the stimulated eye. The stimuli were 20 ms pluses at 0.5 Hz. Responses were amplified (1,000 to 10,000), band-pass filtered (0.3-100 Hz), digitized (1 kHz), and averaged over 30-250 trials.

Light Stimulation

For dissociated cell and retinal slice recordings, light stimuli were generated by a 150 W xenon lamp-based scanning monochromator with bandwidth of 10 nm (TILL Photonics, Germany) and coupled to the microscope with an optical fiber. For multielectrode array recordings, light responses were evoked by the monochromator or a 175 W xenon lamp-based illuminator (Lambda LS, Sutter Instrument) with a band-pass filter of 400-580 nm and projected to the bottom of the recording chamber through a liquid light guider. For visual evoked potential, light stimuli were generated by the monochromator and projected to the eyes through the optical fiber. The light intensity was attenuated by neutral density filters. The light energy was measured by a thin-type sensor (TQ82017) and an optical power meter (Model: TQ8210) (Advantest, Tokyo, Japan).

Example 2

Expression of Chop2 in Retinal Neurons In Vivo

To directly visualize the expression and localization of Chop2 proteins, the C-terminal portion of the Chop2 channel was replaced with GFP, to make a Chop2-GFP chimera. The adeno-associated virus (AAV) vectors was selected to target the expression of Chop2-GFP fusion protein into retinal neurons because the capability of AAV vectors to deliver transgenes into nondividing cells, including inner retinal neurons (Harvey et al., 2002 and Martin et al., 2003), and to integrate the transgenes into the host genome (Flotte, 2004).

A viral expression cassette, rAAV2-CAG-Chop2-GFP-WPRE, was made by subcloning the Chop2-GFP chimera into an AAV serotype-2 expression cassette containing a hybrid CMV enhancer/chicken β-actin (CAG) promoter (FIG. 1A). To establish the expression and function of Chop2 channels in retinal neurons in general, we first examined the expression of Chop2 in nondystrophic retinas. The viral vector was injected into the intravitreal space in the eyes of postnatal day 1 rats and mice. Three to four weeks after the injection, bright GFP fluorescence was observed in retinal neurons of all injected eyes (FIGS. 1B-1H), confirming that Chop2-GFP was expressed. The expression was usually confluent throughout the retina (FIG. 1B).

The Chop2-GFP-fluorescence was predominantly observed in retinal ganglion cells (FIGS. 1C and 1D; also see FIG. 1H). The fluorescence signal was observed throughout the inner plexiform layer (IPL) (FIG. 1H), indicating that the viral vector targeted the expression of Chop2-GFP both in ON and OFF ganglion cells. The expressing of Chop2-GFP was also frequently observed in horizontal cells (FIG. 1E), amacrine cells (FIG. 1F), and, occasionally, in bipolar cells (FIG. 1G).

The GFP signal was predominantly localized to the plasma membrane (FIG. 1D), consistent with the GFP tag being anchored to the membrane by a seven-transmembrane portion of the Chop2 channel. Once expressed in a cell, the GFP signal was extended over the entire cell including distal processes and axon terminals (see FIGS. 1C and 1E). Bright GFP fluorescence was found to be stable for 12 months or more after the injection (FIG. 1H), whereas no gross changes in retinal morphology were noticed (FIG. 1I). These results indicated that long-term stable expression of Chop2-GFP was achieved in inner retinal neurons in vivo.

Example 3

Properties of Light-Evoked Currents of ChR2-Expressing Inner Retinal Neurons

Functional properties of the Chop2 channels were examined in inner retinal neurons by using whole-cell patch-clamp recordings. The recordings were performed in acutely dissociated cells so that photoreceptor-mediated light responses were confidently excluded. Chop2-GFP-positive cells were identified by their GFP fluorescence (FIG. 2A). The precursor for the Chop2 chromophore group, all-trans retinal, was not added because it might be ubiquitously present in cells (Kim et al., 1992 and Thompson and Gal, 2003). Light-evoked responses were observed in all recorded GFP fluorescent cells (n=34), indicating that functional ChR2 (Chop2 with the chromophore attached) can be formed in retinal neurons with the retinal chromophore groups already present in the cells. Consistently, the expression of functional ChR2 channels has also been recently reported in cultured hippocampal neurons without the supply of exogenous retinal chromophore groups (Boyden et al., 2005; but see Li et al., 2005).

Figure 2B:
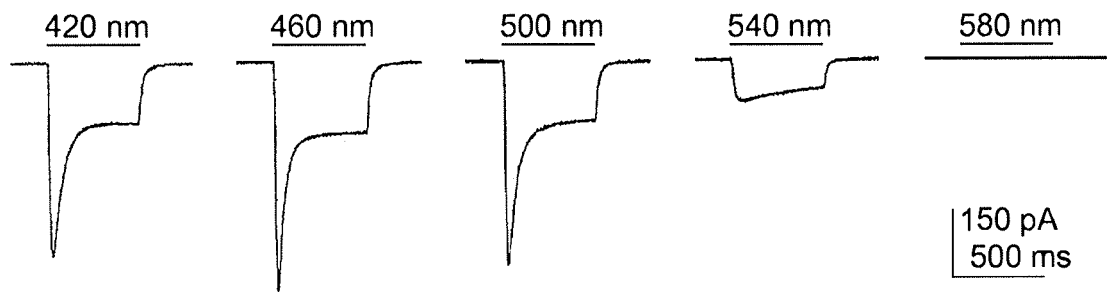
Figure 2C:
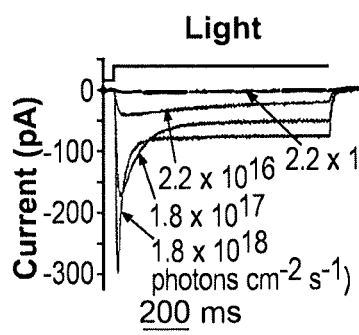
Figure 2D:
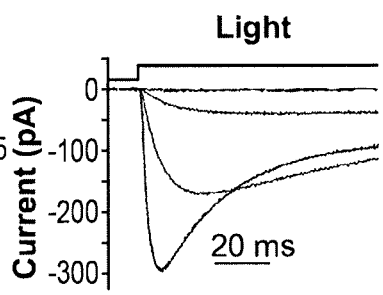
Figure 2E:
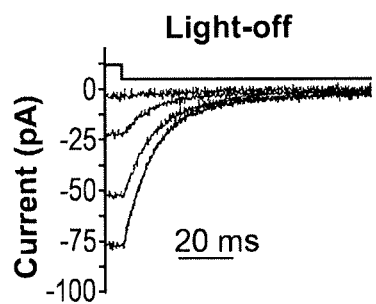
Figure 2F:
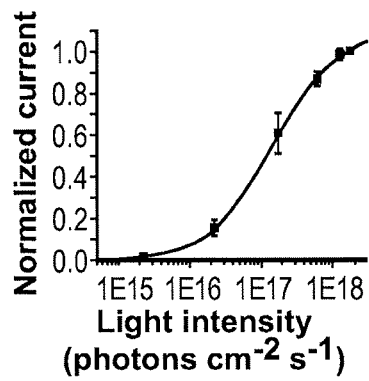
Figure 2G:
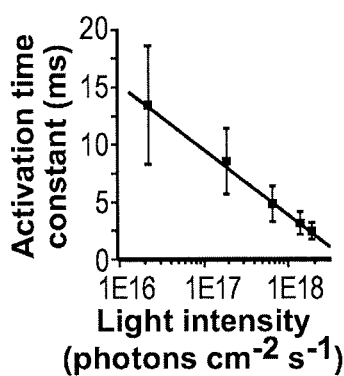
Figure 2H:
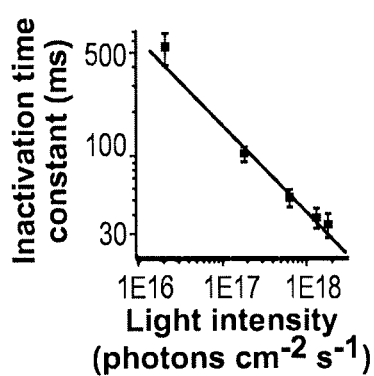

The properties of the ChR2-mediated light responses were first examined in voltage clamp. Light-evoked currents were observed in Chop2-GFP-expressing inner retinal neurons by light stimuli up to the wavelength of 580 nm with the most sensitive wavelength around 460 nm (FIG. 2B), consistent with the reported peak spectrum sensitivity of ChR2 (Nagel et al., 2003). The amplitude and the kinetics of the currents were dependent on the light intensity (FIG. 2C). FIGS. 2D and 2E show in the expanded time scale the current traces right after the onset and the termination of the light stimulation, respectively. Detectable currents were observed in most recorded cells at a light intensity of $2.2 \times 10^{15}$ photons $cm^{-2}$ $s^{-1}$. In some cells, currents were observed at a light intensity of $2 \times 10^{14}$ photons $cm^{-2}$ $s^{-1}$ (not shown). At higher light intensities, the currents displayed both transient and sustained components, similar to the properties of the non-fusion ChR2 (Nagel et al., 2003). The relationship between the light intensity and peak current is shown in FIG. 2F (n=7). The activation and inactivation kinetics of the currents were also dependent on the light intensity (FIG. 2D). The initial phase of the current could be well fitted by an exponential function with a single activation and inactivation constant, as illustrated in FIG. 2D (red trace). The activation and inactivation time constants versus light intensity are plotted in FIGS. 2G and 2H, respectively. On the other hand, the deactivation kinetics of the currents after the light off was not light-intensity dependent. The current decay trace could be well fitted by a single exponential function as shown in FIG. 2E (red trace). The time constant was 17.1±6.5 ms (mean±SD, n=7).

Figure 3A:
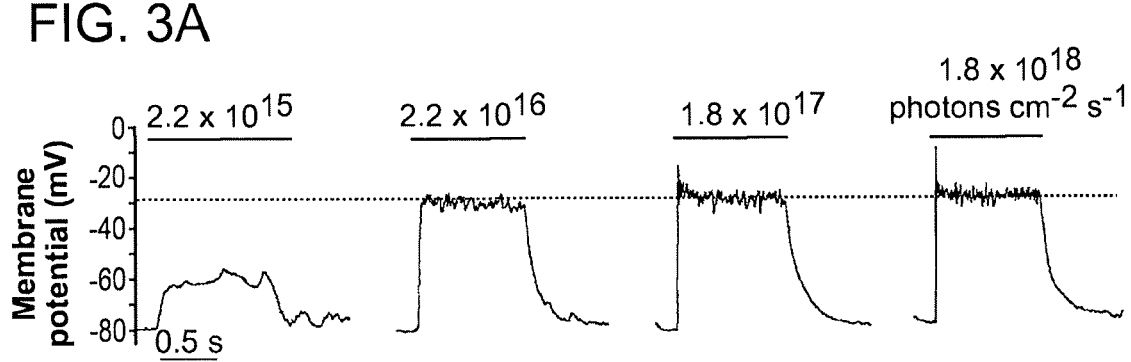
FIGS. 3A-3C. Properties of Light-Evoked Voltage Responses of ChR2-Expressing Retinal Neurons.
Figure 3B:
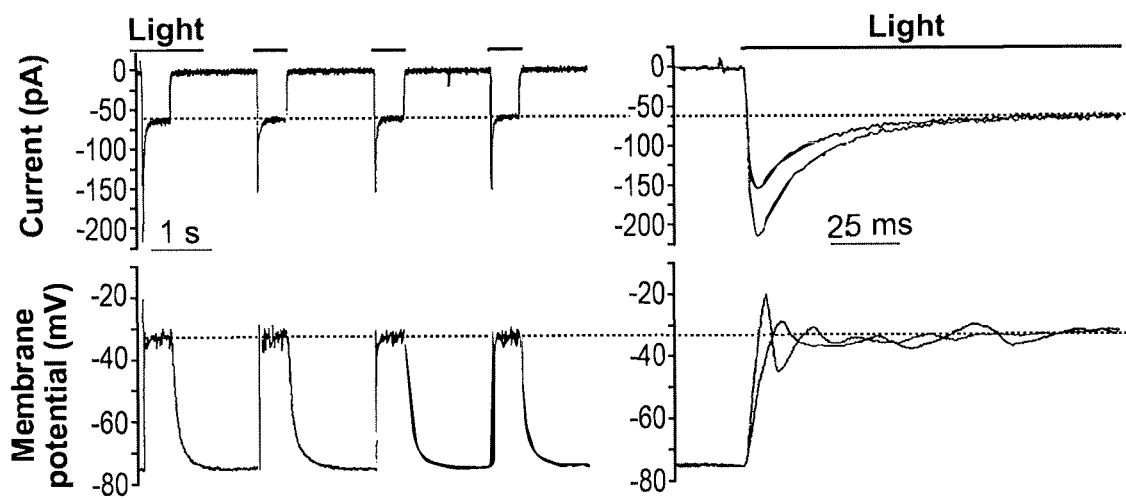
Figure 3C:
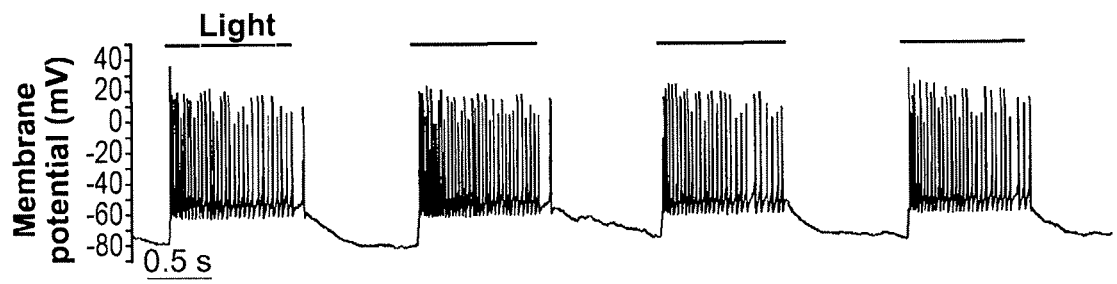

The next experiment examined whether the ChR2-mediated currents were sufficient to drive membrane depolarization. FIG. 3A shows the representative responses from a nonspiking neuron in response to four incremental light intensities at the wavelength of 460 nm. Detectable responses were observed in most recorded cells at a light intensity of $2.2 \times 10^{15}$ photons $cm^{-2}$ $s^{-1}$. At higher light intensities, the membrane depolarization approached a saturated level. The ChR2-mediated light responses to repeated light stimulations were further examined. The transient component of the currents diminished to repeated stimulations whereas the sustained component of the currents was stable (top traces in FIG. 3B). This was clearly seen in the expanded time scale in the right panel of FIG. 3B by comparing the superimposed first (red trace) and the second (black trace) light-evoked currents. For the same cell, in current clamp, the stimulations evoked robust membrane depolarizations (bottom traces in FIG. 3B). The membrane depolarizations reached an almost identical level, except for the initial portion of the response. This was also shown in the expanded time scale (right panel), which superimposed the first (red trace) and the second (black trace) light-evoked responses. FIG. 3C shows a representative recording of spiking neurons to repeated light stimulations. Again, the stimulations elicited almost identical membrane depolarizations accompanied by multiple spikes. Taken together, these results demonstrated that the ChR2-mediated currents in second- and third-order retinal neurons are sufficient to drive membrane depolarization and/or spike firing.

Example 4

Expression of Chop2 in Photoreceptor-Deficient rd1/rd1 Mice

Figure 4A:
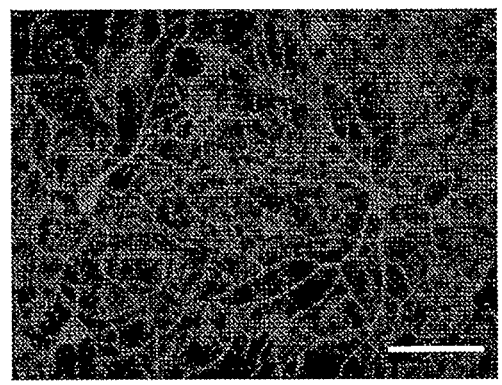
Figure 4B:
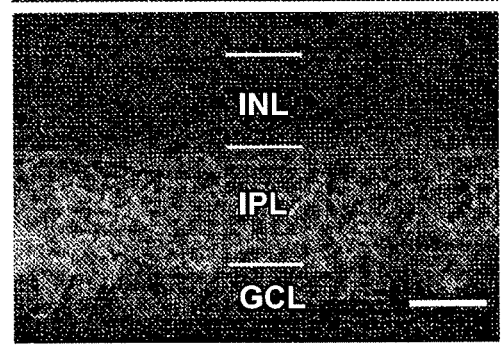
Figure 4C:
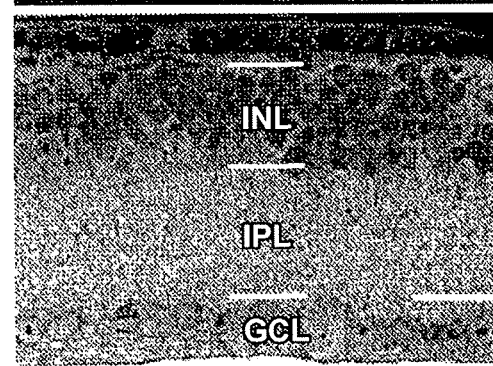

Having established the expression and function of ChR2 in wild-type retinas, we went on to address whether the expression of ChR2 could restore light responses in retinas after photoreceptor degeneration. To this end, the experiments were carried out in homozygous rd1 (rd1/rd1) mice (Bowes et al., 1990), a photoreceptor degeneration model with a null mutation in a cyclic GMP phosphodiesterase, PDE6, similar to some forms of retinitis pigmentosa in humans (McLaughlin et al., 1993). The Chop2-GFP viral vector was injected intravitreally into the eyes of newborn (P1) or adult mice at 2-12 months of age. Similar to the results observed in wild-type animals, bright GFP signal was observed in Chop2-GFP-injected retinas, predominately in retinal ganglion cells (FIGS. 4A and 4B). At the time of the recording experiments (>4 months of age unless otherwise indicated), photoreceptor cells were absent (FIG. 4C). The expression of Chop2-GFP was observed in the rd1/rd1 mice up to 16 months of age (3-6 months after the viral injection) as the case shown in FIG. 4A from a 15 month old rd1/rd1 mouse. These results indicate that inner retinal neurons in this photoreceptor-deficient model not only survive long after the complete death of photoreceptors but also retain the capability of stable expression of Chop2-GFP.

Example 5

Light-Evoked Responses of ChR2-Expressing Surviving Inner Retinal Neurons of rd1/rd1 Mice The light response properties of the ChR2-expressing retinal neurons in rd1/rd1 mice were examined by whole-cell patch-clamp recording in retinal slices. The recordings were made from the GFP-positive cells located in the ganglion cell layer. Light-evoked currents were observed in GFP-positive cells. The magnitude of the current was again dependent on the light intensity (top traces in FIGS. 4D and 4E; also see light intensity and current relationships shown in FIG. 4F). Two groups of ChR2-expressing retinal neurons were observed based on their response properties: a group of transient spiking neurons (FIG. 4D) and a group of sustained spiking neurons (FIG. 4E). The membrane depolarization and/or spike rates were also dependent on the light intensity (bottom traces in FIGS. 4D and 4E). Furthermore, light at higher intensities markedly accelerated the kinetics of the voltage responses as illustrated in the right panels of FIGS. 4D and 4E by superimposing the second traces (black) and the fourth traces (red) in an expanded time scale. The relationships of light intensity to the membrane depolarization, the spike firing rate, and the time to the first spike peak are shown in FIGS. 4G, 4H, and 4I, respectively. These results demonstrate that the surviving retinal third-order neurons with the expression of ChR2 are capable of encoding light intensity with membrane depolarization and/or action potential firing and response kinetics.

Example 6

Multielectrode Array Recordings of ChR2-Mediated Retinal Activities

The spike coding capability of the photoreceptor-deficient retina of rd1/rd1 mice were examined after the expression of ChR2 by use of multielectrode array recordings from whole-mount retinas. As shown from a sample recording in FIG. 5A, spike firings with fast kinetics in response to light on and off were observed in Chop2-GFP-expressing retinas (n=11 retinas). The light-evoked spike firings were not affected by the application of CNQX (25-50 µM) plus APV (25-50 µM) (n=3), indicating that the responses are originated from the ChR2 of the recorded cells. No such light-evoked spike firings were observed in retinas that were either injected with viral vectors carrying GFP alone (n=2 retinas) or left uninjected (n=3). The latter confirmed the absence of photoreceptor-originated light responses. The light-evoked spike firings were not affected by suramine (100 µM) (n=2), which has been reported to be able to block melanopsin receptor-mediated photocurrent (Melyan et al., 2005 and Qiu et al., 2005).

Figure 5A:
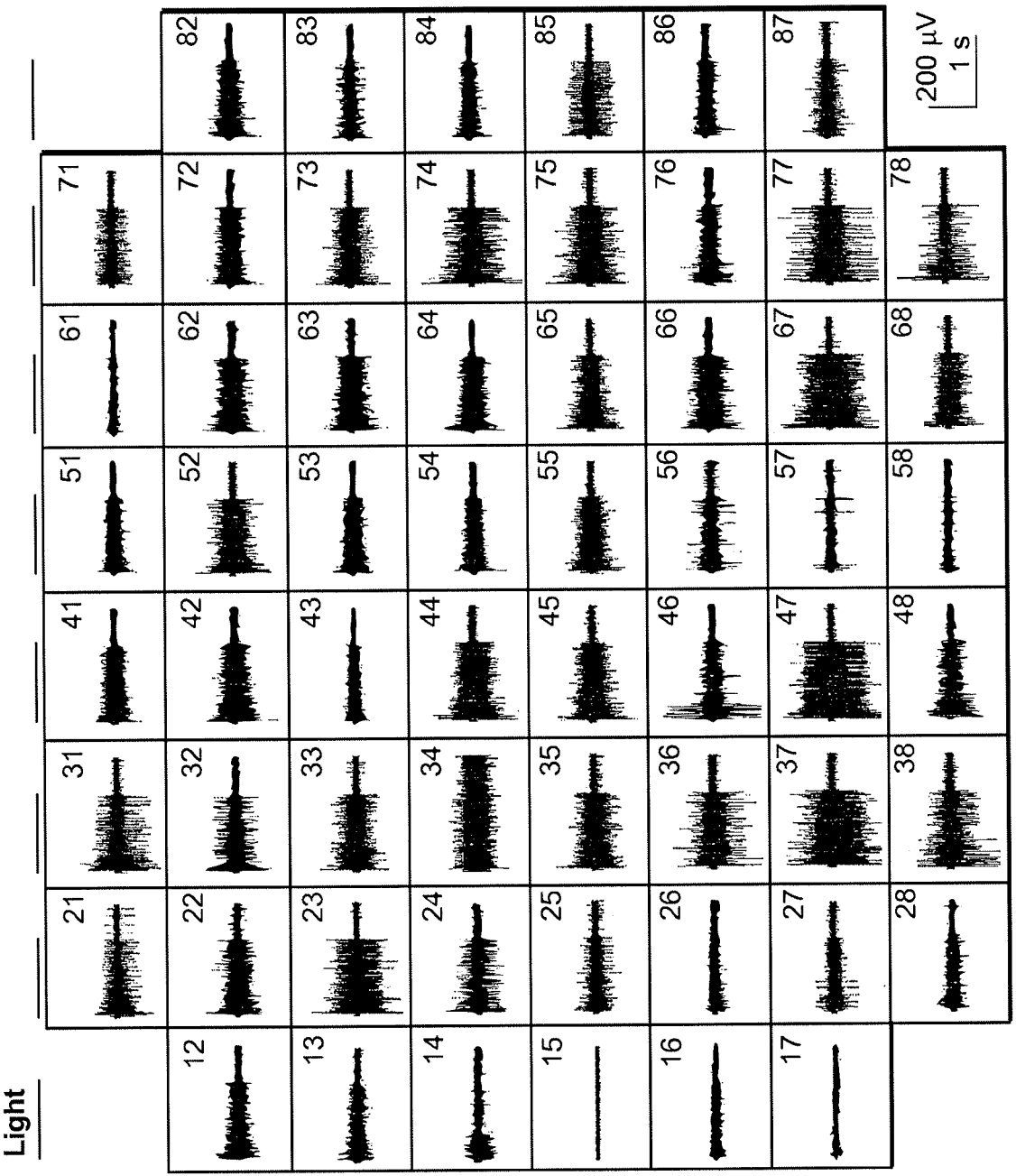

In addition, the response kinetics to both light on and off (see FIG. 5B) were much faster than those generated by the intrinsically photosensitive retinal ganglion cells (Tu et al., 2005). These results indicated that a significant contribution to the observed light responses from the intrinsically photosensitive ganglion cells under our recording conditions is unlikely. The light-evoked responses were often found to be picked up by the majority of the electrodes (see FIG. 5A), consistent with the observation that Chop2-GFP was extensively expressed in the retinas. The vast majority of the responses were sustained during light stimulation. FIG. 5B illustrates the raw traces recorded by a single electrode in response to three incremental light stimuli. The raster plots of the spike activity sorted from a single neuron of the recording were shown in FIG. 5C. The firing frequency was remarkably stable during the course of the recording. The averaged spike rate histograms are shown in FIG. 5D. Again, the spike frequency was increased to the higher light intensity. The light responses could be recorded for up to 5 hr. These results demonstrate further that the ChR2-expressing retinal ganglion cells can reliably encode light intensity with spike firing rate.

Example 7

Visual-Evoked Potentials

Figure 6C:
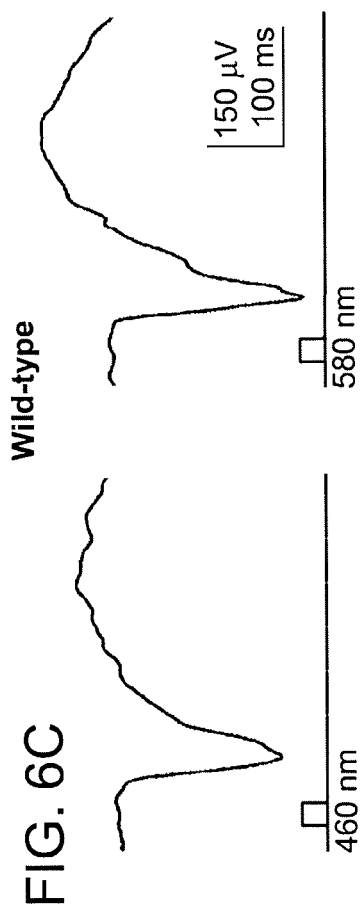
FIG. 6A-6E. Central Projections of Chop2-GFP-Expressing Retinal Ganglion Cells and Visual-Evoked Potentials in rd1/rd1 Mice.
Figure 6D:
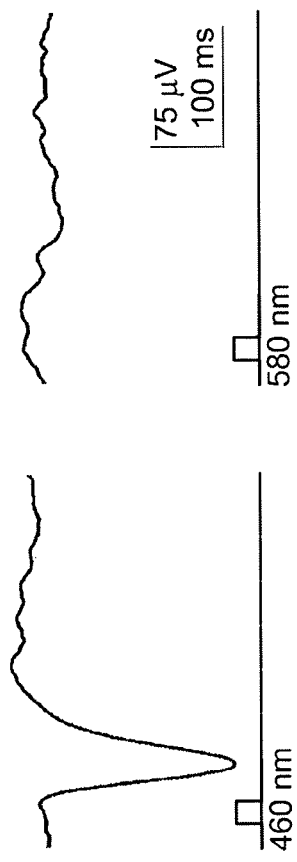
Figure 6E:
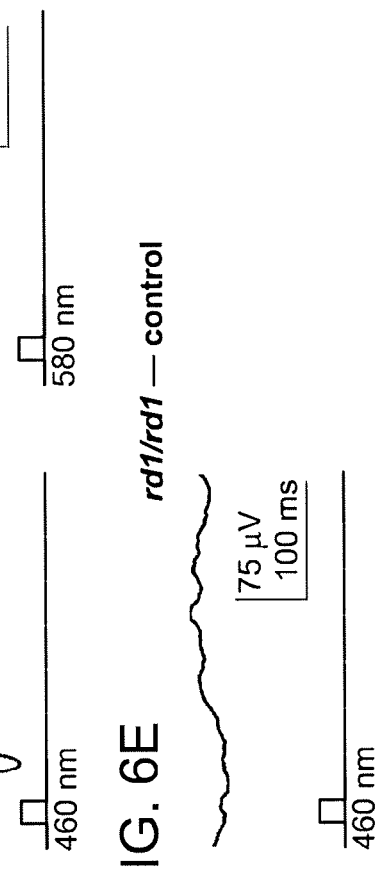
Figure 6A:
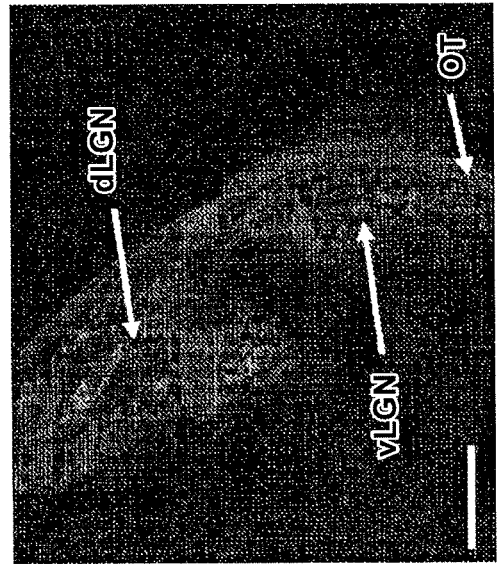
Figure 6B:
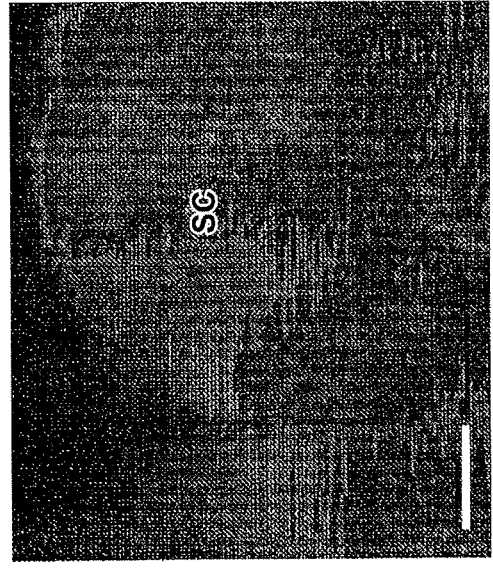
Figure 6G:
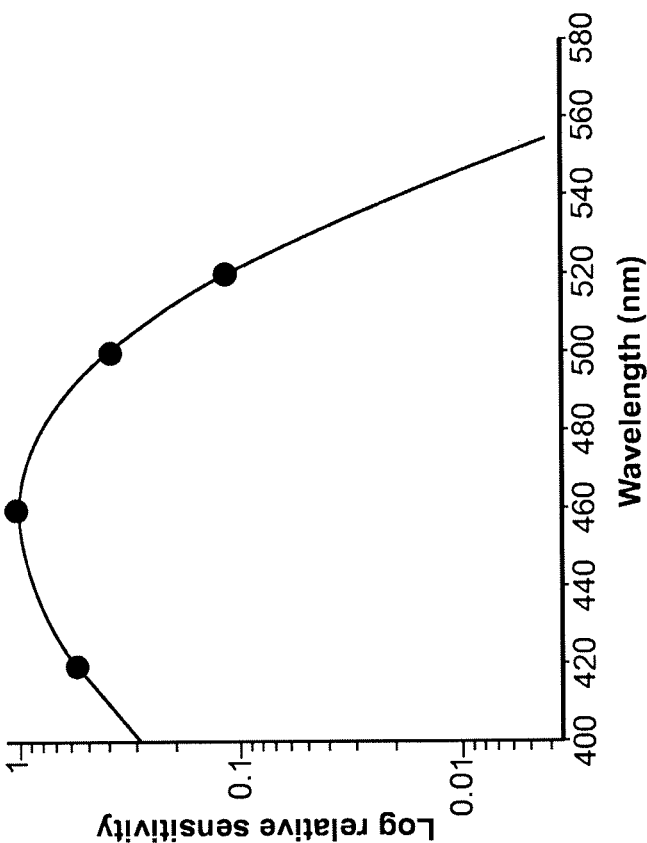
(FIG. 6G) The sensitivity data points were fitted by a vitamin-$A_1$-based visual pigment template with a peak wavelength of 461 nm.
Figure 6F:
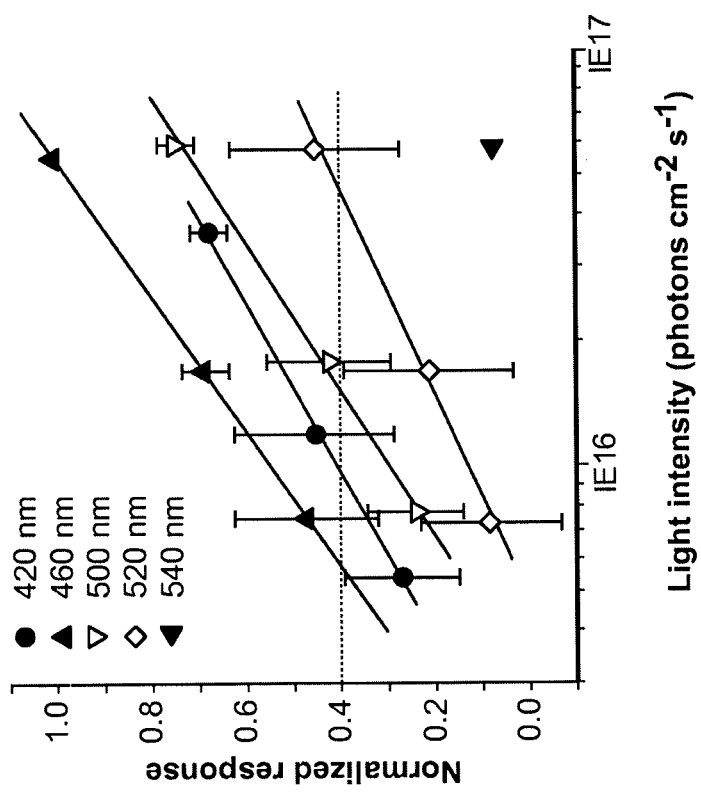
(FIG. 6F) Plot of the amplitude of VEPs from rd1/rd1 mice injected with Chop2-GFP viral vectors to various light intensities at the wavelengths of 420, 460, 500, 520, and 540 nm. For each eye, the responses are normalized to the peak response obtained at 460 nm. The data are the mean±SD (n=3 eyes). Spectral sensitivity at each wavelength was defined as the inverse of the interpolated light intensity to produce 40% of the normalized peak response, as indicated by the dot line.

A study was conducted to test whether the ChR2-mediated light responses in the retinas of rd1/rd1 mice were transmitted to the visual cortex. The expression of transgenes, such as GFP, in retinal ganglion cells as achieved by AAV infection was reported to be able to extend to their terminations in higher visual centers in the brain (Harvey et al., 2002). Therefore the anatomical projections of the axon terminals of Chop2-GFP-expressing retinal ganglion cells were first examined. Consistently, Chop2-GFP labeled axon terminals of retinal ganglion cells were observed in several regions of the brain, including ventral lateral geniculate nucleus and dorsal lateral geniculate nucleus (FIG. 6A), as well as superior colliculus (FIG. 6B). These results indicate that the central projections of retinal ganglion cells in the degenerate retinas are maintained.

Visual evoked potentials (VEPs) from visual cortex were then examined. First, as illustrated in FIG. 6C, VEPs were observed in all tested wild-type mice (4-6 months of age) in response to light stimuli at the wavelengths of both 460 and 580 nm (n=6 eyes). When tested in Chop2-GFP-injected eyes of rd1/rd1 mice (6-11 months of age), VEPs were observed in the majority of the eyes (nine out of 13) in response to light stimulus at the wavelength of 460 nm but not to light stimulus at the wavelength of 580 nm (FIG. 6D), consistent with the light sensitivity of ChR2 channels (see FIG. 2B). The average amplitude of the VEPs in the Chop2-GFP-injected eyes in response to the light stimulus at the wavelength of 460 nm was 110±34 µV (mean±SE; n=10), which is smaller than that observed in wild-type mice (274±113 µV; n=6), although these two values are not significantly different (one-way ANOVA test, p<0.1). The lower amplitudes of the VEPs in the Chop2-transfected mice compared to the wild-type mice are not surprising because the expression of ChR2 was probably only achieved in a small portion of the retinal ganglion cells. The average latency to the peak of the VEPs in the Chop2-GFP-injected eyes was 45±1.7 ms (n=10), which is shorter than that observed in wild-type mice (62+2.8 ms; n=6). These two values were significantly different (p<0.01). The latter would be predicted because the light response mediated by ChR2 in retinal ganglion cells originates two synapses downstream of the photoreceptors. As a control, no detectable VEPs were observed to light stimulus at the wavelength of 460 nm in the eyes of the age-matched rd1/rd1 mice that were injected with viral vectors carrying GFP alone (n=5) (FIG. 6E). In addition, no detectable VEPs were observed in uninjected rd1/rd1 mice (n=3; 5 months of age) to the wavelengths ranging from 420 to 620 nm (not shown), confirming that rd1/rd1 mice at ≥5 months of age are completely blind based on VEPs.

To further ensure that the VEPs in the blind rd1/rd1 mice originate from ChR2 expressed in their retinas, the action spectrum of the VEP were measured by plotting their normalized amplitudes in response to varying light wavelengths and intensities to obtain the relative sensitivity of the response (FIG. 6F) (n=3). The data points were well fitted by a vitamin-$A_1$-based visual pigment template (Partridge and De Grip, 1991) with a peak wavelength at 461 nm (FIG. 6G), a good match to the reported peak action spectrum of ChR2 at ~460 nm (Nagel et al., 2003). Taken together, these results demonstrated that expression of ChR2 in the photoreceptor-deficient retinas can restore visually evoked responses in the brain.

Example 8

Discussion of Examples 1-7

The results presented herein demonstrated that the strategy of restoration of light responses in photoreceptor-deficient rodent retinas based on the expression of ChR2 is mechanistically and technically feasible. Most importantly, the results showed that ChR2 satisfies several major criteria for its use as a light sensor in retinal neurons. First, by delivery of an AAV vector carrying fused Chop2-GFP, the inventors showed the ability of retinal neurons to tolerate the prolonged expression of Chop2. To date, the expression of Chop2-GFP proteins had been achieved in nondystrophic rat retinal neurons for 12 months and in photoreceptor deficient rd1/rd1 mice for 6 months in vivo after the viral injection. The present results therefore indicate that the expression of ChR2 in retinal neurons is biocompatible under normal light cycle conditions.

Second, these results showed that a sufficient number of ChR2 can be formed in retinal neurons, with only endogenous chromophore groups as supplied by regular diet, to produce robust membrane depolarizations and/or action potential firings in the retina and VEPs in visual cortex. It is worth emphasizing here that, unlike animal visual pigments that rapidly lose their chromophore after its photoisomerization from 11-cis to all-trans retinal (Wald, 1968), for microbial-type rhodopsins, photoisomerization from all-trans to 11-cis retinal is reversible and both isomers remain attached to the protein (Oesterhelt, 1998). Once the ChR2 complex is formed, the light-sensitive channel can sustain multiple cycles of photoisomerization with the same chromophore moiety. Although the efficacy of the de novo ChR2 formation might be expected to depend on the availability of the chromophore group, the need for constant resupply of the chromophore to form new ChR2 does not appear to impose a limitation on overall ChR2 function. As observed in the multielectrode array recordings, ChR2 respond repeatedly to light stimulation for several hours in vitro without loss of activity. These results thus indicate that the turn-over rate for ChR2 is fairly slow, an additional advantage for use as an artificially produced light sensor.

Furthermore, as reported originally in cell expression systems (Nagel et al., 2003), later in hippocampal neurons (Boyden et al., 2005, Ishizuka et al., 2006 and Li et al., 2005), and now shown in retinal neurons, a number of properties of the ChR2 channel are highly advantageous for its use as a light sensor.

First, the ChR2 channel is permeable to the cations that underlie neuronal membrane excitability. Thus, activation of ChR2 channels by light can directly produce membrane depolarizations to mimic the ON-responses of inner retinal neurons. Indeed, as shown herein, the light-evoked responses mediated by ChR2 in nonspiking and spiking retinal neurons remarkably resemble the light responses of ON-bipolar cells and sustained ON-ganglion cells (Werblin and Dowling, 1969 and Kaneko, 1970).

Second, the activation kinetics of the current in response to light are extremely fast, whereas the sustained components of the currents do not show apparent inactivation to continuous or repeated light illuminations. Thus, the ChR2-expressing neurons can signal with rapid kinetics but without pigment inactivation. Consistently, the expression of ChR2 has been shown to allow optical control of neural excitability with high temporal resolution (Boyden et al., 2005, Ishizuka et al., 2006 and Li et al., 2005). Furthermore, it is shown here that the magnitude and activation kinetics of the light-evoked current depend upon light irradiance over a 3-log-unit range. As demonstrated in the whole-cell and multielectrode array recordings, this would allow the encoding of various light intensities with graded membrane depolarizations and/or spike rates.

Also of importance for the feasibility of the strategy of restoring light sensitivity in retinas after photoreceptor degeneration, results of this study show that many inner retinal neurons survive in aged rd1/rd1 mice (up to 16 months of age) and are capable of expressing ChR2 long after the death of all photoreceptors. This is consistent with histological studies showing that many inner retinal neurons survive, despite some remodeling, in this mouse model (Jimenez et al., 1996, Strettoi and Pignatelli, 2000 and Chang et al., 2002). Moreover, the present studies using ChR2 showed that the surviving inner retinal neurons retained their physiological capability to encode light signals with membrane depolarizations and/or action potential firings and to transmit visual signals to the visual cortex. Thus, the strategy based on the expression of ChR2 is suitable at least for certain retinal degenerative diseases at certain stages.

The remodeling of inner retinal neurons triggered by photoreceptor degeneration raised some concerns for the retinal-based rescue strategy after the death of photoreceptors (Strettoi and Pignatelli, 2000, Jones et al., 2003 and Jones and Marc, 2005). However, retinal degenerative diseases are heterogeneous as to the time course of the degeneration, survival and functional state of different cell types (Chang et al., 2002). The use of ChR2 is a powerful tool for undertaking such studies.

Retinal remodeling is believed to be caused by deafferentation (Jones and Marc, 2005). Therefore, the restoration of the light sensitivity in inner retinal neurons may be able to prevent or delay the remodeling processes.

Finally, according to the present invention, viral-based gene delivery systems, such as AAV vectors (Flannery et al., 1997, Bennett et al., 1999, Ali et al., 2000 and Acland et al., 2001), are tools for introducing Chop2 into retinal neurons as demonstrated herein.

The present results showed that that viral construct with AAV serotype-2 and CAG promoter achieved robust expression of Chop2 in ganglion cells. However, because the expression of Chop2 with this construct appears to target both ON- and OFF-type ganglion cells, it remains to be determined how the conversion of both ON- and OFF-ganglion cells into ON-type affects the visual perception.

Behavior studies in primates reported that pharmacological blockade of the ON channel in the retina did not severely impair such vision functions as the detection of light decrement and the perception of shape (Schiller et al., 1986). Therefore, targeting of ChR2 to the ON channel, for example to ON-type ganglion cells, is expected to result in useful vision.

It is also contemplated herein to express ChR2 in the more distal retinal neurons, such as bipolar cells; this approach would utilize the remaining signal processing functions of the degenerate retina. Targeting ChR2 to rod bipolar cells is particularly attractive because the depolarization of rod bipolar cells can lead to the ON and OFF responses at the levels of cone bipolar cells and retinal ganglion cells (Wässle, 2004), thereby maintaining the ON and OFF channels that are inherent in the retina.

The threshold light intensity required for producing responses in ChR2-expressing retinas appeared to be near $10^{14}$-$10^{15}$ photons cm$^{-2}$ s$^{-1}$. For comparison, the thresholds for normal rod and cone photoreceptors are about $10^{6}$ and $10^{10}$ photons cm$^{-2}$ s$^{-1}$, respectively (Dacey et al., 2005). Therefore, the ChR2-expressing retinas would operate in substantially higher photonic range. The relatively low light sensitivity of the ChR2-expressing retinas compared to the normal retinas could be due to a number of factors. First, there may be a low cross-sectional density of ChR2 molecules in the transfected retinal neurons compared with the visual pigments in rods and cones. Second, the ChR2-expressing inner retinal neurons lack the unique multilayer photoreceptor membrane organization, typical for the outer segments of rods and cones, which developed to achieve higher pigment density and thus increase the probability of catching photons (Steinberg, et al., 1980). Third, unlike visual pigments that propagate their signal through amplification cascade (Stryer, 1991), the directly light-gated ChR2 channels lack such amplification capabilities. Finally, in normal retinas, amplification of visual signals occurs as the signals converge from multiple photoreceptors to ganglion cells (Barlow et al., 1971). This process was not yet achieved in the ChR2-transfected retinas. It is not yet evident which of these factors contributes the most to the decreased light sensitivity of the ChR2-expressing retinas remains. Interestingly, ChR2 mediated phototaxis to low-intensity light in green algae (Sineshchekov et al., 2002; but see Kateriya et al. [2004]). Therefore, the light sensitivity of ChR2 in retinal neurons may have been altered by modifications introduced in the Chop2 molecule for the heterologous expression. Such a difference may also reflect different structural and functional organization of algae and mammalian cells.

Nevertheless, for clinical usage, light intensifying devices can be used to expand the light operation range.

At present, no treatment is available for restoring vision once the photoreceptor cells have been lost. As noted above, transplantation of normal photoreceptor cells or progenitor cells (Bok, 1993 and Lund et al., 2001) or direct electrical stimulation of the surviving second- and third-order retinal neurons via retinal implants (Zrenner, 2002) have been proposed as possible strategies for restoration of light responses in the retina after rod and cone degeneration. An important advantage of the present invention is that it does not involve the introduction of tissues or devices into the retina and, therefore, may largely avoid the complications of immune reactions and bioincompatibilities. In addition, the present approach is expected to achieve high spatial resolution for the restored "vision" because the approach targets the cellular level. Thus, the expression of microbial-type channel rhodopsins, such as ChR2, in surviving retinal neurons is a strategy for the treatment of complete blindness caused by rod and cone degeneration.

REFERENCES CITED IN EXAMPLES SECTIONS

Acland et al., 2001—G. M. Acland, G. D. Aguirre, J. Ray, Q. Zhang, T. S. Aleman, A. V. Cideciyan, S. E. Pearce-Kelling, V. Anand, Y. Zeng and A. M. Maguire et al., Gene therapy restores vision in a canine model of childhood blindness, *Nat. Genet.* 28 (2001), pp. 92 95

Ali et al., 2000—R. R. Ali, G. M. Sarra, C. Stephens, M. D. Alwis, J. W. Bainbridge, P. M. Munro, S. Fauser, M. B. Reichel, C. Kinnon and D. M. Hunt et al., Restoration of photoreceptor ultrastructure and function in retinal degeneration slow mice by gene therapy, *Nat. Genet.* 25 (2000), pp. 306-310

Auricchio et al., 2001—A. Auricchio, G. Kobinger, V. Anand, M. Hildinger, E. O'Connor, A. M. Maguire, J. M. Wilson and J. Bennett, Exchange of surface proteins impacts on viral vector cellular specificity and transduction characteristics: the retina as a model, *Hum. Mol. Genet.* 10 (2001), pp. 3075-3081

Banghart et al., 2004—M. Banghart, K. Borges, E. Isacoff, D. Trauner and R. H. Kramer, Light-activated ion channels for remote control of neuronal firing, *Nat. Neurosci.* 7 (2004), pp. 1381-1386

Barlow et al., 1971—H. B. Barlow, W. R. Levick and M. Yoon, Responses to single quanta of light in retinal ganglion cells of the cat, *Vision Res.* 3 (1971), pp. 87-101

Baylor, 1996—D. Baylor, How photons start vision, *Proc. Natl. Acad. Sci. USA* 93 (1996), pp. 560-565

Bennett et al., 1999—J. Bennett, A. M. Maguire, A. V. Cideciyan, M. Schnell, E. Glover, V. Anand, T. S. Aleman, N. Chirmule, A. R. Gupta and Y. Huang et al., Stable transgene expression in rod photoreceptors after recombinant adeno-associated virus-mediated gene transfer to monkey retina, *Proc. Natl. Acad. Sci. USA* 96 (1999), pp. 9920 9925

Bok, 1993—D. Bok, Retinal transplantation and gene therapy. Present realities and future possibilities, *Invest. Ophthalmol. Vis. Sci.* 34 (1993), pp. 473-476

Bowes et al., 1990—C. Bowes, T. Li, M. Danciger, L. C. Baxter, M. L. Applebury and D. B. Farber, Retinal degeneration in the rd mouse is caused by a defect in the beta subunit of rod cGMP-phosphodiesterase, *Nature* 347 (1990), pp. 677-680

Boyden et al., 2005—E. S. Boyden, F. Zhang, E. Bamberg, G. Nagel and K. Deisseroth, Millisecond-timescale, genetically targeted optical control of neural activity, *Nat. Neurosci.* 8 (2005), pp. 1263-1268

Chang et al., 2002—B. Chang, N. L. Hawes, R. E. Hurd, M. T. Davisson, S. Nusinowitz and J. R. Heckenlively, Retinal degeneration mutants in the mouse, *Vision Res.* 42 (2002), pp. 517-525

Cui et al., 2003—J. Cui, Y. P. Ma, S. A. Lipton and Z.-H. Pan, Glycine receptors and glycinergic synaptic input at the axon terminals of mammalian retinal rod bipolar cells. *J. Physiol.* 553 (2003), pp. 895-909

Dacey et al., 2005 D. M. Dacey, H. W. Liao, B. B. Peterson, F. R. Robinson, V. C. Smith, J. Pokorny, K. W. Yau and P. D. Gamlin, Melanopsin-expressing ganglion cells in primate retina signal colour and irradiance and project to the LGN, *Nature* 433 (2005), pp. 749-754

Fitzsimons et al., 2002—H. L. Fitzsimons, R. J. Bland and M. J. During, Promoters and regulatory elements that improve adeno-associated virus transgene expression in the brain, *Methods* 28 (2002), pp. 227-236

Flannery et al., 1997—J. G. Flannery, S. Zolotukhin, M. I. Vaquero, M. M. LaVail, N. Muzyczka and W. W. Hauswirth, Efficient photoreceptor-targeted gene expression in vivo by recombinant adeno-associated virus, *Proc. Natl. Acad. Sci. USA* 94 (1997), pp. 6916-6921

Flotte, 2004—T. R. Flotte, Gene therapy progress and prospects: recombinant adeno-associated virus (rAAV) vectors, *Gene Ther.* 11 (2004), pp. 805-810

Harvey et al., 2002—A. R. Harvey, W. Kamphuis, R. Eggers, N. A. Symons, B. Blits, S. Niclou, G. J. Boer and J. Verhaagen, Intravitreal injection of adeno-associated viral vectors results in the transduction of different types of retinal neurons in neonatal and adult rats: a comparison with lentiviral vectors, *Mol. Cell. Neurosci.* 21 (2002), pp. 141-157

Humphries et al., 1992—P. Humphries, P. Kenna and G. J. Farrar, On the molecular genetics of retinitis pigmentosa, *Science* 256 (1992), pp. 804 808

Ishizuka et al., 2006—T. Ishizuka, M. Kakuda, R. Araki and H. Yawo, Kinetic evaluation of photosensitivity in genetically engineered neurons expressing green algae light-gated channels, *Neurosci. Res.* 54 (2006), pp. 85-94

Jimenez et al., 1996—A. J. Jimenez, J. M. Garcia-Fernandez, B. Gonzalez and R. G. Foster, The spatio-temporal pattern of photoreceptor degeneration in the aged rd/rd mouse retina, *Cell Tissue Res.* 284 (1996), pp. 193-202

Jones and Marc, 2005 B. W. Jones and R. E. Marc, Retinal remodeling during retinal degeneration, *Exp. Eye Res.* 81 (2005), pp. 123 137

Jones et al., 2003—B. W. Jones, C. B. Watt, J. M. Frederick, W. Baehr, C. K. Chen, E. M. Levine, A. H. Milam, M. M. Lavail and R. E. Marc, Retinal remodeling triggered by photoreceptor degenerations, *J. Comp. Neurol.* 464 (2003), pp. 1-16

Kaneko, 1970—A. Kaneko, Physiological and morphological identification of horizontal, bipolar, and amacrine cells in the goldfish retina, *J. Physiol.* 207 (1970), pp. 623-633

Kateriya et al., 2004—S. Kateriya, G. Nagel, E. Bamberg and P. Hegemann, "Vision" in single-celled algae, *News Physiol. Sci.* 19 (2004), pp. 133-137

Kim et al., 1992—C. I. Kim, M. A. Leo and C. S. Lieber, Retinol forms retinoic acid via retinal, *Arch. Biochem. Biophys.* 294 (1992), pp. 388 393

Li et al., 2005—X. Li, D. V. Gutierrez, M. G. Hanson, J. Han, M. D. Mark, H. Chiel, P. Hegemann, L. T. Landmesser and S. Herlitze, Fast noninvasive activation and inhibition of neural and network activity by vertebrate rhodopsin and green algae channelrhodopsin, *Proc. Natl. Acad. Sci. USA* 102 (2005), pp. 17816-17821

Lund et al., 2001—R. D. Lund, A. S. Kwan, D. J. Keegan, Y. Sauve, P. J. Coffey and J. M. Lawrence, Cell transplantation as a treatment for retinal disease, *Prog. Retin. Eye Res.* 20 (2001), pp. 415-449

Martin et at., 2003—K. R. Martin, H. A. Quigley, D. J. Zack, H. Levkovitch-Verbin, J. Kielczewski, D. Valenta, L. Baumrind, M.E. Pease, R. L. Klein and W. W. Hauswirth, Gene therapy with brain-derived neurotrophic factor as a protection: retinal ganglion cells in a rat glaucoma model, *Invest. Ophthalmol. Vis. Sci.* 44 (2003), pp. 4357-4365

McLaughlin et al., 1993—M. E. McLaughlin, M. A. Sandberg, E. L. Berson and T. P. Dryja, Recessive mutations in the gene encoding the beta-subunit of rod phosphodiesterase in patients with retinitis pigmentosa, *Nat. Genet.* 4 (1993), pp. 130-134

Melyan et at., 2005—Z. Melyan, E. E. Tarttelin, J. Bellingham, R. J. Lucas and M. W. Hankins, Addition of human melanopsin renders mammalian cells photoresponsive, *Nature* 433 (2005), pp. 741-745

Milam et al., 1998—A. H. Milam, Z. Y. Li and R. N. Fariss, Histopathology of the human retina in retinitis pigmentosa, *Prog. Retin. Eye Res.* 17 (1998), pp. 175-205

Nagel et al., 2002—G. Nagel, D. Ollig, M. Fuhrmann, S. Kateriya, A. M. Musci, E. Bamberg and P. Hegemann, Channelrhodopsin-1: a light-gated proton channel in green algae, *Science* 296 (2002), pp. 2395-2398

Nagel et al., 2003—G. Nagel, T. Szellas, W. Huhn, S. Kateriya, N. Adeishvili, P. Berthold, D. Ollig, P. Hegemann and E. Bamberg, Channelrhodopsin-2, a directly light-gated cation-selective membrane channel, *Proc. Natl. Acad. Sci. USA* 100 (2003), pp. 13940-13945

Oesterhelt, 1998—D. Oesterhelt, The structure and mechanism of the family of retinal proteins from halophilic archaea, *Curr. Opin. Struct. Biol.* 8 (1998), pp. 489-500

Oesterhelt and Stoeckenius, 1973—D. Oesterhelt and W. Stoeckenius, Functions of a new photoreceptor membrane, *Proc. Natl. Acad. Sci. USA* 70 (1973), pp. 2853-2857

Olshevskaya et al., 2004—E. V. Olshevskaya, P. D. Calvert, M. L. Woodruff, I. V. Peshenko, A. B. Savchenko, C. L. Makino, Y. S. Ho, G. L. Fain and A. M. Dizhoor, The Y99C mutation in guanylyl cyclase-activating protein 1 increases intracellular $Ca^{2+}$ and causes photoreceptor degeneration in transgenic mice, *J. Neurosci.* 24 (2004), pp. 6078 6085

Pan, 2000—Z.-H. Pan, Differential expression of high- and two types of low-voltage-activated calcium currents in rod and cone bipolar cells of the rat retina, *J. Neurophysiol.* 83 (2000), pp. 513-527

Panda et al., 2005—S. Panda, S. K. Nayak, B. Campo, J. R. Walker, J. B. Hogenesch and T. Jegla, Illumination of the melanopsin signaling pathway, *Science* 307 (2005), pp. 600-604

Partridge and De Grip, 1991—J. C. Partridge and W. J. De Grip, A new template for rhodopsin (vitamin $A_1$ based) visual pigments, *Vision Res.* 31 (1991), pp. 619-630

Qiu et al., 2005—X. Qiu, T. Kumbalasiri, S. M. Carlson, K. Y. Wong, V. Krishna, T. Provencio and D. M. Berson, Induction of photosensitivity by heterologous expression of melanopsin, *Nature* 433 (2005), pp. 745-749

Santos et al., 1997—A. Santos, M. S. Humayun, E. de Juan Jr., R. J. Greenburg, M. J. Marsh, I. B. Klock and A. H. Milam, Preservation of the inner retina in retinitis pigmentosa. A morphometric analysis, *Arch. Ophthalmol.* 115 (1997), pp. 511-515

Schiller et al., 1986—P. H. Schiller, J. H. Sandell and J. H. Maunsell, Functions of the ON and OFF channels of the visual system, *Nature* 322 (1986), pp. 824 825

Sineshchekov et al., 2002—O. A. Sineshchekov, K. H. Jung and J. L. Spudich, Two rhodopsins mediate phototaxis to low- and high-intensity light in Chlamydomonas reinhardtii, *Proc. Natl. Acad. Sci. USA* 99 (2002), pp. 8689-8694

Steinberg et al., 1980—R. H. Steinberg, S. K. Fisher and D. H. Anderson, Disc morphogenesis in vertebrate photoreceptors, *J. Comp. Neurol.* 190 (1980), pp. 501-518

Strettoi and Pignatelli, 2000—E. Strettoi and V. Pignatelli, Modifications of retinal neurons in a mouse model of retinitis pigmentosa, *Proc. Natl. Acad. Sci. USA* 97 (2000), pp. 11020-11025

Stryer, 1991—L. Stryer, Visual excitation and recovery, *J. Biol. Chem.* 266 (1991), pp. 10711-10724

Sung et al., 1991—C. H. Sung, C. M. Davenport, J. C. Hennessey, I. H. Maumenee, S. G. Jacobson, J. R. Heckenlively, R. Nowakowski, G. Fishman, P. Gouras and J. Nathans, Rhodopsin mutations in autosomal dominant retinitis pigmentosa, *Proc. Natl. Acad. Sci. USA* 88 (1991), pp. 6481-6485

Suzuki et al., 2003—T. Suzuki, K. Yamasaki, S. Fujita, K. Oda, M. Iseki, K. Yoshida, M. Watanabe, H. Daiyasu, H. Toh and E. Asamizu et al., Archacal-type rhodopsins in Chlamydomonas: model structure and intracellular localization, *Biochem. Biophys. Res. Commun.* 301 (2003), pp. 711-717

Tian and Copenhagen, 2003—N. Tian and D. R. Copenhagen, Visual stimulation is required for refinement of ON and OFF pathways in postnatal retina, *Neuron* 39 (2003), pp. 85-96

Thompson and Gal, 2003—D. A. Thompson and A. Gal, Vitamin A metabolism in the retinal pigment epithelium: genes, mutations, and diseases, *Prog. Retin. Eye Res.* 22 (2003), pp. 683-703

Tu et al., 2005—D.C. Tu, D. Zhang, J. Demas, E. B. Slutsky, I. Provencio, T. E. Holy and R. N. Van Gelder, Physiologic diversity and development of intrinsically photosensitive retinal ganglion cells, *Neuron* 48 (2005), pp. 987-999

Wald, 1968—G. Wald, The molecular basis of visual excitation, *Nature* 219 (1968), pp. 800-807 Wässle, 2004—H. Wässle, Parallel processing in the mammalian retina, *Nat. Rev. Neurosci.* 5 (2004), pp. 747-757

Weleber, 1994—R. G. Weleber, Retinitis pigmentosa and allied disorders. In: S. J. Ryan, Editor, *Retina*, Mosby, St. Louis, Mo. (1994), pp. 335-466

Werblin and Dowling, 1969—F. S. Werblin and J. E. Dowling, Organization of the retina of the mudpuppy, Necturus maculosus. 11. Intracellular recording, *J. Neurophysiol.* 32 (1969), pp. 339-355

Zemelman et al., 2002—B. V. Zemelman, G. A. Lee, M. Ng and G. Miesenbock, Selective photostimulation of genetically chARGed neurons, *Neuron* 33 (2002), pp. 15-22

Zrenner, 2002—E. Zrenner, Will retinal implants restore vision?, *Science* 295 (2002), pp. 1022-1025

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by those skilled in the art in light of the teachings and guidance presented herein, in combination with the knowledge of one of ordinary skill in the art.

---

We claim:

1. A method of restoring photosensitivity to retinal neurons of a subject suffering from vision loss or blindness, which method comprises: (a) delivering to a retina of said subject in which photoreceptors are degenerating or have already died a nucleic acid vector comprising a nucleic acid encoding a polypeptide of SEQ ID NO: 3 or a polypeptide having 98% or 99% sequence identity thereto, operably linked to a promoter sequence; and (b) expressing said polypeptide in said retinal neurons, wherein the expression of the polypeptide renders said retinal neurons photosensitive, thereby restoring photosensitivity to said retinal neurons.

2. The method of claim 1, wherein the nucleic acid vector is a recombinant adeno-associated virus (rAAV) vector.

3. The method of claim 2, wherein the rAAV vector is selected from the group consisting of AAV1, AAV2, AAV3, AAV4, AAV5 and AAV6.

4. The method of claim 1, wherein the promoter is a constitutive promoter.

5. The method of claim 1, wherein the promoter is selected from the group consisting of a hybrid CAG promoter, a CMV promoter, an mGluR6 promoter, a Pcp2 (L7) promoter and a neurokinin-3 (NK-3) promoter.

6. The method of claim 1, wherein the nucleic acid vector comprises a CAG promoter, a woodchuck posttranscriptional regulatory element (WPRE) and a bovine or human growth hormone polyadenylation sequence.

7. The method of claim 1, wherein the method increases visual evoked potential (VEP) in a visual cortex of the subject.

8. The method of claim 1, wherein the vision loss or blindness is a result of a degenerative disease.

9. The method of claim 8, wherein the disease is retinitis pigmentosa or age-related macular degeneration.

10. The method of claim 1, wherein the subject is human.

* * * * *